(12) United States Patent
Prakash et al.

(10) Patent No.: US 10,683,323 B2
(45) Date of Patent: Jun. 16, 2020

(54) MOGROSIDES, COMPOSITIONS AND THEIR PURIFICATION

(71) Applicant: The Coca-Cola Company, Atlanta, GA (US)

(72) Inventors: Indra Prakash, Alpharetta, GA (US); Venkata Sai Prakash Chaturvedula, Gilbert, AZ (US)

(73) Assignee: The Coca-Cola Company, Atlanta, GA (US)

( * ) Notice: Subject to any disclaimer, the term of this patent is extended or adjusted under 35 U.S.C. 154(b) by 229 days.

(21) Appl. No.: 14/776,102

(22) PCT Filed: Mar. 18, 2014

(86) PCT No.: PCT/US2014/031043
§ 371 (c)(1),
(2) Date: Sep. 14, 2015

(87) PCT Pub. No.: WO2014/146089
PCT Pub. Date: Sep. 18, 2014

(65) Prior Publication Data
US 2016/0039864 A1    Feb. 11, 2016

Related U.S. Application Data

(60) Provisional application No. 61/788,093, filed on Mar. 15, 2013.

(51) Int. Cl.
*C07J 17/00* (2006.01)
*A23L 27/30* (2016.01)
*A23L 2/60* (2006.01)
*A23L 2/38* (2006.01)

(52) U.S. Cl.
CPC ............... *C07J 17/005* (2013.01); *A23L 2/60* (2013.01); *A23L 27/36* (2016.08); *A23L 2/38* (2013.01); *A23V 2002/00* (2013.01)

(58) Field of Classification Search
CPC ........... C07J 17/005; A23L 27/36; A23L 2/60; A23L 2/38; A23V 2002/00
USPC .......................................... 426/72, 548, 590
See application file for complete search history.

(56) References Cited

U.S. PATENT DOCUMENTS

| | | |
|---|---|---|
| 2009/0162511 A1 | 6/2009 | Shi et al. |
| 2011/0027413 A1 | 2/2011 | Jia et al. |
| 2011/0052755 A1 | 3/2011 | Fiorenza et al. |

FOREIGN PATENT DOCUMENTS

| | | |
|---|---|---|
| EP | 2090181 | 8/2009 |
| WO | WO 2015/082012 | 6/2015 |

OTHER PUBLICATIONS

International Search Report for PCT/US2014/031043, dated Nov. 10, 2014.
Chaturvedula et al. Enzymatic and acid hydrolysis of steviol and cucurbitane glycosides. Int J Pharm Biomed Res 2(2): 135-139, 2011.
Chaturvedula et al. Additional cucurbitane glycosides from Siraitia grosvenorii. IOSR Journal of Pharmacy (IOSRPHR) 2(4): 7-12, 2012.
PubChem. Compound Summary for CID 56776288, Create Date: Mar. 8, 2012. [Retrieved on Jul. 14, 2014]. Retrieved from the internet. URL:https://pubchem.ncbi.nlm.nih.gov/summary.cgi?cid=56776288.
Supplemental European Search Report for European Patent Application No. 14764632.7, dated Aug. 3, 2016.
Chaturvedula et al. Cucurbitane glycosides from Siraitia grosvenorii. Journal of Carbohydrate Chemistry, vol. 30, No. 1, Jan. 1, 2011.
Akihisa et al. Cucurbitane glycosides from fruits of Siraitia grosvenorii and their inhibitory effects on Epstein-Barr virus activation, Journal of Natural products, American Chemical Society, vol. 70, No. 5, Jan. 1, 2007.

*Primary Examiner* — Leslie A Wong
(74) *Attorney, Agent, or Firm* — King & Spalding

(57) ABSTRACT

Novel mogrosides and methods for heir purification are provided herein. In addition, compositions comprising said novel mogrosides and methods for preparing the same are provided. The present invention relates generally to novel mogrosides, as well as compositions comprising such novel mogrosides, including consumables. The present invention further extends to methods of purifying such novel mogrosides, methods for preparing compositions (e.g., consumables) comprising such novel mogrosides and methods of enhancing the flavor or sweetness of consumables using these novel mogrosides.

6 Claims, 10 Drawing Sheets

MOGROSIDES, COMPOSITIONS AND THEIR PURIFICATION

CROSS REFERENCE TO RELATED APPLICATIONS

This application is a national phase application under 35 U.S.C. § 371 of International Application No. PCT/US2014/031043, filed on 18 Mar. 2014, which claims the benefit of U.S. Provisional Application No. 61/788,093, filed on 15 Mar. 2013, the disclosures of both of which are incorporated herein by reference.

FIELD OF THE INVENTION

The present invention relates generally to novel mogrosides, as well as compositions comprising such novel mogrosides, including consumables. The present invention further extends to methods of purifying such novel mogrosides, methods for preparing compositions (e.g., consumables) comprising such novel mogrosides and methods of enhancing the flavor or sweetness of consumables using these novel mogrosides.

BACKGROUND OF THE INVENTION

Luo han guo is the common name for the sweet extract made from the fruit of *Siraitia grosvenorii*, a herbaceous perennial vine of the Cucurbitaceae family native to Southern China and Northern Thailand. Luo han guo extracts are nearly 250 times sweeter than sugar and are desirable as both non-caloric and natural in origin.

The sweetness of Luo han guo is generally attributed to mogrosides present at the level of about 1% by weight in the fleshy part of the fruit. Both the fresh and dried fruits are extracted to yield a powder that is 80% or more mogrosides. Yet, some mogrosides, such as mogroside III and mogroside IIE, can be tasteless or even bitter. Luo han guo extracts may also contain multiple impurities which possess undesirable organoleptic properties, which can affect the color, smell and taste profile of Luo han guo extract.

There remains a need for natural, non-caloric sweeteners.

There remains a further need for methods for purifying mogrosides from Luo han guo.

SUMMARY OF THE INVENTION

The present invention relates generally to novel mogrosides and compositions comprising such novel mogrosides, as well as methods of purifying such novel mogrosides, methods for preparing compositions (e.g., consumables) comprising such novel mogrosides and methods of enhancing the flavor or sweetness of consumables using these novel mogrosides.

In one aspect, the present invention is a novel mogroside.

In one embodiment, the present invention is a novel mogroside of formula (1):

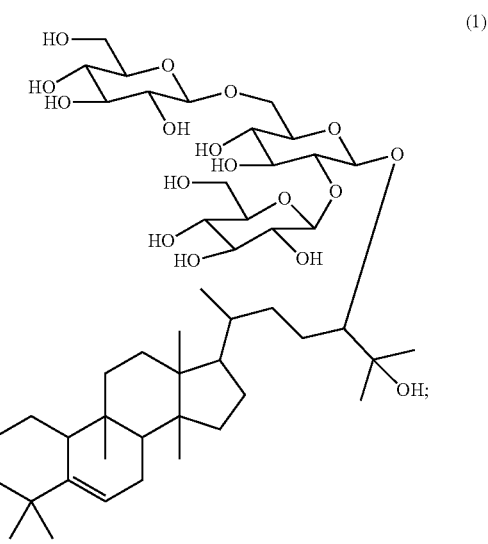

wherein $R^1$ is selected from the group consisting of a monosaccharide; an oligosaccharide; hydrogen; hydroxyl; halo; acyl; substituted or unsubstituted ester; substituted or unsubstituted aryl; a substituted or unsubstituted heteroaryl; substituted or unsubstituted alkyl; substituted or unsubstituted ring of 5 to 7 members; substituted or unsubstituted heterocycle; substituted or unsubstituted alkoxy; substituted or unsubstituted alkoxyalkyl; substituted or unsubstituted alkylthio; substituted or unsubstituted alkylthioalkyl; substituted or unsubstituted alkylsulfonyl; substituted or unsubstituted alkylsulfonylalkyl; $C_1$-$C_6$ straight alkyl; $C_1$-$C_6$ branched alkyl; $C_2$-$C_6$ alkenyl; $NH_2$; $NHR_2$; $NR_2$; $OSO_3H$; $OSO_2R$; $OC(O)R$; $OCO_2H$; $CO_2R$; $C(O)NH_2$; $C(O)NHR$; $C(O)NR_2$; $SO_3H$; $SO_2R$; $SO_2NH_2$; $SO_2NHR$; $SO_2NR_2$; or $OPO_3H$; and R is alkyl, substituted alkyl, alkenyl, substituted alkenyl, alkynyl, substituted alkynyl, substituted aryl, heteroaryl, substituted heteroaryl, or when attached to a nitrogen atom, two adjacent R groups may combine to form a ring of 5 to 7 members.

In particular embodiments, $R^1$ is an oligosaccharide comprising from two to five sugars.

In a more particular embodiment, the present invention is a novel mogroside selected from the group consisting of (1a), (1b) and (1c):

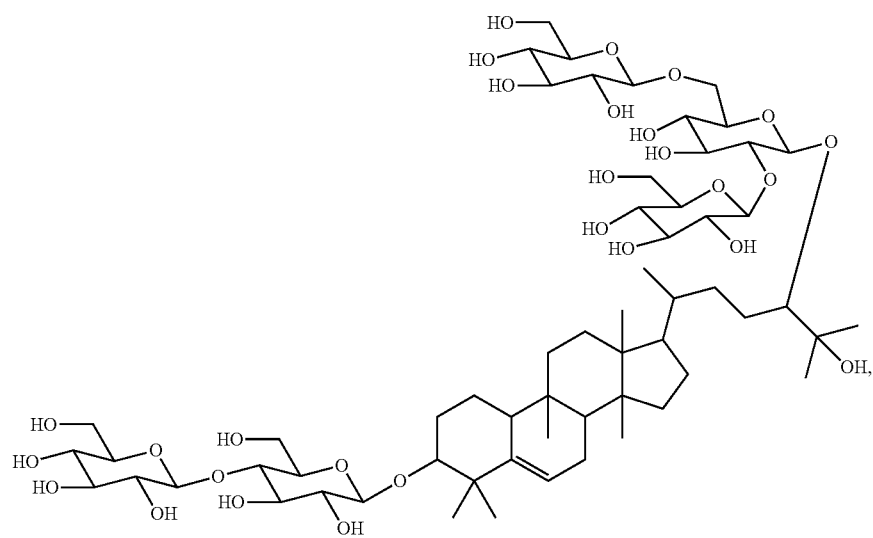
(1a)
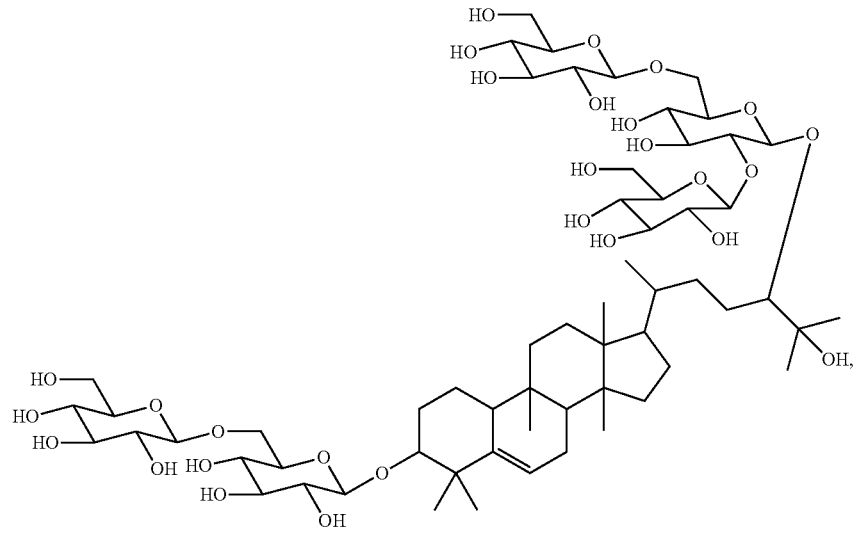
(1b)

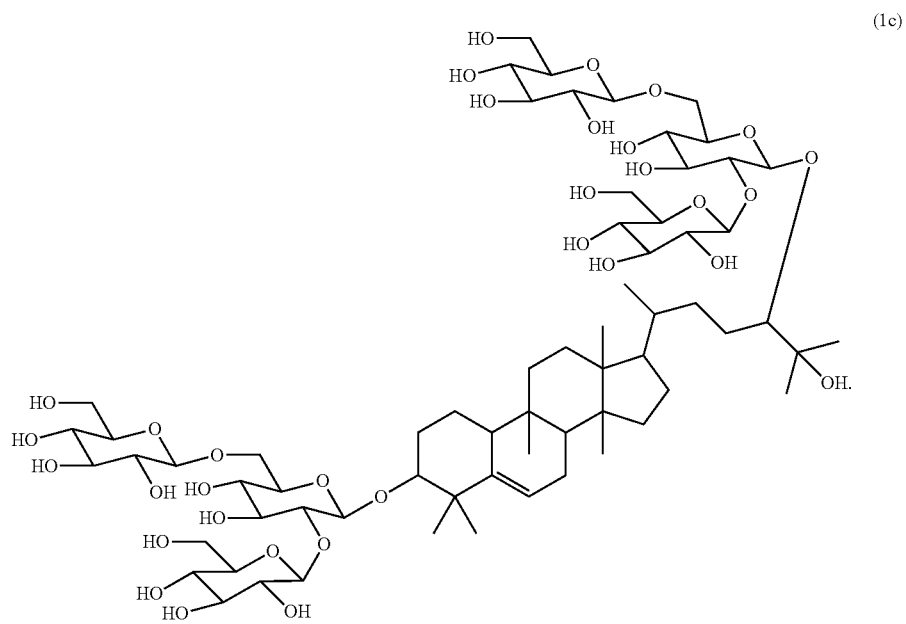
(1c)
In another embodiment, the present invention is a novel mogroside of formula (2):
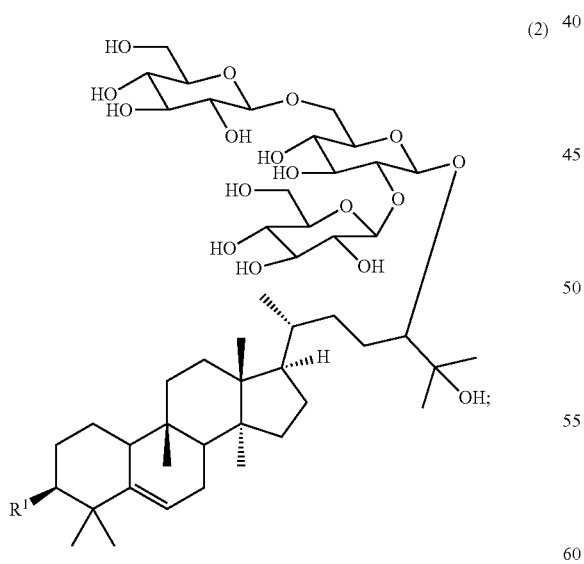
(2)
wherein $R^1$ remains as defined above.

In more particular embodiment, the present invention is a novel mogroside selected from (2a), (2b), and (2c):
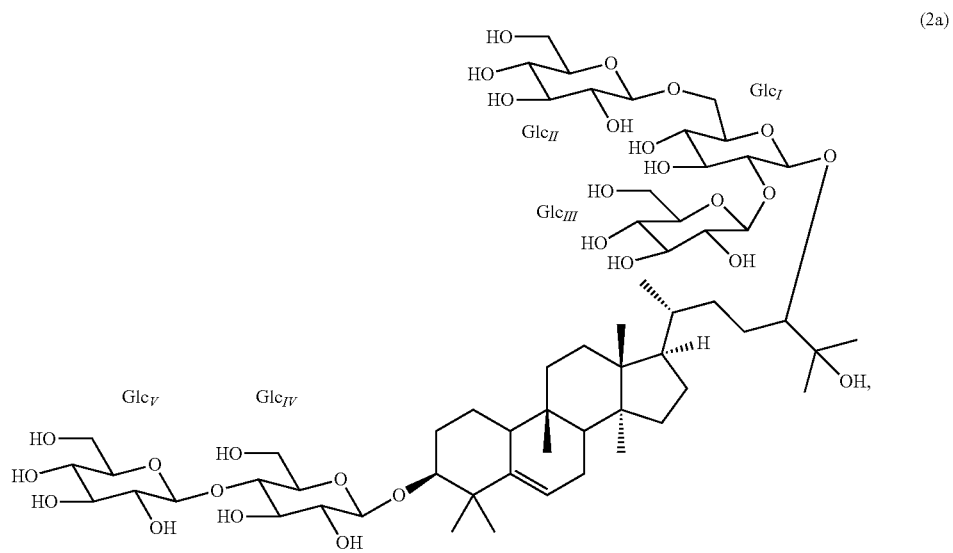
(2a)
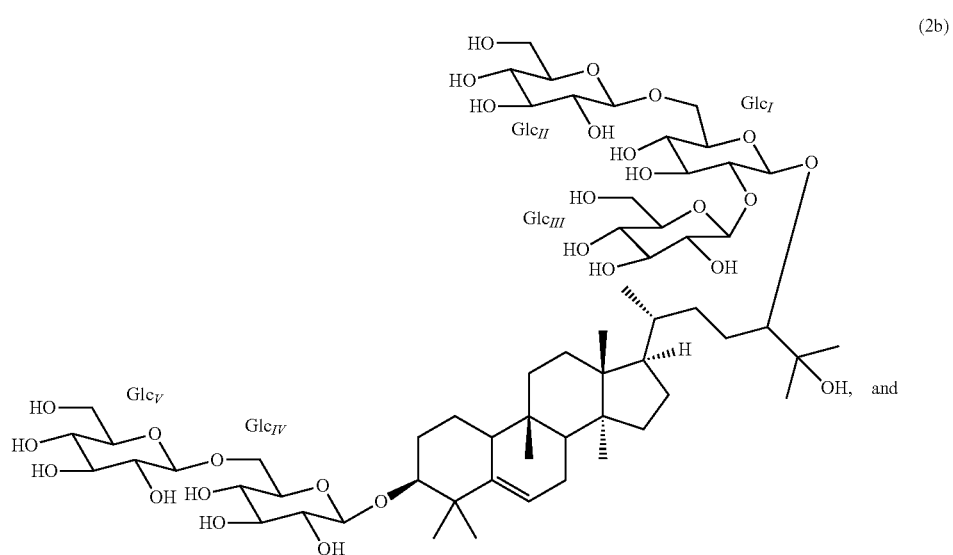
(2b)

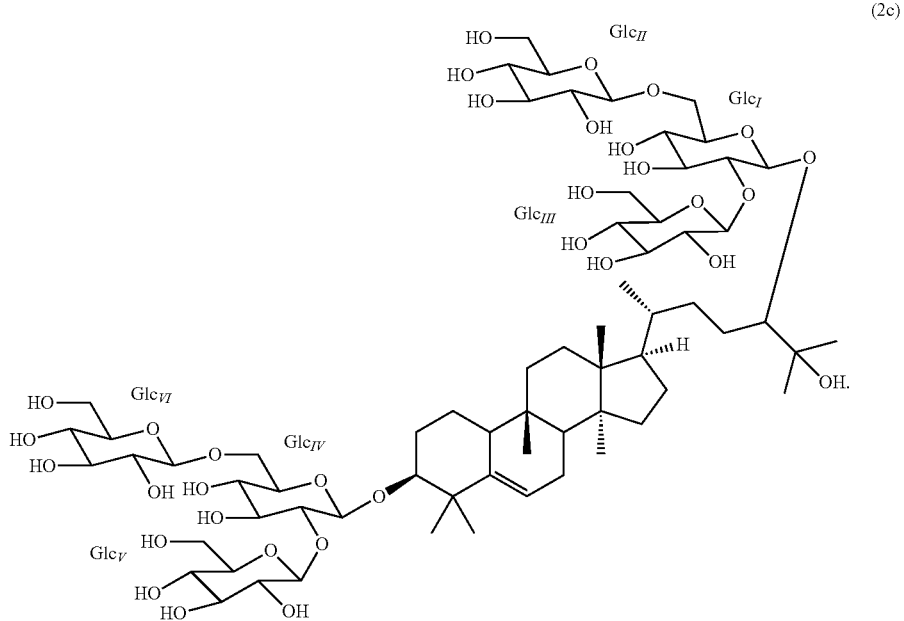
(2c)

In particular embodiments, $R^1$ is an oligosaccharide comprising from two to five sugars.

In other embodiments, $R^1$ is an oligosaccharide comprising a monosaccharide selected from, but not limited to, the group of glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, fucose, rhamnose, arabinose, turanose and sialose.

In some embodiments, the compound of formula (1) is sweet.

In another aspect, the present invention is a method for purifying a compound of formula (1) comprising (i) passing a solution comprising mogrosides through an HPLC column and (ii) eluting fractions comprising a compound of formula (1). The HPLC column can be any suitable HPLC preparative scale column. The fractions may be eluted by adding an appropriate eluent. The eluent can be any suitable solvent or combination of solvents. In one embodiment, the eluent is water and/or acetonitrile. The method may optionally comprise additional steps, such as removal of solvents from the eluted solution to provide a concentrate comprising a compound of formula (1).

In a further aspect, the present invention is a composition comprising a compound of formula (1).

In one embodiment, the present invention is a sweetener composition comprising a compound of formula (1).

In another embodiment, the present invention is a flavor-enhancing composition comprising a compound of formula (1), wherein the compound of formula (1) is present in an amount effective to provide a concentration at or below the threshold flavor recognition level of the compound of formula (1) when the flavor-enhancing composition is added to a consumable In a particular embodiment, the compound of formula (1) is present in an amount effective to provide a concentration below the threshold flavor recognition level of the compound of formula (1) when the flavor-enhancing composition is added to a consumable. In one embodiment, the compound of formula (1) is present in an amount effective to provide a concentration at least about 1%, at least about 5%, at least about 10%, at least about 15,% at least about 20% or at least about 25% or more below the threshold flavor recognition level of the compound of formula (1) when the flavor-enhancing composition is added to a consumable.

In yet another embodiment, the present invention is a sweetness-enhancing composition comprising a compound of formula (1), wherein the compound of formula (1) is present in an amount effective to provide a concentration at or below the threshold sweetness recognition level of the compound of formula (1) when the sweetness-enhancing composition is added to a consumable In a particular embodiment, the compound of formula (1) is present in an amount effective to provide a concentration below the threshold sweetness recognition level of the compound of formula (1) when the sweetness-enhancing composition is added to a consumable. In one embodiment, the compound of formula (1) is present in an amount effective to provide a concentration at least about 1%, at least about 5%, at least about 10%, at least about 15,% at least about 20% or at least about 25% or more below the threshold sweetness recognition level of the compound of formula (1) when the sweetness-enhancing composition is added to a consumable.

In yet another embodiment, the present invention is a consumable comprising a compound of formula (1). Suitable consumables include, but are not limited to, liquid-based or dry consumables, such as, for example, pharmaceutical compositions, edible gel mixes and compositions, dental compositions, foodstuffs, beverages and beverage products.

In a particular embodiment, the present invention is a beverage comprising a compound of formula (1). In a particular embodiment, the compound of formula (1) is present in the beverage at a concentration that is above, at or below the threshold sweetness recognition concentration of the compound of formula (1).

In another particular embodiment, the present invention is a beverage product comprising a compound of formula 1. In a particular embodiment, the compound of formula (1) is present in the beverage product at a concentration that is above, at or below the threshold flavor recognition concentration of the compound of formula (1).

In another aspect, the present invention is a method of preparing a consumable comprising (i) providing a consumable matrix and (ii) adding a compound of formula (1) to the consumable matrix to provide a consumable. In a particular embodiment, the compound of formula (1) is present in the consumable in a concentration above, at or below the threshold sweetness recognition of the compound of formula (1). In another particular embodiment, the compound of formula (1) is present in the consumable in a concentration above, at or below the threshold flavor recognition of the compound of formula (1).

In a particular embodiment, the present invention is a method of preparing a beverage comprising (i) providing a beverage matrix and (ii) adding a compound of formula (1) to the consumable matrix to provide a beverage. In a particular embodiment, the compound of formula (1) is present in the consumable in a concentration above, at or below the threshold sweetness recognition of the compound of formula (1). In another particular embodiment, the compound of formula (1) is present in the consumable in a concentration above, at or below the threshold flavor recognition concentration of the compound of formula (1).

In another aspect, the present invention is a method of enhancing the sweetness of a consumable comprising (i) providing a consumable comprising at least one sweet ingredient and (ii) adding a compound of formula (1) to the consumable to provide a consumable with enhanced sweetness, wherein the compound of formula (1) is present in the beverage with enhanced sweetness at a concentration at or below the threshold sweetness recognition concentration of the compound of formula (1).

In a particular embodiment, the present invention is a method of enhancing the sweetness of a beverage comprising (i) providing a beverage comprising at least one sweet ingredient and (ii) adding a compound of formula (1) to the beverage to provide a beverage with enhanced sweetness, wherein the compound of formula (1) is present in the beverage with enhanced sweetness at a concentration below the threshold sweetness recognition concentration of the compound of formula (1). In one embodiment, the concentration of the compound of formula (1) is present in the beverage with enhanced sweetness at a concentration that is at least about 1%, at least about 5%, at least about 10%, at least about 15%, at least about 20%, or at least about 25% or more below the threshold sweetness recognition concentration of the compound of formula (1).

In a further aspect, the present invention is a method of enhancing the flavor of a consumable comprising (i) providing a consumable comprising at least one flavor ingredient and (ii) adding a compound of formula (1) to the consumable to provide a consumable with enhanced flavor, wherein the compound of formula (1) in present in the consumable with enhanced flavor at a concentration at or below the threshold flavor recognition concentration of the compound of formula (1).

In a particular embodiment, the present invention is a method of enhancing the flavor of a beverage comprising (i) providing a beverage comprising at least one flavor ingredient and (ii) adding a compound of formula (1) to the beverage to provide a beverage with enhanced flavor, wherein the compound of formula (1) is present in the beverage with enhanced flavor in a concentration at or below the threshold flavor recognition concentration of the compound of formula (1).). In one embodiment, the concentration of the compound of formula (1) is present in the beverage with enhanced sweetness at a concentration that is at least about 1%, at least about 5%, at least about 10%, at least about 15%, at least about 20%, or at least about 25% or more below the threshold flavor recognition concentration of the compound of formula (1).

In the above methods, the compound of formula (1) may be added as such, or in the form of a composition comprising the compound of formula (1). When the compound of formula 1 is provided as a composition, the concentration of the compound of formula (1) in the composition is effective to provide a concentration above, at or below the threshold flavor or sweetener composition of the compound of formula (1), when the composition is added to the consumable, e.g., the beverage.

In some embodiments, the compositions of the present invention comprise one or more additional mogrosides, where the additional mogrosides are selected from, but not limited to, the group consisting of Luo han guo extract, by-products of other mogrosides' isolation and purification processes, a commercially available Luo han guo extract, individual mogrosides and combinations thereof.

In other embodiments, the compositions of the present invention comprise one or more sweeteners or additional sweeteners. In one embodiment, the additional sweetener is a natural sweetener or a synthetic sweetener. In a particular embodiment, the additional sweetener is a high intensity sweetener. In a particular embodiment, the additional sweetener is a mogroside.

In some embodiments, the compositions of the present invention comprise one or more additives. In a particular embodiment, the additive is selected from the group consisting of carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

In some embodiments, the compositions of the present invention comprise one or more functional ingredients. In a particular embodiment, the functional ingredient is selected from the group consisting of waponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

In a particular embodiment, the present invention is a consumable comprising a compound of formula (1) and one or more additional mogrosides, sweeteners, additional sweeteners, additives or functional ingredients.

In another particular embodiment, the present invention is a beverage comprising a compound of formula (1) and one or more additional mogrosides, sweeteners, additional sweeteners, additives or functional ingredients.

DETAILED DESCRIPTION OF THE INVENTION

Figure 1A:
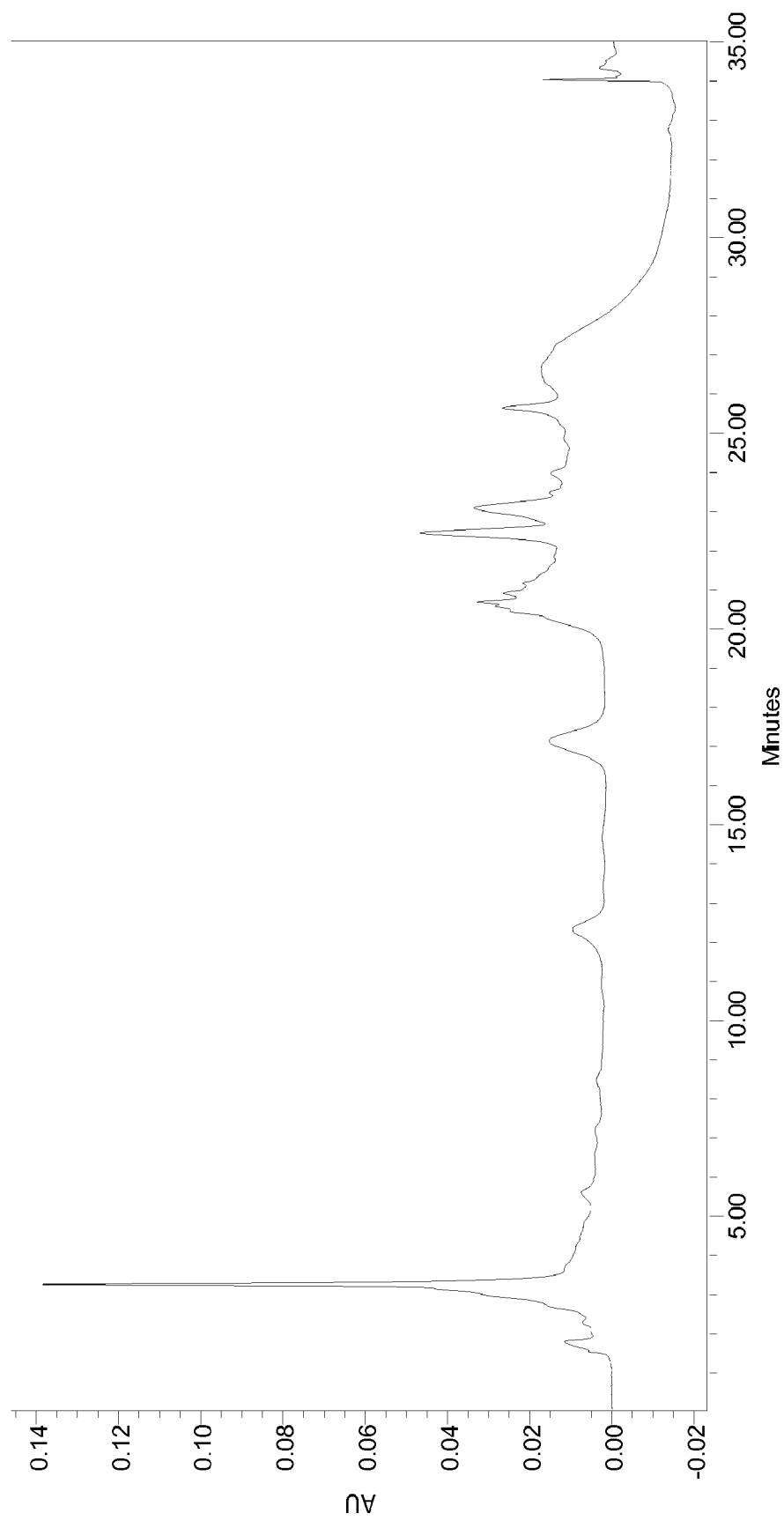
FIG. 1: HPLC chromatogram for the final purification of extracts VSPC-2973-43D (A) and VSPC-2973-45-ML-1 (B).

The present invention relates generally to novel mogrosides, as well as compositions comprising such novel mogrosides. The present invention further extends to methods of purifying such novel mogrosides and methods for preparing compositions (e.g., consumables) comprising such novel mogrosides or compositions, as well as methods for enhancing the flavor or sweetness of consumables using these novel mogroside and compositions.

I. Compounds

In one aspect, the present invention provides novel mogroside compounds.

In one embodiment, the present invention is a compound of formula (1):

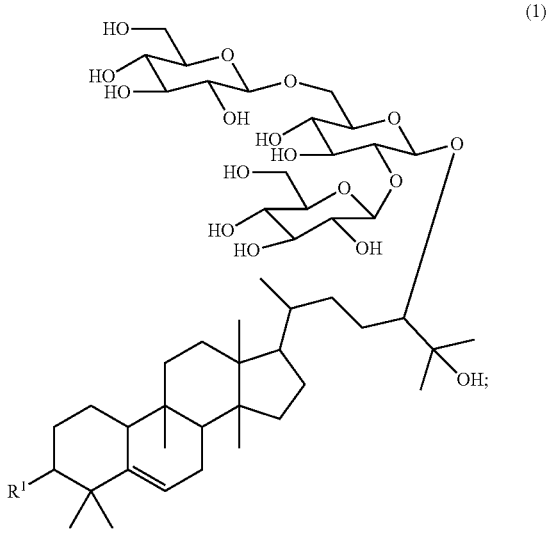

(1)

wherein $R^1$ is independently selected from the group consisting of a monosaccharide; an oligosaccharide; hydrogen; hydroxyl; halo; acyl; substituted or unsubstituted ester; substituted or unsubstituted aryl; a substituted or unsubstituted heteroaryl; substituted or unsubstituted alkyl; substituted or unsubstituted ring of 5 to 7 members; substituted or unsubstituted heterocycle; substituted or unsubstituted alkoxy; substituted or unsubstituted alkoxyalkyl; substituted or unsubstituted alkylthio; substituted or unsubstituted alkylthioalkyl; substituted or unsubstituted alkylsulfonyl; substituted or unsubstituted alkylsulfonylalkyl; $C_1$-$C_6$ straight alkyl; $C_1$-$C_6$ branched alkyl; $C_2$-$C_6$ alkenyl; $NH_2$; $NHR_2$; $NR_2$; $OSO_3H$; $OSO_2R$; $OC(O)R$; $OCO_2H$; $CO_2R$; $C(O)NH_2$; $C(O)NHR$; $C(O)NR_2$; $SO_3H$; $SO_2R$; $SO_2NH_2$; $SO_2NHR$; $SO_2NR_2$; or $OPO_3H$; and R is alkyl, substituted alkyl, alkenyl, substituted alkenyl, alkynyl, substituted alkynyl, substituted aryl, heteroaryl, substituted heteroaryl, or when attached to a nitrogen atom, two adjacent R groups may combine to form a ring of 5 to 7 members;

In one embodiment, $R^1$ is an oligosaccharide. In another embodiment, $R^1$ can be a branched or unbranched oligosaccharide.

The oligosaccharide may comprise two, three, four, five or more sugars. In one embodiment, $R^1$ is an oligosaccharide comprising two sugars. In still another embodiment, $R^1$ is an oligosaccharide comprising three sugars. In yet another embodiment, $R^1$ is an oligosaccharide comprising four sugars. In a further another embodiment, $R^1$ is an oligosaccharide comprising five sugars.

In some embodiments, $R^1$ is an oligosaccharide selected from, but not limited to, the group consisting of sucrose, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, fucose, rhamnose, arabinose, turanose, sialose and combinations thereof.

One of ordinary skill in the art will appreciate that compounds of formula (1) comprise one or more stereocenters. Each stereocenter may be in either the R or S configuration, depending on the arrangement and orientation of the atoms in space. Unless otherwise indicated, it should be understood that the compound of formula (1) may be of any suitable stereochemical configuration.

In one embodiment, the present invention is a compound of formula (1a):
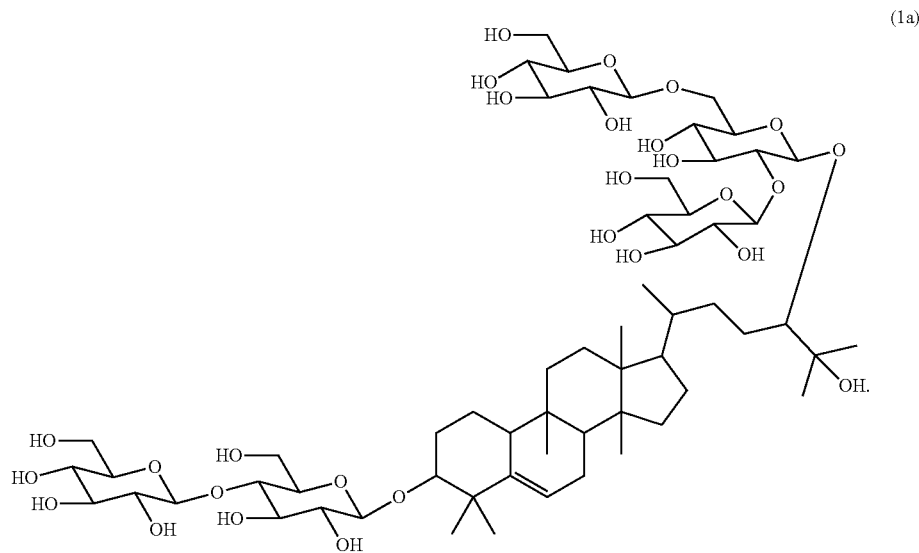
In another embodiment, the present invention is the compound of formula (1b):
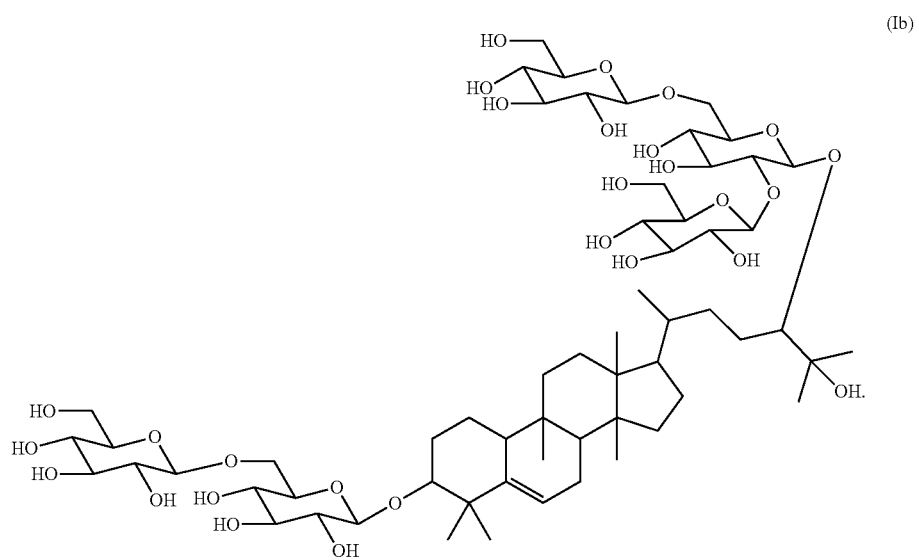

In still another embodiment, the present invention is the compound of formula (1c):

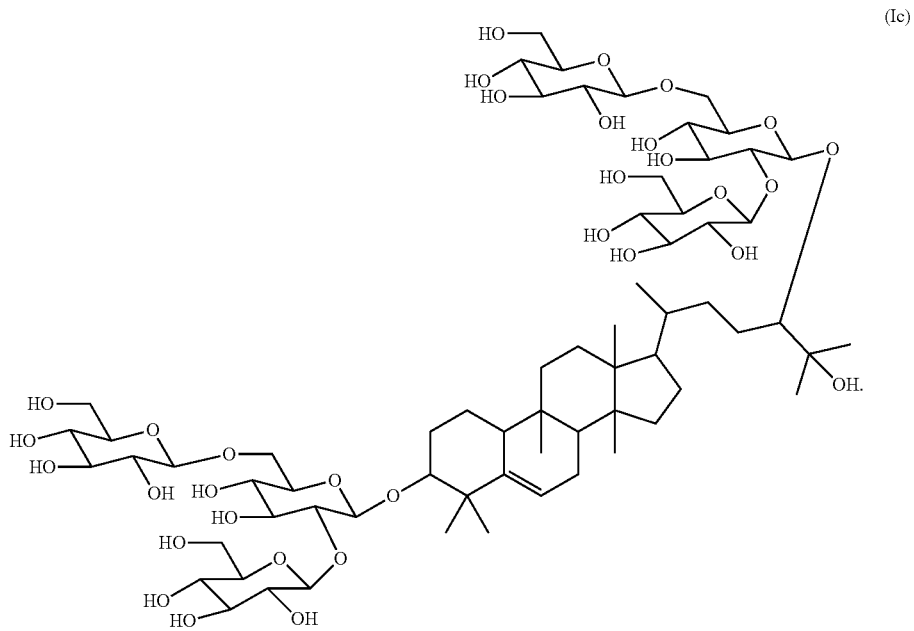

In other embodiments, the present invention is a compound of formula (2), wherein formula (2) is a subset of formula (1):

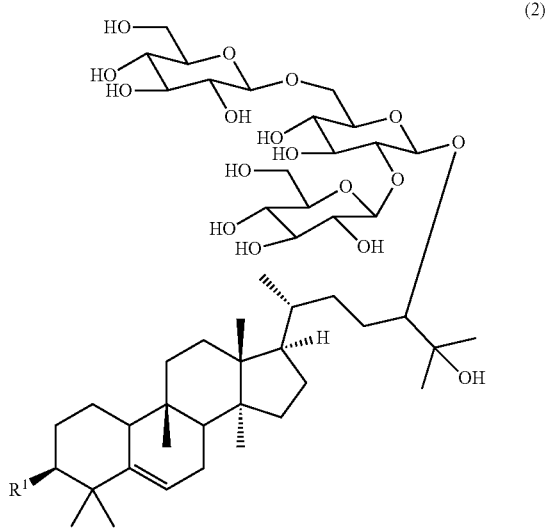

wherein $R^1$ is defined as set forth above.

In one embodiment, $R^1$ is an oligosaccharide. In another embodiment, $R^1$ can be a branched or unbranched oligosaccharide.

The oligosaccharide may comprise two, three, four, five or more sugars. In one embodiment, $R^1$ is an oligosaccharide comprising two sugars. In still another embodiment, $R^1$ is an oligosaccharide comprising three sugars. In yet another embodiment, $R^1$ is an oligosaccharide comprising four sugars. In a further another embodiment, $R^1$ is an oligosaccharide comprising five sugars.

In some embodiment, $R^1$ is an oligosaccharide comprising one or more glucoses. In particular embodiment, $R^1$ is an oligosaccharide comprising one glucose. In another embodiment, $R^1$ is an oligosaccharide comprising two glucoses. In another embodiment, $R^1$ is an oligosaccharide comprising three glucoses. In yet another embodiment, $R^1$ is an oligosaccharide comprising four glucoses.

In some embodiments, the oligosaccharide may comprise two or more monosaccharides linked together. Non-limiting examples of suitable monosaccharides include, but are not limited to glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, fucose, rhamnose, arabinose, turanose, sialose and combinations thereof.

The monosaccharides within a given oligosaccharide can be the same or different, i.e. an oligiosaccharide can contain two or more of the same monosaccharides or may contain two or more different monosaccharides.

The bonds between the monosaccharides of an oligosaccharide, and between the oligosaccharide and the R position of formulae (1) or (2), can be β-linkages or α-linkages. In yet another embodiment, the oligosaccharide is bonded with β-(1,2)-linkages, β-(1,3)-linkages, β-(1,4)-linkages, β-(1,6)-linkages, α-(1,2)-linkages, α-(1,3)-linkages, α-(1,4)-linkages, α-(1,6)-linkages, and any combination thereof.

In a particular embodiment, the present invention is the compound of formula (3β,9β,10α, 11α,24R)-3-[(4-O-β-D-glucospyranosyl-6-O-β-D-glucopyranosyl]-25-hydroxyl-9-methyl-19-norlanost-5-en-24-yl-[2-O-β-D-glucopyranosyl-6-O-β-D-glucopyranosyl]-β-D-glucopyranoside) (2a):

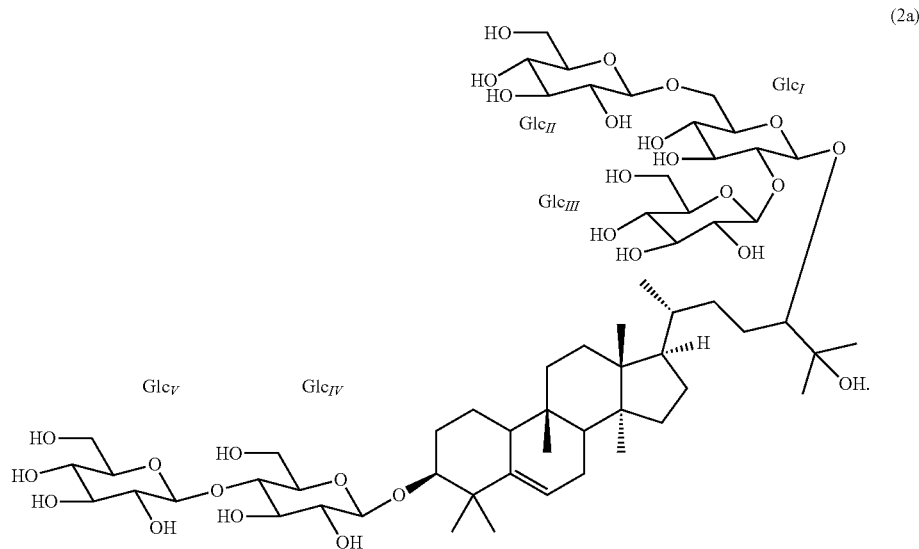

(2a)

In another particular embodiment, the present invention is the compound of formula (3β,9β,10α, 11α,24R)-3-[(6-O-β-D-glucopyranosyl-β-D-glucopyranosyl)oxy]-25-hydroxyl-9-methyl-19-norlanost-5-en-24-yl-[2-O-β-D-glucopyranosyl-6-O-β-D-glucopyranosyl]-β-D-glucopyranoside) (2b):

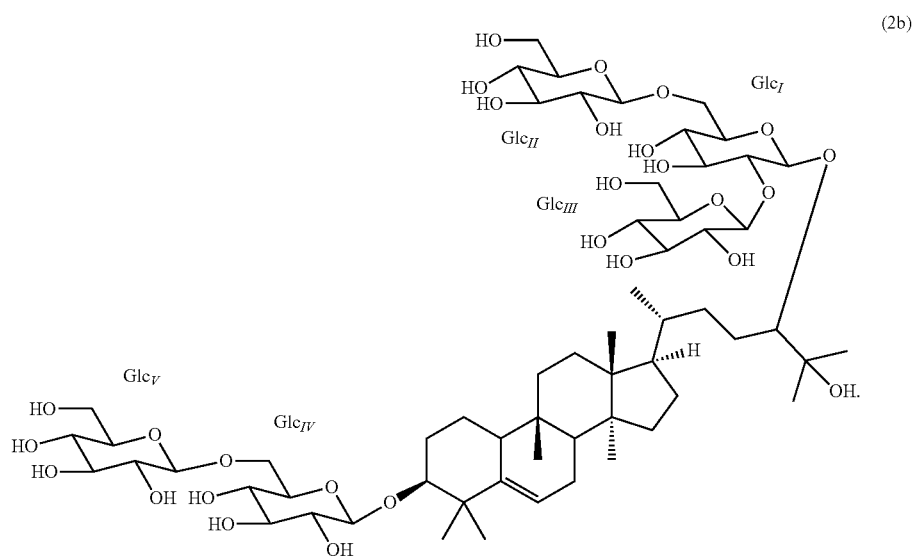

(2b)

In still another particular embodiment, the present invention is the compound of formula (3β,9β,10α, 11α,24R)-[(2-O-β-D-glucopyranosyl-6-O-β-D-glucopyranosyl-β-D-glucopyranosyl)oxy]-25-hydroxy-9-methyl-19-norlanost-5-en-24-yl-[2-O-β-D-glucopyranosyl-6-O-β-D-glucopyranosyl]-β-D-glucopyranoside) (2c):

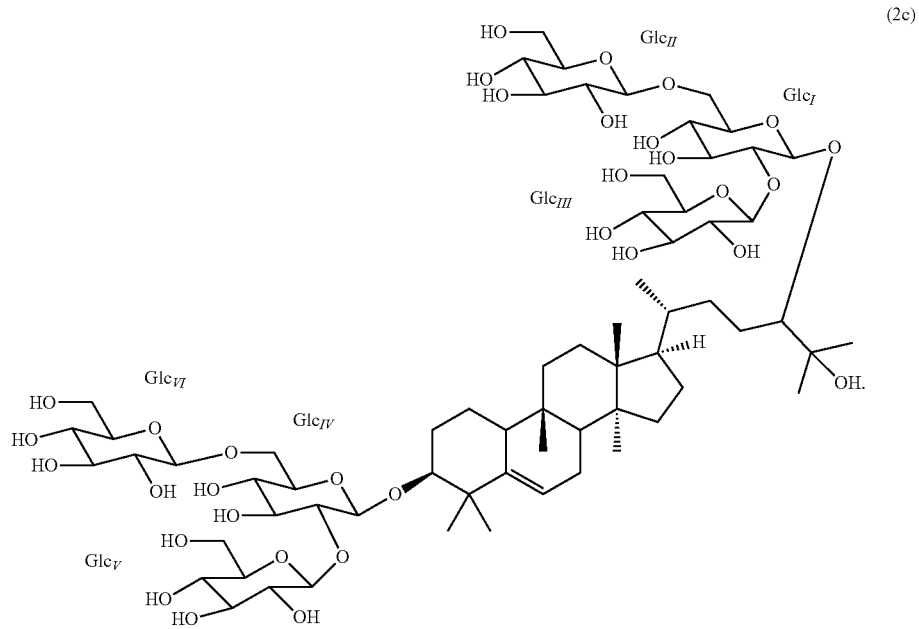

(2c)

In some embodiments, the compound of formula (1) is sweet.

In other embodiments, the compounds of formula (1) are flavor enhancers when added to a composition (e.g., a consumable) at a concentration lower than their threshold flavor recognition concentration, as described in Section II, herein.

In other embodiment, as described herein, the compounds of formula (1) are sweetness enhancers, when added to a composition (e.g., a consumable) at a concentration lower than their threshold sweetness recognition concentration, as described in Section II, herein.

II. Compositions

The present invention includes compositions comprising one or more novel mogrosides of the present invention. Such compositions include consumables, as described in further below.

In one embodiment, the composition comprises one or more novel mogrosides selected from the compounds of formula (1).

In a particular embodiment, the composition comprises two, three, four or more novel mogrosides selected from the compounds of formula (1).

In another embodiment, the composition comprises one or more novel steviol glycosides selected from the compounds of formula (2).

In a particular embodiment, the composition comprises two, three, four or more novel steviol glycosides selected from the compounds of formula (2).

In yet another embodiment, the composition comprises one or more novel mogrosides selected from the group consisting of (1a), (1b), (1c), (2a), (2b), and (2c). In a particular embodiment, the composition comprises one or more novel mogrosides selected from the group consisting of (2a), (2b), (2c) and combinations thereof.

In one embodiment, the composition comprises a compound of formula (1) provided as part of a mixture. In a particular embodiment, the mixture is selected from the group consisting of a mixture of mogrosides, a Luo han guo extract, by-products of other mogrosides' isolation and purification processes, a commercially available Luo han guo extract or any combination thereof. In one embodiment, the mixture contains a compound of formula (1) in an amount that ranges from about 1% to about 99% by weight on a dry basis, such as, for example, about 5% to about 99% by weight on a dry basis, from about 10% to about 99%, from about 20% to about 99%, from about 30% to about 99%, from about 40% to about 99%, from about 50% to about 99%, from about 60% to about 99%, from about 70% to about 99%, from about 80% to about 99% and from about 90% to about 99%. In a particular embodiment, the mixture contains a compound of formula (1) in an amount greater than about 90% by weight on a dry basis, for example, greater than about 91%, greater than about 92%, greater than about 93%, greater than about 94%, greater than about 95%, greater than about 96%, greater than about 97%, greater than about 98% and greater than about 99%.

In one embodiment, the composition comprises a compound of formula (1), provided in the form of a Luo han guo extract. The Luo han guo extract contains one or more additional mogrosides including, but not limited to, mogroside IA, mogroside IE, 11-oxomogroside IA, mogroside II A, mogroside II B, mogroside II E, 7-oxomogroside II E, mogroside III, 11-deoxymogroside III, mogroside IV, 11-oxomogroside IV A, mogroside V, 7-oxomogroside V, 11-oxomogroside V, isomogroside V, mogroside VI, mogrol, 11-oxomogrol, isomogroside, siamenoside, siamenoside I, and neomogroside.

In still another embodiment, the present invention is a composition comprising a compound of formula (1), provided as a pure compound, i.e. >99% purity on a dry basis.

The compound of formula (1) can be present in the composition in an amount effective to provide a concentration from about 1 ppm to about 10,000 ppm when the composition is added to a consumable, such as, for example, from about 1 ppm to about 4,000 ppm, from about 1 ppm to about 3,000 ppm, from about 1 ppm to about 2,000 ppm, from about 1 ppm to about 1,000 ppm. In another embodiment, a compound of formula (1) is present in the composition in an amount effective to provide a concentration from about 10 ppm to about 1,000 ppm when the composition is added to a consumable, such as, for example, from about 10 ppm to about 800 ppm, from about 50 ppm to about 800 ppm, from about 50 ppm to about 600 ppm or from about 200 ppm to about 250 ppm. In a particular embodiment, a compound of formula (1) is present in the composition in an amount effective to provide a concentration from about 300 ppm to about 600 ppm when the composition is added to a consumable.

Sweetener Compositions

In one embodiment, the present invention is a sweetener composition comprising a compound of formula (1). "Sweetener composition," as the term is used herein, refers to a composition useful to sweeten a sweetenable composition that contains at least one sweet component in combination with at least one other substance.

In one embodiment, a compound of formula (1) is the sole sweetener in the sweetener composition, i.e. a compound of formula (1) is the only compound present in the sweetener composition that provides a detectable sweetness. In another embodiment, the sweetener composition includes a compound of formula (1) is in combination with one or more sweetener compounds.

The amount of the compound of formula (1) in the sweetener composition may vary. In one embodiment, a compound of formula (1) is present in a sweetener composition in any amount to impart the desired sweetness when the sweetener composition is added to a sweetenable composition or sweetenable consumable. In a particular embodiment, the compound of formula 1 is present in a concentration above the threshold sweetness recognition concentration of the compound of formula (1).

The sweetness of a non-sucrose sweetener can also be measured against a sucrose reference by determining the non-sucrose sweetener's sucrose equivalence. Typically, taste panelists are trained to detect sweetness of reference sucrose solutions containing between 1-15% sucrose (w/v). Other non-sucrose sweeteners are then tasted at a series of dilutions to determine the concentration of the non-sucrose sweetener that is as sweet as a given percent sucrose reference. For example, if a 1% solution of a sweetener is as sweet as a 10% sucrose solution, then the sweetener is said to be 10 times as potent as sucrose.

In one embodiment, a compound of formula (1) is present in the sweetener composition in an amount effective to provide a sucrose equivalence of greater than about 10% (w/v) when the sweetener composition is added to a sweetenable composition or sweetenable consumable, such as, for example, greater than about 11%, greater than about 12%, greater than about 13% or greater than about 14%.

The amount of sucrose, and thus another measure of sweetness, in a reference solution may be described in degrees Brix (°Bx). One degree Brix is 1 gram of sucrose in 100 grams of solution and represents the strength of the solution as percentage by weight (% w/w) (strictly speaking, by mass). In one embodiment, a sweetener composition comprises a compound of formula (1) in an amount effective to provide sweetness equivalent from about 0.50 to 14 degrees Brix of sugar when present in a sweetened composition, such as, for example, from about 5 to about 11 degrees Brix, from about 4 to about 7 degrees Brix, or about 5 degrees Brix. In yet another embodiment a composition comprising a compound of formula (1) is present with at least one other sweetener in an amount effective to provide any one of the sweetness equivalents listed above.

In one embodiment, a compound of formula (1) is present in the sweetener composition in an amount effective to provide a concentration from about 1 ppm to about 10,000 ppm when the sweetener composition is added to a consumable (e.g., a beverage), such as, for example, from about 1 ppm to about 4,000 ppm, from about 1 ppm to about 3,000 ppm, from about 1 ppm to about 2,000 ppm, from about 1 ppm to about 1,000 ppm. In another embodiment, a compound of formula (1) is present in the sweetener composition in an amount effective to provide a concentration from about 10 ppm to about 1,000 ppm when the composition is added to a consumable, such as, for example, from about 10 ppm to about 800 ppm, from about 50 ppm to about 800 ppm, from about 50 ppm to about 600 ppm or from about 200 ppm to about 250 ppm. In a particular embodiment, a compound of formula (1) is present in the sweetener composition in an amount effective to provide a concentration from about 300 ppm to about 600 ppm when the sweetener composition is added to the consumable.

In some embodiments, the compound of formula (1) is present in the sweetener composition in an amount effective to provide a concentration of the compound that is above, at or below the threshold sweetener recognition level of the compound of formula (1) when the sweetener composition is added to a consumable (e.g., a beverage).

Flavor Enhancing Compositions

In one aspect, the present invention is a flavor enhancing composition comprising a compound of formula (1).

As used herein, the term "flavor enhancer compositions" refers to a composition capable of enhancing or intensifying the perception of a particular flavor in a consumable. The terms "flavor enhancing compositions" or "flavor enhancer" are synonymous with the terms "flavor potentiator," "flavor amplifier," and "flavor intensifier." Generally, the flavor enhancing composition provided herein may enhance or potentiate the taste of flavor ingredients, i.e. any substance that provides sweetness, sourness, saltiness, savoriness, bitterness, metallic taste, astringency, sweet lingering aftertaste, sweetness onset, etc. Without being bound by any theory, the flavor enhancing composition likely does not contribute any noticeable taste to the consumable to which it is added because the compound of formula (1) is present in the consumable in a concentration at or below the flavor recognition threshold concentration of the compound of formula (1).

As used herein, the term "flavor recognition threshold concentration" refers to the lowest concentration at which the particular flavor or off-taste of a component (e.g., a compound) is perceptible in a consumable. The flavor recognition threshold concentration varies for different compounds, and may be varied with respect to the individual perceiving the flavor or the particular consumable. The flavor recognition threshold concentration can be specific for a particular compound.

In one embodiment, the flavor enhancing composition comprises a compound of formula (1), wherein the compound of formula (1) is present at a concentration effective to provide a concentration of the compound (1) that is at or below the threshold flavor recognition concentration of the compound of formula (1) when the flavor enhancing composition is added to a consumable.

In a particular embodiment, compound of formula (1) is present in the flavor-enhancing composition at a concentration effective to provide a concentration of the compound of formula (1) that is below the threshold flavor recognition concentration of the compound of formula (1) when the flavor-enhancing composition is added to a consumable.

In certain embodiment, the compound of formula (1) is present in the flavor-enhancing composition in a concentration effective to provide a concentration of the compound of formula (1) that is at least about 1%, at least about 5%, at least about 10%, at least about 15%, at least about 20%, at least about 25%, at least about 30%, at least about 35%, at least about 40%, at least about 45% or at least about 50% or more below the threshold flavor recognition concentration of the compound of formula (1) when the flavor-enhancing composition is added to a consumable.

In some embodiments, a compound of formula (1) is present in the composition in an amount that, when added to the consumable, will provide a concentration of the compound of formula (1) ranging from about 0.5 ppm to about 1000 ppm. For example, the compound of formula (1) is present in the composition in an amount that, when added to the consumable, will provide a concentration of the compound of formula (1) in an amount ranging from about 1 ppm to about 300 ppm, from about 0.1 ppm to about 75 ppm, or from about 500 ppm to about 3,000 ppm.

A person of skill in the art will be able to select the concentration of compound of formula (1) in the flavor enhancing composition so that it may impart an enhanced flavor to a consumable comprising at least one flavor ingredient. For example, a skilled artisan may select a concentration for compound of formula (1) in the flavor enhancing composition so that the flavor enhancing composition and/or the compound of formula (1) does not impart any perceptible flavor to a consumable when the flavor enhancing composition is added thereto.

In one embodiment, addition of the flavor enhancing composition increases the detected flavor of the at least one flavor ingredient in the consumable compared to the detected flavor of the same ingredient in the consumable in the absence of the flavor enhancer.

Suitable flavor ingredients include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Dohler™ Natural Flavoring Sweetness Enhancer K14323 (Dohler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

In another embodiment, the flavor enhancer composition comprising a compound of formula (1) enhances flavors (either individual flavors or the overall flavor) when added to the consumable. These flavors include, but are not limited to, fruit flavors, including tropical fruit flavors, and vanilla-caramel type flavors.

Alternatively, the compound of formula (1) may be added directly to the consumable, i.e., not provided in the form of a composition, to enhance flavor. In this embodiment, the compound of formula (1) is a sweetness enhancer and it is added to the consumable at a concentration at or below the threshold flavor recognition concentration of the compound of formula (1).

In a particular embodiment, the flavor enhancing composition is a sweetness enhancing composition. As used herein, the term "sweetness enhancing composition" refers to a composition capable of enhancing or intensifying the perception of sweet taste of a consumable, such as a beverage. The term "sweetness enhancer" is synonymous with the terms "sweet taste potentiator," "sweetness potentiator," "sweetness amplifier," and "sweetness intensifier."

Generally, the sweetness enhancing composition provided herein may enhance or potentiate the taste of a sweetener, i.e. any substance that provides sweetness. Without being bound by any theory, the sweetness enhancing composition likely does not contribute any noticeable sweet taste to the consumable to which it is added because the concentration of the compound of formula (1) in the consumable after the sweetness enhancing composition is added is at a concentration at or below the sweetness recognition threshold concentration of the compound of formula (1).

The term "sweetness recognition threshold concentration," as generally used herein, is the lowest known concentration of a sweet compound that is perceivable by the human sense of taste. Generally, the sweetness enhancing composition of the present invention may enhance or potentiate the sweet taste of a consumable without providing any noticeable sweet taste itself because the concentration of the compound of formula (1) in the sweetness enhancing composition is at or below its sweetness recognition threshold concentration, either in the sweetness enhancing compositions, the consumable after the sweetness enhancing composition has been added, or both. The sweetness recognition threshold concentration is specific for a particular compound, and can vary based on temperature, matrix, ingredients and/or flavor system.

In one embodiment, the flavor enhancing composition comprises a compound of formula (1), wherein the compound of formula (1) is present at a concentration effective to provide a concentration of the compound (1) that is at or below the threshold sweetness recognition concentration of the compound of formula (1) when the sweetness enhancing composition is added to a consumable.

In a particular embodiment, compound of formula (1) is present in the flavor-enhancing composition at a concentration effective to provide a concentration of the compound of formula (1) that is below the threshold sweetness recognition concentration of the compound of formula (1) when the sweetness enhancing composition is added to a consumable.

In certain embodiment, the compound of formula (1) is present in the sweetness enhancing composition in a concentration effective to provide a concentration of the compound of formula (1) that is at least about 1%, at least about 5%, at least about 10%, at least about 15%, at least about 20%, at least about 25%, at least about 30%, at least about 35%, at least about 40%, at least about 45% or at least about 50% or more below the threshold sweetness recognition concentration of the compound of formula (1) when the sweetness enhancing composition is added to a consumable.

In some embodiments, a compound of formula (1) is present in the composition in an amount that, when added to the consumable, will provide a concentration of the compound of formula (1) ranging from about 0.5 ppm to about 1000 ppm. For example, the compound of formula (1) is present in the composition in an amount that, when added to the consumable, will provide a concentration of the compound of formula (1) in an amount ranging from about 1 ppm to about 300 ppm, from about 0.1 ppm to about 75 ppm, or from about 500 ppm to about 3,000 ppm.

In some embodiments, the at least one sweetness enhancer is present in an amount ranging from about 0.5 ppm to about 1000 ppm. For example, the at least one sweetness enhancer may be present in an amount ranging from about 1 ppm to about 300 ppm, from about 0.1 ppm to about 75 ppm, or from about 500 ppm to about 3,000 ppm.

Alternatively, the compound of formula (1) may be added directly to the consumable, i.e., not provided in the form of a composition, to enhance sweetness. In this embodiment, the compound of formula (1) is a sweetness enhancer and it is added to the consumable at a concentration at or below the sweetness recognition threshold concentration of the compound of formula (1).

The sweetness of a given composition is typically measured with reference to a solution of sucrose. See generally "A Systematic Study of Concentration-Response Relationships of Sweeteners," G. E. DuBois, D. E. Walters, S. S. Schiffman, Z. S. Warwick, B. J. Booth, S. D. Pecore, K. Gibes, B. T. Can, and L. M. Brands, in *Sweeteners: Discovery, Molecular Design and Chemoreception*, D. E. Walters, F. T. Orthoefer, and G. E. DuBois, Eds., American Chemical Society, Washington, D.C. (1991), pp 261-276.

The sweetness of a non-sucrose sweetener can be measured against a sucrose reference by determining the non-sucrose sweetener's sucrose equivalence. Typically, taste panelists are trained to detect sweetness of reference sucrose solutions containing between 1-15% sucrose (w/v). Other non-sucrose sweeteners are then tasted at a series of dilutions to determine the concentration of the non-sucrose sweetener that is as sweet as a given percent sucrose reference. For example, if a 1% solution of a sweetener is as sweet as a 10% sucrose solution, then the sweetener is said to be 10 times as potent as sucrose, and has 10% sucrose equivalence.

In a further embodiment, the sweetness enhancing composition comprises a compound of formula (1) and at least one sweetener, wherein the sweetness enhancer is present in a consumable to which the sweetness enhancing composition is added at a concentration at or below the sweetness recognition threshold concentration of the compound of formula (1). In a particular embodiment, the sweetness enhancing composition comprises a compound of formula (1) and at least one sweetener, wherein the sweetness enhancer is present in a consumable to which the sweetness enhancing composition is added at a concentration below the sweetness recognition threshold concentration of the compound of formula (1).

It is contemplated that the composition can include one or more sweetness enhancers. In one embodiment, the composition can include one sweetness enhancer. In other embodiments, the composition can include two or more sweetness enhancers. In embodiments where two or more sweetness enhancers are utilized, each sweetness enhancer should be present below its respective sweetness recognition threshold concentration.

In some embodiments, a sweetness enhancer that is the compound of formula (1) is combined with one or more other sweetness enhancers selected from, but not limited to, the group consisting of 2-hydroxybenzoic acid, 3-hydroxybenzoic acid, 4-hydroxybenzoic acid, 2,4-dihydroxybenzoic acid, 3,4-dihydroxybenzoic acid, 2,5-dihydroxybenzoic acid, 2,6-dihydroxybenzoic acid, 2,3,4-trihydroxybenzoic acid, 2,4,6-trihydroxybenzoic acid, 3-aminobenzoic acid, 4-aminobenzoic acid, FEMA GRAS enhancer 4469, FEMA GRAS enhancer 4701, FEMA GRAS enhancer 4720, FEMA GRAS enhancer 4774, FEMA GRAS enhancer 4708, FEMA GRAS enhancer 4728, FEMA GRAS enhancer 4601 and combinations thereof.

In another embodiment, suitable sweeteners are selected from, but not limited to, the group consisting of sucrose, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, fucose, rhamnose, arabinose, turanose, sialose, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, dulcoside A, dulcoside B, rubusoside, stevia, stevioside, mogroside IV, mogroside V, Luo han guo, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside and cyclocarioside I, sugar alcohols such as erythritol, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof.

In one embodiment, the sweetener is a caloric sweetener or mixture of caloric sweeteners. In another embodiment, the caloric sweetener is selected from sucrose, fructose, glucose, high fructose corn/starch syrup, a beet sugar, a cane sugar, and combinations thereof.

In another embodiment, the sweetener is a rare sugar selected from D-psicose, D-allose, L-ribose, D-tagatose, L-glucose, L-fucose, L-arabinose, turanose and combinations thereof.

In yet another embodiment, the sweetener is a non-caloric sweetener or mixture of non-caloric sweeteners. In one example, the non-caloric sweetener is a natural high-potency sweetener. As used herein, the phrase "natural high potency sweetener" refers to any composition which is not found naturally in nature and characteristically has a sweetness potency greater than sucrose, fructose, or glucose, yet has less calories. The natural high potency sweetener can be provided as a pure compound or, alternatively, as part of an extract.

In yet another example, the non-caloric sweetener is a synthetic high-potency sweetener. As used herein, the phrase "synthetic sweetener" refers to any composition which is not found naturally in nature and characteristically has a sweetness potency greater than sucrose, fructose, or glucose, yet has less calories.

In one embodiment, addition of the sweetness enhancer increases the detected sucrose equivalence of the at least one sweetener in a consumable compared to the sucrose equivalence of the same consumable in the absence of the sweetness enhancer.

In a particular embodiment, the consumable is a beverage. The beverage comprises at a sweetness enhancer that is a compound of formula (1) and at least one sweetener, wherein the sweetness enhancer is present in a concentration below the sweetness recognition threshold. In a particular embodiment, the detected sucrose equivalence is increased from about 0.2% to about 5.0%, such as, for example, about 1%, about 2%, about 3%, about 4% or about 5%.

The sweetener can be any natural or synthetic sweetener provided herein. In a particular embodiment, the sweetener is a calorie-providing carbohydrate sweetener. Accordingly, incorporation of the sweetness enhancer thereby reduces the quantity of the calorie-providing carbohydrate sweetener that must be used in a given consumable, thereby allowing the preparation of reduced-calorie consumables.

The compositions can be customized to provide the desired calorie content. For example, compositions can be "full-calorie", such that they impart the desired sweetness when added to a consumable (such as, for example, a beverage) and have about 120 calories per 8 oz serving. Alternatively, compositions can be "mid-calorie", such that they impart the desired sweetness when added to a consumable (such as, for example, as beverage) and have less than about 60 calories per 8 oz serving. In other embodiments, compositions can be "low-calorie", such that they impart the desired sweetness when added to a consumable (such as, for example, as beverage) and have less than 40 calories per 8 oz serving. In still other embodiments, the compositions can be "zero-calorie", such that they impart the desired sweetness when added to a consumable (such as, for example, a beverage) and have less than 5 calories per 8 oz. serving.

Additives

The compositions may comprise, in addition to a compound of formula (1), one or more additives, e.g. sweetener compositions and flavor enhanced compositions, can optionally include additional additives, detailed herein below. In some embodiments, the composition contains additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, weighing agents, gums, antioxidants, colorants, flavonoids, alcohols, polymers and combinations thereof. In some embodiments, the additives act to improve the temporal and flavor profile of the sweetener to provide a sweetener composition with a taste similar to sucrose.

In one embodiment, the compositions further comprise contain one or more polyols. The term "polyol", as used herein, refers to a molecule that contains more than one hydroxyl group. A polyol may be a diol, a triol, or a tetraol which contains 2, 3, and 4 hydroxyl groups respectively. A polyol also may contain more than 4 hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group.

Non-limiting examples of polyols in some embodiments include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect the taste of the compositions.

In certain embodiments, the polyol is present in the compositions in an amount effective to provide a concentration from about 100 ppm to about 250,000 ppm when present in a consumable, such as, for example, a beverage. In other embodiments, the polyol is present in the compositions in an amount effective to provide a concentration from about 400 ppm to about 80,000 ppm when present in a consumable, such as, for example, from about 5,000 ppm to about 40,000 ppm.

In other embodiments, a compound of formula (1) is present in the composition with the polyol in a weight ratio from about 1:1 to about 1:800, such as, for example, from about 1:4 to about 1:800, from about 1:20 to about 1:600, from about 1:50 to about 1:300 or from about 1:75 to about 1:150.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid ($\alpha$-, $\beta$-, and/or $\delta$-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be $\alpha$-, $\beta$-, $\gamma$- and/or $\delta$-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-$\alpha$-lysine or poly-L-$\epsilon$-lysine), poly-L-ornithine (e.g., poly-L-$\alpha$-ornithine or poly-L-$\epsilon$-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be $\alpha$-, $\beta$-, $\gamma$-, $\delta$-, and $\epsilon$-isomers if appropriate. Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-α-lysine with a MW of 1,500, MW of 6,000, MW of 25,200, MW of 63,000, MW of 83,000, or MW of 300,000.

In particular embodiments, the amino acid is present in the composition in an amount effective to provide a concentration from about 10 ppm to about 50,000 ppm when present in a consumable, such as, for example, a beverage. In another embodiment, the amino acid is present in the composition in an amount effective to provide a concentration from about 1,000 ppm to about 10,000 ppm when present in a consumable, such as, for example, from about 2,500 ppm to about 5,000 ppm or from about 250 ppm to about 7,500 ppm.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

The nucleotide is present in the composition in an amount effective to provide a concentration from about 5 ppm to about 1,000 ppm when present in consumable, such as, for example, a beverage.

Suitable organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato. In particular embodiments, the organic acid additive is present in the composition in an amount effective to provide a concentration from about 10 ppm to about 5,000 ppm when present in a consumable, such as, for example, a beverage.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

The inorganic acid additive is present in the composition in an amount effective to provide a concentration from about 25 ppm to about 25,000 ppm when present in a consumable, such as, for example, a beverage.

Suitable bitter compound additives include, but are not limited to, caffeine, quinine, urea, bitter orange oil, naringin, quassia, and salts thereof.

The bitter compound is present in the composition in an amount effective to provide a concentration from about 25 ppm to about 25,000 ppm when present in a consumable, such as, for example, a beverage.

Suitable flavorants and flavoring ingredient additives include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Dohler™ Natural Flavoring Sweetness Enhancer K14323 (Dohler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

The flavorant is present in the composition in an amount effective to provide a concentration from about 0.1 ppm to about 4,000 ppm when present in a consumable, such as, for example, a beverage.

Suitable polymer additives include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

The polymer is present in the composition in an amount effective to provide a concentration from about 30 ppm to about 2,000 ppm when present in a consumable, such as, for example, a beverage.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

The protein hydrolysate is present in the composition in an amount effective to provide a concentration from about 200 ppm to about 50,000 ppm when present in a consumable, such as, for example, a beverage.

Suitable surfactant additives include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

The surfactant additive is present in the composition in an amount effective to provide a concentration from about 30 ppm to about 2,000 ppm when present in a consumable, such as, for example, a beverage.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

The flavonoid additive is present in the composition in an amount effective to provide a concentration from about 0.1 ppm to about 1,000 ppm when present in a consumable, such as, for example, a beverage.

Suitable alcohol additives include, but are not limited to, ethanol. In particular embodiments, the alcohol additive is present in the composition in an amount effective to provide a concentration from about 625 ppm to about 10,000 ppm when present in a consumable, such as, for example, a beverage.

Suitable astringent compound additives include, but are not limited to, tannic acid, europium chloride (EuCl$_3$), gadolinium chloride (GdCl$_3$), terbium chloride (TbCl$_3$), alum, tannic acid, and polyphenols (e.g., tea polyphenols). The astringent additive is present in the composition in an amount effective to provide a concentration from about 10 ppm to about 5,000 ppm when present in a consumable, such as, for example, a beverage.

Functional Ingredients

The compositions provided herein can also contain one or more functional ingredients, which provide a real or perceived heath benefit to the composition. Functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

Saponin

In certain embodiments, the functional ingredient is at least one saponin. As used herein, the at least one saponin may comprise a single saponin or a plurality of saponins as a functional ingredient for the composition provided herein. Generally, according to particular embodiments of this invention, the at least one saponin is present in the composition in an amount sufficient to promote health and wellness.

Saponins are glycosidic natural plant products comprising an aglycone ring structure and one or more sugar moieties. The combination of the nonpolar aglycone and the water soluble sugar moiety gives saponins surfactant properties, which allow them to form a foam when shaken in an aqueous solution.

The saponins are grouped together based on several common properties. In particular, saponins are surfactants which display hemolytic activity and form complexes with cholesterol. Although saponins share these properties, they are structurally diverse. The types of aglycone ring structures forming the ring structure in saponins can vary greatly. Non-limiting examples of the types of aglycone ring structures in saponin for use in particular embodiments of the invention include steroids, triterpenoids, and steroidal alkaloids. Non-limiting examples of specific aglycone ring structures for use in particular embodiments of the invention include soyasapogenol A, soyasapogenol B and soyasapogenol E. The number and type of sugar moieties attached to the aglycone ring structure can also vary greatly. Non-limiting examples of sugar moieties for use in particular embodiments of the invention include glucose, galactose, glucuronic acid, xylose, rhamnose, and methylpentose moieties. Non-limiting examples of specific saponins for use in particular embodiments of the invention include group A acetyl saponin, group B acetyl saponin, and group E acetyl saponin.

Saponins can be found in a large variety of plants and plant products, and are especially prevalent in plant skins and barks where they form a waxy protective coating. Several common sources of saponins include soybeans, which have approximately 5% saponin content by dry weight, soapwort plants (*Saponaria*), the root of which was used historically as soap, as well as alfalfa, aloe, asparagus, grapes, chickpeas, yucca, and various other beans and weeds. Saponins may be obtained from these sources by using extraction techniques well known to those of ordinary skill in the art. A description of conventional extraction techniques can be found in U.S. Pat. Appl. No. 2005/0123662, the disclosure of which is expressly incorporated by reference.

Antioxidant

In certain embodiments, the functional ingredient is at least one antioxidant. As used herein, the at least one antioxidant may comprise a single antioxidant or a plurality of antioxidants as a functional ingredient for the compositions provided herein. Generally, according to particular embodiments of this invention, the at least one antioxidant is present in the composition in an amount sufficient to promote health and wellness.

As used herein "antioxidant" refers to any substance which inhibits, suppresses, or reduces oxidative damage to cells and biomolecules. Without being bound by theory, it is believed that antioxidants inhibit, suppress, or reduce oxidative damage to cells or biomolecules by stabilizing free radicals before they can cause harmful reactions. As such, antioxidants may prevent or postpone the onset of some degenerative diseases.

Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-α-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains, or cereal grains.

Particular antioxidants belong to the class of phytonutrients called polyphenols (also known as "polyphenolics"), which are a group of chemical substances found in plants, characterized by the presence of more than one phenol group per molecule. A variety of health benefits may be derived from polyphenols, including prevention of cancer, heart disease, and chronic inflammatory disease and improved mental strength and physical strength, for example. Suitable polyphenols for embodiments of this invention include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

In particular embodiments, the antioxidant is a catechin such as, for example, epigallocatechin gallate (EGCG). Suitable sources of catechins for embodiments of this invention include, but are not limited to, green tea, white tea, black tea, oolong tea, chocolate, cocoa, red wine, grape seed, red grape skin, purple grape skin, red grape juice, purple grape juice, berries, pycnogenol, and red apple peel.

In some embodiments, the antioxidant is chosen from proanthocyanidins, procyanidins or combinations thereof. Suitable sources of proanthocyanidins and procyanidins for embodiments of this invention include, but are not limited to, red grapes, purple grapes, cocoa, chocolate, grape seeds, red wine, cacao beans, cranberry, apple peel, plum, blueberry, black currants, choke berry, green tea, sorghum, cinnamon, barley, red kidney bean, pinto bean, hops, almonds, hazelnuts, pecans, pistachio, pycnogenol, and colorful berries.

In particular embodiments, the antioxidant is an anthocyanin. Suitable sources of anthocyanins for embodiments of this invention include, but are not limited to, red berries, blueberries, bilberry, cranberry, raspberry, cherry, pomegranate, strawberry, elderberry, choke berry, red grape skin, purple grape skin, grape seed, red wine, black currant, red currant, cocoa, plum, apple peel, peach, red pear, red cabbage, red onion, red orange, and blackberries.

In some embodiments, the antioxidant is chosen from quercetin, rutin or combinations thereof. Suitable sources of quercetin and rutin for embodiments of this invention include, but are not limited to, red apples, onions, kale, bog whortleberry, lingonberrys, chokeberry, cranberry, blackberry, blueberry, strawberry, raspberry, black currant, green tea, black tea, plum, apricot, parsley, leek, broccoli, chili pepper, berry wine, and ginkgo.

In some embodiments, the antioxidant is reservatrol. Suitable sources of reservatrol for embodiments of this invention include, but are not limited to, red grapes, peanuts, cranberry, blueberry, bilberry, mulberry, Japanese Itadori tea, and red wine.

In particular embodiments, the antioxidant is an isoflavone. Suitable sources of isoflavones for embodiments of this invention include, but are not limited to, soy beans, soy products, legumes, alfalfa spouts, chickpeas, peanuts, and red clover.

In some embodiments, the antioxidant is curcumin. Suitable sources of curcumin for embodiments of this invention include, but are not limited to, turmeric and mustard.

In particular embodiments, the antioxidant is chosen from punicalagin, ellagitannin or combinations thereof. Suitable sources of punicalagin and ellagitannin for embodiments of this invention include, but are not limited to, pomegranate, raspberry, strawberry, walnut, and oak-aged red wine.

In some embodiments, the antioxidant is a citrus flavonoid, such as hesperidin or naringin. Suitable sources of citrus flavonoids, such as hesperidin or naringin, for embodiments of this invention include, but are not limited to, oranges, grapefruits, and citrus juices.

In particular embodiments, the antioxidant is chlorogenic acid. Suitable sources of chlorogenic acid for embodiments of this invention include, but are not limited to, green coffee, yerba mate, red wine, grape seed, red grape skin, purple grape skin, red grape juice, purple grape juice, apple juice, cranberry, pomegranate, blueberry, strawberry, sunflower, Echinacea, pycnogenol, and apple peel.

Dietary Fiber

In certain embodiments, the functional ingredient is at least one dietary fiber source. As used herein, the at least one dietary fiber source may comprise a single dietary fiber source or a plurality of dietary fiber sources as a functional ingredient for the compositions provided herein. Generally, according to particular embodiments of this invention, the at least one dietary fiber source is present in the composition in an amount sufficient to promote health and wellness.

Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins, and combinations thereof.

Polysaccharides are complex carbohydrates composed of monosaccharides joined by glycosidic linkages. Non-starch polysaccharides are bonded with β-linkages, which humans are unable to digest due to a lack of an enzyme to break the β-linkages. Conversely, digestible starch polysaccharides generally comprise α(1-4) linkages.

Lignin is a large, highly branched and cross-linked polymer based on oxygenated phenylpropane units. Cellulose is a linear polymer of glucose molecules joined by a β(1-4) linkage, which mammalian amylases are unable to hydrolyze. Methylcellulose is a methyl ester of cellulose that is often used in foodstuffs as a thickener, and emulsifier. It is commercially available (e.g., Citrucel by GlaxoSmithKline, Celevac by Shire Pharmaceuticals). Hemicelluloses are highly branched polymers consisting mainly of glucurono- and 4-O-methylglucuroxylans. β-Glucans are mixed-linkage (1-3), (1-4) β-D-glucose polymers found primarily in cereals, such as oats and barley. Pectins, such as beta pectin, are a group of polysaccharides composed primarily of D-galacturonic acid, which is methoxylated to variable degrees.

Gums and mucilages represent a broad array of different branched structures. Guar gum, derived from the ground endosperm of the guar seed, is a galactomannan. Guar gum is commercially available (e.g., Benefiber by Novartis AG). Other gums, such as gum arabic and pectins, have still different structures. Still other gums include xanthan gum, gellan gum, tara gum, psylium seed husk gum, and locust been gum.

Waxes are esters of ethylene glycol and two fatty acids, generally occurring as a hydrophobic liquid that is insoluble in water.

Inulins comprise naturally occurring oligosaccharides belonging to a class of carbohydrates known as fructans. They generally are comprised of fructose units joined by β(2-1) glycosidic linkages with a terminal glucose unit. Oligosaccharides are saccharide polymers containing typically three to six component sugars. They are generally found either O- or N-linked to compatible amino acid side chains in proteins or to lipid molecules. Fructooligosaccharides are oligosaccharides consisting of short chains of fructose molecules.

Food sources of dietary fiber include, but are not limited to, grains, legumes, fruits, and vegetables. Grains providing dietary fiber include, but are not limited to, oats, rye, barley, wheat. Legumes providing fiber include, but are not limited to, peas and beans such as soybeans. Fruits and vegetables providing a source of fiber include, but are not limited to, apples, oranges, pears, bananas, berries, tomatoes, green beans, broccoli, cauliflower, carrots, potatoes, celery. Plant foods such as bran, nuts, and seeds (such as flax seeds) are also sources of dietary fiber. Parts of plants providing dietary fiber include, but are not limited to, the stems, roots, leaves, seeds, pulp, and skin.

Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

Sources of dietary fiber often are divided into categories of soluble and insoluble fiber based on their solubility in water. Both soluble and insoluble fibers are found in plant foods to varying degrees depending upon the characteristics of the plant. Although insoluble in water, insoluble fiber has passive hydrophilic properties that help increase bulk, soften stools, and shorten transit time of fecal solids through the intestinal tract.

Unlike insoluble fiber, soluble fiber readily dissolves in water. Soluble fiber undergoes active metabolic processing via fermentation in the colon, increasing the colonic microflora and thereby increasing the mass of fecal solids. Fermentation of fibers by colonic bacteria also yields end-products with significant health benefits. For example, fermentation of the food masses produces gases and short-chain fatty acids. Acids produced during fermentation include butyric, acetic, propionic, and valeric acids that have various beneficial properties such as stabilizing blood glucose levels by acting on pancreatic insulin release and providing liver control by glycogen breakdown. In addition, fiber fermentation may reduce atherosclerosis by lowering cholesterol synthesis by the liver and reducing blood levels of LDL and triglycerides. The acids produced during fermentation lower colonic pH, thereby protecting the colon lining from cancer polyp formation. The lower colonic pH also increases mineral absorption, improves the barrier properties of the colonic mucosal layer, and inhibits inflammatory and adhesion irritants. Fermentation of fibers also may benefit the immune system by stimulating production of T-helper cells, antibodies, leukocytes, splenocytes, cytokinins and lymphocytes.

Fatty Acid

In certain embodiments, the functional ingredient is at least one fatty acid. As used herein, the at least one fatty acid may be single fatty acid or a plurality of fatty acids as a functional ingredient for the compositions provided herein. Generally, according to particular embodiments of this invention, the at least one fatty acid is present in the composition in an amount sufficient to promote health and wellness.

As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, Md.), OmegaPure (from Omega Protein, Houston, Tex.), Marinol C-38 (from Lipid Nutrition, Channahon, Ill.), Bonito oil and MEG-3 (from Ocean Nutrition, Dartmouth, NS), Evogel (from Symrise, Holzminden, Germany), Marine Oil, from tuna or salmon (from Arista Wilton, Conn.), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosadienoic acid, adrenic acid, docosapentaenoic acid and combinations thereof.

Suitable esterified fatty acids for embodiments of the present invention may include, but are not limited to, monoacylglycerols containing omega-3 and/or omega-6 fatty acids, diacylglycerols containing omega-3 and/or omega-6 fatty acids, or triacylglycerols containing omega-3 and/or omega-6 fatty acids and combinations thereof.

Vitamin

In certain embodiments, the functional ingredient is at least one vitamin.

As used herein, the at least one vitamin may be single vitamin or a plurality of vitamins as a functional ingredient for the compositions provided herein. Generally, according to particular embodiments of this invention, the at least one vitamin is present in the composition in an amount sufficient to promote health and wellness.

Vitamins are organic compounds that the human body needs in small quantities for normal functioning. The body uses vitamins without breaking them down, unlike other nutrients such as carbohydrates and proteins. To date, thirteen vitamins have been recognized, and one or more can be used in the compositions herein. Suitable vitamins include, vitamin A, vitamin D, vitamin E, vitamin K, vitamin B1, vitamin B2, vitamin B3, vitamin B5, vitamin B6, vitamin B7, vitamin B9, vitamin B12, and vitamin C. Many of vitamins also have alternative chemical names, non-limiting examples of which are provided below.

| Vitamin | Alternative names |
| --- | --- |
| Vitamin A | Retinol |
| | Retinaldehyde |
| | Retinoic acid |
| | Retinoids |
| | Retinal |
| | Retinoic ester |
| Vitamin D (vitamins D1-D5) | Calciferol |
| | Cholecalciferol |
| | Lumisterol |
| | Ergocalciferol |
| | Dihydrotachysterol |
| | 7-dehydrocholesterol |
| Vitamin E | Tocopherol |
| | Tocotrienol |
| Vitamin K | Phylloquinone |
| | Naphthoquinone |
| Vitamin B1 | Thiamin |
| Vitamin B2 | Riboflavin |
| | Vitamin G |

-continued

| Vitamin | Alternative names |
| --- | --- |
| Vitamin B3 | Niacin |
| | Nicotinic acid |
| | Vitamin PP |
| Vitamin B5 | Pantothenic acid |
| Vitamin B6 | Pyridoxine |
| | Pyridoxal |
| | Pyridoxamine |
| Vitamin B7 | Biotin |
| | Vitamin H |
| Vitamin B9 | Folic acid |
| | Folate |
| | Folacin |
| | Vitamin M |
| | Pteroyl-L-glutamic acid |
| Vitamin B12 | Cobalamin |
| | Cyanocobalamin |
| Vitamin C | Ascorbic acid |

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methyl-methionine. As used herein, the term vitamin includes pseudo-vitamins.

In some embodiments, the vitamin is a fat-soluble vitamin chosen from vitamin A, D, E, K and combinations thereof.

In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof.

Glucosamine

In certain embodiments, the functional ingredient is glucosamine.

Generally, according to particular embodiments of this invention, glucosamine is present in the compositions in an amount sufficient to promote health and wellness.

Glucosamine, also called chitosamine, is an amino sugar that is believed to be an important precursor in the biochemical synthesis of glycosylated proteins and lipids. D-glucosamine occurs naturally in the cartilage in the form of glucosamine-6-phosphate, which is synthesized from fructose-6-phosphate and glutamine. However, glucosamine also is available in other forms, non-limiting examples of which include glucosamine hydrochloride, glucosamine sulfate, N-acetyl-glucosamine, or any other salt forms or combinations thereof. Glucosamine may be obtained by acid hydrolysis of the shells of lobsters, crabs, shrimps, or prawns using methods well known to those of ordinary skill in the art. In a particular embodiment, glucosamine may be derived from fungal biomass containing chitin, as described in U.S. Patent Publication No. 2006/0172392.

The compositions can further comprise chondroitin sulfate.

Mineral

In certain embodiments, the functional ingredient is at least one mineral.

As used herein, the at least one mineral may be single mineral or a plurality of minerals as a functional ingredient for the compositions provided herein. Generally, according to particular embodiments of this invention, the at least one mineral is present in the composition in an amount sufficient to promote health and wellness.

Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In particular embodiments of this invention, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In other particular embodiments of this invention, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in a particular embodiment the minerals may be in their ionic form, having either a positive or negative charge. In another particular embodiment the minerals may be in their molecular form. For example, sulfur and phosphorous often are found naturally as sulfates, sulfides, and phosphates.

Preservative

In certain embodiments, the functional ingredient is at least one preservative.

As used herein, the at least one preservative may be single preservative or a plurality of preservatives as a functional ingredient for the compositions provided herein. Generally, according to particular embodiments of this invention, the at least one preservative is present in the composition in an amount sufficient to promote health and wellness.

In particular embodiments of this invention, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone.

According to a particular embodiment, the preservative is a sulfite. Sulfites include, but are not limited to, sulfur dioxide, sodium bisulfite, and potassium hydrogen sulfite.

According to another particular embodiment, the preservative is a propionate. Propionates include, but are not limited to, propionic acid, calcium propionate, and sodium propionate.

According to yet another particular embodiment, the preservative is a benzoate. Benzoates include, but are not limited to, sodium benzoate and benzoic acid.

In another particular embodiment, the preservative is a sorbate. Sorbates include, but are not limited to, potassium sorbate, sodium sorbate, calcium sorbate, and sorbic acid.

In still another particular embodiment, the preservative is a nitrate and/or nitrite. Nitrates and nitrites include, but are not limited to, sodium nitrate and sodium nitrite.

In yet another particular embodiment, the at least one preservative is a bacteriocin, such as, for example, nisin.

In another particular embodiment, the preservative is ethanol.

In still another particular embodiment, the preservative is ozone.

Non-limiting examples of antienzymatics suitable for use as preservatives in particular embodiments of the invention include ascorbic acid, citric acid, and metal chelating agents such as ethylenediaminetetraacetic acid (EDTA).

Hydration Agent

In certain embodiments, the functional ingredient is at least one hydration agent.

As used herein, the at least one hydration agent may be single hydration agent or a plurality of hydration agents as a functional ingredient for the compositions provided herein. Generally, according to particular embodiments of this invention, the at least one hydration agent is present in the composition in an amount sufficient to promote health and wellness.

Hydration products help the body to replace fluids that are lost through excretion. For example, fluid is lost as sweat in order to regulate body temperature, as urine in order to excrete waste substances, and as water vapor in order to exchange gases in the lungs. Fluid loss can also occur due to a wide range of external causes, non-limiting examples of which include physical activity, exposure to dry air, diarrhea, vomiting, hyperthermia, shock, blood loss, and hypotension. Diseases causing fluid loss include diabetes, cholera, gastroenteritis, shigellosis, and yellow fever. Forms of malnutrition that cause fluid loss include the excessive consumption of alcohol, electrolyte imbalance, fasting, and rapid weight loss.

In a particular embodiment, the hydration product is a composition that helps the body replace fluids that are lost during exercise. Accordingly, in a particular embodiment, the hydration product is an electrolyte, non-limiting examples of which include sodium, potassium, calcium, magnesium, chloride, phosphate, bicarbonate, and combinations thereof. Suitable electrolytes for use in particular embodiments of this invention are also described in U.S. Pat. No. 5,681,569, the disclosure of which is expressly incorporated herein by reference. In particular embodiments, the electrolytes are obtained from their corresponding water-soluble salts. Non-limiting examples of salts for use in particular embodiments include chlorides, carbonates, sulfates, acetates, bicarbonates, citrates, phosphates, hydrogen phosphates, tartrates, sorbates, citrates, benzoates, or combinations thereof. In other embodiments, the electrolytes are provided by juice, fruit extracts, vegetable extracts, tea, or teas extracts.

In particular embodiments of this invention, the hydration product is a carbohydrate to supplement energy stores burned by muscles. Suitable carbohydrates for use in particular embodiments of this invention are described in U.S. Pat. Nos. 4,312,856, 4,853,237, 5,681,569, and 6,989,171, the disclosures of which are expressly incorporated herein by reference. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration product is a glycerol solution to enhance exercise endurance. The ingestion of a glycerol containing solution has been shown to provide beneficial physiological effects, such as expanded blood volume, lower heart rate, and lower rectal temperature.

Probiotics/Prebiotics

In certain embodiments, the functional ingredient is chosen from at least one probiotic, prebiotic and combination thereof.

As used herein, the at least one probiotic or prebiotic may be single probiotic or prebiotic or a plurality of probiotics or prebiotics as a functional ingredient for the compositions provided herein. Generally, according to particular embodiments of this invention, the at least one probiotic, prebiotic or combination thereof is present in the composition in an amount sufficient to promote health and wellness.

Probiotics, in accordance with the teachings of this invention, comprise microorganisms that benefit health when consumed in an effective amount. Desirably, probiotics beneficially affect the human body's naturally-occurring gastrointestinal microflora and impart health benefits apart from nutrition. Probiotics may include, without limitation, bacteria, yeasts, and fungi.

Prebiotics, in accordance with the teachings of this invention, are compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect the human body's naturally-occurring gastrointestinal microflora and thereby impart health benefits apart from just nutrition. Prebiotic foods enter the colon and serve as substrate for the endogenous bacteria, thereby indirectly providing the host with energy, metabolic substrates, and essential micronutrients. The body's digestion and absorption of prebiotic foods is dependent upon bacterial metabolic activity, which salvages energy for the host from nutrients that escaped digestion and absorption in the small intestine.

According to particular embodiments, the probiotic is a beneficial microorganism that beneficially affects the human body's naturally-occurring gastrointestinal microflora and imparts health benefits apart from nutrition. Examples of probiotics include, but are not limited to, bacteria of the genus *Lactobacilli, Bifidobacteria, Streptococci*, or combinations thereof, that confer beneficial effects to humans.

In particular embodiments of the invention, the at least one probiotic is chosen from the genus *Lactobacilli*. *Lactobacilli* (i.e., bacteria of the genus *Lactobacillus*, hereinafter "*L.*") have been used for several hundred years as a food preservative and for promoting human health. Non-limiting examples of species of *Lactobacilli* found in the human intestinal tract include *L. acidophilus, L. casei, L. fermentum, L. saliva roes, L. brevis, L. leichmannii, L. plantarum, L. cellobiosus, L. reuteri, L. rhamnosus, L. gg, L. bulgaricus*, and *L. thermophilus*.

According to other particular embodiments of this invention, the probiotic is chosen from the genus *Bifidobacteria*. *Bifidobacteria* also are known to exert a beneficial influence on human health by producing short chain fatty acids (e.g., acetic, propionic, and butyric acids), lactic, and formic acids as a result of carbohydrate metabolism. Non-limiting species of *Bifidobacteria* found in the human gastrointestinal tract include *B. angulatum, B. animalis, B. asteroides, B. bifidum, B. bourn, B. breve, B. catenulatum, B. choerinum, B. coryneforme, B. cuniculi, B. dentium, B. gallicum, B. gallinarum, B indicum, B. longum, B. magnum, B. merycicum, B. minimum, B. pseudocatenulatum, B. pseudolongum, B. psychraerophilum, B. pullorum, B. ruminantium, B. saeculare, B. scardovii, B. simiae, B. subtile, B. thermacidophilum, B. thermophilum, B. urinalis*, and *B.* sp.

According to other particular embodiments of this invention, the probiotic is chosen from the genus *Streptococcus*. *Streptococcus thermophilus* is a gram-positive facultative anaerobe. It is classified as a lactic acid bacteria and commonly is found in milk and milk products, and is used in the production of yogurt. Other non-limiting probiotic species of this bacteria include *Streptococcus salivarus* and *Streptococcus cremoris*.

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the embodiments of this invention, include, without limitation, mucopolysaccharides, oligosaccharides, polysaccharides, amino acids, vitamins, nutrient precursors, proteins and combinations thereof.

According to a particular embodiment of this invention, the prebiotic is chosen from dietary fibers, including, without limitation, polysaccharides and oligosaccharides. These compounds have the ability to increase the number of probiotics, which leads to the benefits conferred by the probiotics. Non-limiting examples of oligosaccharides that are categorized as prebiotics in accordance with particular embodiments of this invention include fructooligosaccharides, inulins, isomalto-oligosaccharides, lactilol, lactosucrose, lactulose, pyrodextrins, soy oligosaccharides, transgalacto-oligosaccharides, and xylo-oligosaccharides.

According to other particular embodiments of the invention, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

Weight Management Agent

In certain embodiments, the functional ingredient is at least one weight management agent.

As used herein, the at least one weight management agent may be single weight management agent or a plurality of weight management agents as a functional ingredient for the compositions provided herein. Generally, according to particular embodiments of this invention, the at least one weight management agent is present in the composition in an amount sufficient to promote health and wellness.

As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrient selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment weight management agent is a dietary fat. Dietary fats are lipids comprising combinations of saturated and unsaturated fatty acids. Polyunsaturated fatty acids have been shown to have a greater satiating power than mono-unsaturated fatty acids. Accordingly, the dietary fats embodied herein desirably comprise poly-unsaturated fatty acids, non-limiting examples of which include triacylglycerols.

In a particular embodiment, the weight management agents is an herbal extract. Extracts from numerous types of plants have been identified as possessing appetite suppressant properties. Non-limiting examples of plants whose extracts have appetite suppressant properties include plants of the genus *Hoodia, Trichocaulon, Caralluma, Stapelia, Orbea, Asclepias*, and *Camelia*. Other embodiments include extracts derived from Gymnema Sylvestre, Kola Nut, Citrus Auran tium, Yerba Mate, Griffonia Simplicifolia, Guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap. Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In a particular embodiment, the herbal extract is derived from a plant of the genus *Hoodia*, species of which include *H. alstonii, H. currorii, H. dregei, H. flava, H. gordonii, H. jutatae, H. mossamedensis, H. officinalis, H. parviflorai, H. pedicellata, H. pilifera, H. ruschii*, and *H. triebneri*. *Hoodia* plants are stem succulents native to southern Africa. A sterol glycoside of *Hoodia*, known as P57, is believed to be responsible for the appetite-suppressant effect of the *Hoodia* species.

In another particular embodiment, the herbal extract is derived from a plant of the genus *Caralluma*, species of which include *C. indica, C. fimbriata, C. attenuate, C. tuberculate, C. edulis, C. adscendens, C. stalagmifera, C. umbellate, C. penicillata, C. russeliana, C. retrospicens, C. Arabica*, and *C. lasiantha*. *Carralluma* plants belong to the same Subfamily as *Hoodia*, Asclepiadaceae. *Caralluma* are small, erect and fleshy plants native to India having medicinal properties, such as appetite suppression, that generally are attributed to glycosides belonging to the pregnane group of glycosides, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X.

In another particular embodiment, the at least one herbal extract is derived from a plant of the genus *Trichocaulon*. *Trichocaulon* plants are succulents that generally are native to southern Africa, similar to *Hoodia*, and include the species *T. piliferum* and *T. officinale*.

In another particular embodiment, the herbal extract is derived from a plant of the genus *Stapelia* or *Orbea*, species of which include *S. gigantean* and *O. variegate*, respectively. Both *Stapelia* and *Orbea* plants belong to the same Subfamily as *Hoodia*, Asclepiadaceae. Not wishing to be bound by any theory, it is believed that the compounds exhibiting appetite suppressant activity are saponins, such as pregnane glycosides, which include stavarosides A, B, C, D, E, F, G, H, I, J, and K.

In another particular embodiment, the herbal extract is derived from a plant of the genus *Asclepias*. *Asclepias* plants also belong to the Asclepiadaceae family of plants. Non-limiting examples of *Asclepias* plants include *A. incarnate, A. curassayica, A. syriaca*, and *A. tuberose*. Not wishing to be bound by any theory, it is believed that the extracts comprise steroidal compounds, such as pregnane glycosides and pregnane aglycone, having appetite suppressant effects.

In a particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

Osteoporosis Management Agent

In certain embodiments, the functional ingredient is at least one osteoporosis management agent.

As used herein, the at least one osteoporosis management agent may be single osteoporosis management agent or a plurality of osteoporosis management agent as a functional ingredient for the compositions provided herein. Generally, according to particular embodiments of this invention, the at least one osteoporosis management agent is present in the composition in an amount sufficient to promote health and wellness.

Osteoporosis is a skeletal disorder of compromised bone strength, resulting in an increased risk of bone fracture. Generally, osteoporosis is characterized by reduction of the bone mineral density (BMD), disruption of bone microarchitecture, and changes to the amount and variety of non-collagenous proteins in the bone.

In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium source. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium lactate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Not wishing to be bound by any theory, it is believed that the plants and plant extracts stimulates bone morphogenic proteins and/or inhibits bone resorption, thereby stimulating bone regeneration and strength. Non-limiting examples of suitable plants and plant extracts as osteoporosis management agents include species of the genus *Taraxacum* and *Amelanchier*, as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium, Erigonoum, Soya, Mentha, Ocimum, thymus, Tanacetum, Plantago, Spearmint, Bixa, Vitis, Rosemarinus, Rhus,* and *Anethum,* as disclosed in U.S. Patent Publication No. 2005/0079232.

Phytoestrogen

In certain embodiments, the functional ingredient is at least one phytoestrogen.

As used herein, the at least one phytoestrogen may be single phytoestrogen or a plurality of phytoestrogens as a functional ingredient for the compositions provided herein. Generally, according to particular embodiments of this invention, the at least one phytoestrogen is present in the composition in an amount sufficient to promote health and wellness.

Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect.

Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, ginseng root, groundsel herb, licorice, liferoot herb, motherwort herb, peony root, raspberry leaves, rose family plants, sage leaves, sarsaparilla root, saw palmetto berried, wild yam root, yarrow blossoms, legumes, soybeans, soy products (e.g., miso, soy flour, soymilk, soy nuts, soy protein isolate, tempen, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, soya flour, tansy, and root of the kudzu vine (pueraria root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogen isoflavones in accordance with embodiments of this invention include genistein, daidzein, glycitein, biochanin A, formononetin, their respective naturally occurring glycosides and glycoside conjugates, matairesinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa spouts, chickpeas, peanuts, and red clover.

Long-Chain Primary Aliphatic Saturated Alcohol

In certain embodiments, the functional ingredient is at least one long chain primary aliphatic saturated alcohol.

As used herein, the at least one long chain primary aliphatic saturated alcohol may be single long chain primary aliphatic saturated alcohol or a plurality of long chain primary aliphatic saturated alcohols as a functional ingredient for the compositions provided herein. Generally, according to particular embodiments of this invention, the at least one long chain primary aliphatic saturated alcohol is present in the composition in an amount sufficient to promote health and wellness.

Long-chain primary aliphatic saturated alcohols are a diverse group of organic compounds. The term alcohol refers to the fact these compounds feature a hydroxyl group (—OH) bound to a carbon atom. The term primary refers to the fact that in these compounds the carbon atom which is bound to the hydroxyl group is bound to only one other carbon atom. The term saturated refers to the fact that these compounds feature no carbon to carbon pi bonds. The term aliphatic refers to the fact that the carbon atoms in these compounds are joined together in straight or branched chains rather than in rings. The term long-chain refers to the fact that the number of carbon atoms in these compounds is at least 8 carbons).

Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In a particularly desirable embodiment of the invention, the long-chain primary aliphatic saturated alcohols are policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

Long-chain primary aliphatic saturated alcohols are derived from natural fats and oils. They may be obtained from these sources by using extraction techniques well known to those of ordinary skill in the art. Policosanols can be isolated from a variety of plants and materials including sugar cane (*Saccharum officinarium*), yams (e.g. *Dioscorea opposite*), bran from rice (e.g. *Oryza sativa*), and beeswax. Policosanols may be obtained from these sources by using extraction techniques well known to those of ordinary skill in the art. A description of such extraction techniques can be found in U.S. Pat. Appl. No. 2005/0220868, the disclosure of which is expressly incorporated by reference.

Phytosterols

In certain embodiments, the functional ingredient is at least one phytosterol, phytostanol or combination thereof.

Generally, according to particular embodiments of this invention, the at least one phytosterol, phytostanol or combination thereof is present in the composition in an amount sufficient to promote health and wellness.

As used herein, the phrases "stanol", "plant stanol" and "phytostanol" are synonymous.

Plant sterols and stanols are present naturally in small quantities in many fruits, vegetables, nuts, seeds, cereals, legumes, vegetable oils, bark of the trees and other plant sources. Although people normally consume plant sterols and stanols every day, the amounts consumed are insufficient to have significant cholesterol-lowering effects or other health benefits. Accordingly, it would be desirable to supplement food and beverages with plant sterols and stanols.

Sterols are a subgroup of steroids with a hydroxyl group at C-3. Generally, phytosterols have a double bond within the steroid nucleus, like cholesterol; however, phytosterols also may comprise a substituted sidechain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. According to particular embodiments of this invention, non-limiting examples of phytosterols well known to those or ordinary skill in the art include 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. According to particular embodiments of this invention, non-limiting examples of phytostanols include β-sitostanol, campestanol, cycloartanol, and saturated forms of other triterpene alcohols.

Both phytosterols and phytostanols, as used herein, include the various isomers such as the α and β isomers (e.g., α-sitosterol and β-sitostanol, which comprise one of the most effective phytosterols and phytostanols, respectively, for lowering serum cholesterol in mammals).

The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473, the disclosures of which are incorporated herein by reference in their entirety. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

Generally, the amount of functional ingredient in the composition varies widely depending on the particular composition and the desired functional ingredient. Those of ordinary skill in the art will readily acertain the appropriate amount of functional ingredient for each composition.

In one embodiment, a method for preparing a composition comprises combining a compound of formula (1) and at least one sweetener and/or additive and/or functional ingredient.

Consumables

In one embodiment, the composition of the present invention is a consumable comprising a compound of formula (1), or a consumable comprising a composition comprising a compound of formula (1).

The compound of formula (1), or a composition comprising the same, can be incorporated in any known edible or oral composition (referred to herein as a "consumable"), such as, for example, pharmaceutical compositions, edible gel mixes and compositions, dental compositions, foodstuffs (confections, condiments, chewing gum, cereal compositions baked goods dairy products, and tabletop sweetener compositions) beverages and beverage products.

Consumables, as used herein, mean substances which are contacted with the mouth of man or animal, including substances which are taken into and subsequently ejected from the mouth and substances which are drunk, eaten, swallowed or otherwise ingested, and are safe for human or animal consumption when used in a generally acceptable range.

For example, a beverage is a consumable. The beverage may be sweetened or unsweetened. A compound of formula (1), or a composition comprising a compound of formula (1) may be added to a beverage or beverage matrix to sweeten the beverage or enhance its existing sweetness or flavor.

In one embodiment, the present invention is a consumable comprising a compound of formula (1). The concentration of the compound of formula (1) in the consumable may be above, at or below the threshold sweetness concentration of the compound of formula (1)

In a particular embodiment, the present invention is a consumable comprising a compound of formula (1). The concentration of the compound of formula (1) in the beverage may be above, at or below the threshold sweetness concentration of the compound of formula (1)

The consumable can optionally include additives, additional sweeteners, functional ingredients and combinations thereof, as described herein. Any of the additive, additional sweetener and functional ingredients described above can be present in the consumable.

Pharmaceutical Compositions

In one embodiment, the present invention is a pharmaceutical composition that comprises a pharmaceutically active substance and a compound of formula (1).

In another embodiment, the present invention is a pharmaceutical composition that comprises a pharmaceutically active substance and a composition comprising a compound of formula (1).

A compound of formula (1) or composition comprising a compound of formula (1) can be present as an excipient material in the pharmaceutical composition, which can mask a bitter or otherwise undesirable taste of a pharmaceutically active substance or another excipient material. The pharmaceutical composition may be in the form of a tablet, a capsule, a liquid, an aerosol, a powder, an effervescent tablet or powder, a syrup, an emulsion, a suspension, a solution, or any other form for providing the pharmaceutical composition to a patient. In particular embodiments, the pharmaceutical composition may be in a form for oral administration, buccal administration, sublingual administration, or any other route of administration as known in the art.

As referred to herein, "pharmaceutically active substance" means any drug, drug formulation, medication, prophylactic agent, therapeutic agent, or other substance having biological activity. As referred to herein, "excipient material" refers to any inactive substance used as a vehicle for an active ingredient, such as any material to facilitate handling, stability, dispersibility, wettability, and/or release kinetics of a pharmaceutically active substance.

Suitable pharmaceutically active substances include, but are not limited to, medications for the gastrointestinal tract or digestive system, for the cardiovascular system, for the central nervous system, for pain or consciousness, for musculo-skeletal disorders, for the eye, for the ear, nose and oropharynx, for the respiratory system, for endocrine problems, for the reproductive system or urinary system, for contraception, for obstetrics and gynecology, for the skin, for infections and infestations, for immunology, for allergic disorders, for nutrition, for neoplastic disorders, for diagnostics, for euthanasia, or other biological functions or disorders. Examples of suitable pharmaceutically active substances for embodiments of the present invention include, but are not limited to, antacids, reflux suppressants, antiflatulents, antidopaminergics, proton pump inhibitors, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, peripheral activators, ACE inhibitors, angiotensin receptor blockers, alpha blockers, anticoagulants, heparin, antiplatelet drugs, fibrinolytics, anti-hemophilic factors, haemostatic drugs, hypolipidaemic agents, statins, hynoptics, anaesthetics, antipsychotics, antidepressants, anti-emetics, anticonvulsants, antiepileptics, anxiolytics, barbiturates, movement disorder drugs, stimulants, benzodiazepines, cyclopyrrolones, dopamine antagonists, antihistamines, cholinergics, anticholinergics, emetics, cannabinoids, analgesics, muscle relaxants, antibiotics, aminoglycosides, anti-virals, anti-fungals, anti-inflammatories, anti-gluacoma drugs, sympathomimetics, steroids, ceruminolytics, bronchodilators, NSAIDS, antitussive, mucolytics, decongestants, corticosteroids, androgens, antiandrogens, gonadotropins, growth hormones, insulin, antidiabetics, thyroid hormones, calcitonin, diphosponates, vasopressin analogues, alkalizing agents, quinolones, anticholinesterase, sildenafil, oral contraceptives, Hormone Replacement Therapies, bone regulators, follicle stimulating hormones, luteinizings hormones, gamolenic acid, progestogen, dopamine agonist, oestrogen, prostaglandin, gonadorelin, clomiphene, tamoxifen, diethylstilbestrol, antileprotics, antituberculous drugs, antimalarials, anthelmintics, antiprotozoal, antiserums, vaccines, interferons, tonics, vitamins, cytotoxic drugs, sex hormones, aromatase inhibitors, somatostatin inhibitors, or similar type substances, or combinations thereof. Such components generally are recognized as safe (GRAS) and/or are U.S. Food and Drug Administration (FDA)-approved.

The pharmaceutically active substance is present in the pharmaceutical composition in widely ranging amounts depending on the particular pharmaceutically active agent being used and its intended applications. An effective dose of any of the herein described pharmaceutically active substances can be readily determined by the use of conventional techniques and by observing results obtained under analogous circumstances. In determining the effective dose, a number of factors are considered including, but not limited to: the species of the patient; its size, age, and general health; the specific disease involved; the degree of involvement or the severity of the disease; the response of the individual patient; the particular pharmaceutically active agent administered; the mode of administration; the bioavailability characteristic of the preparation administered; the dose regimen selected; and the use of concomitant medication. The pharmaceutically active substance is included in the pharmaceutically acceptable carrier, diluent, or excipient in an amount sufficient to deliver to a patient a therapeutic amount of the pharmaceutically active substance in vivo in the absence of serious toxic effects when used in generally acceptable amounts. Thus, suitable amounts can be readily discerned by those skilled in the art.

According to particular embodiments of the present invention, the concentration of pharmaceutically active substance in the pharmaceutical composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimes should be adjusted over time according to the individual need and the professional judgment of the person administering or supervising the administration of the pharmaceutical compositions, and that the dosage ranges set forth herein are exemplary only and are not intended to limit the scope or practice of the claimed composition. The pharmaceutically active substance may be administered at once, or may be divided into a number of smaller doses to be administered at varying intervals of time.

The pharmaceutical composition also may comprise other pharmaceutically acceptable excipient materials in addition to a compound of formula (1) or composition comprising a compound of formula (1). Examples of suitable excipient materials for embodiments of this invention include, but are not limited to, antiadherents, binders (e.g., microcrystalline cellulose, gum tragacanth, or gelatin), coatings, disintegrants, fillers, diluents, softeners, emulsifiers, flavoring agents, coloring agents, adjuvants, lubricants, functional agents (e.g., nutrients), viscosity modifiers, bulking agents, glidiants (e.g., colloidal silicon dioxide) surface active agents, osmotic agents, diluents, or any other non-active ingredient, or combinations thereof. For example, the pharmaceutical compositions of the present invention may include excipient materials selected from the group consisting of calcium carbonate, coloring agents, whiteners, preservatives, and flavors, triacetin, magnesium stearate, sterotes, natural or artificial flavors, essential oils, plant extracts, fruit essences, gelatins, or combinations thereof.

The excipient material of the pharmaceutical composition may optionally include other artificial or natural sweeteners, bulk sweeteners, or combinations thereof. Bulk sweeteners include both caloric and non-caloric compounds. In a particular embodiment, the additive functions as the bulk sweetener. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. In particular embodiments, the bulk sweetener is present in the pharmaceutical composition in widely ranging amounts depending on the degree of sweetness desired. Suitable amounts of both sweeteners would be readily discernable to those skilled in the art.

Edible Gel Mixes and Edible Gel Compositions

In one embodiment, the present invention is an edible gel or edible gel mix that comprises a compound of formula (1). In another embodiment, the present invention is an edible gel or edible gel mix that comprises a composition comprising a compound of formula (1).

Edible gels are gels that can be eaten. A gel is a colloidal system in which a network of particles spans the volume of a liquid medium. Although gels mainly are composed of liquids, and thus exhibit densities similar to liquids, gels have the structural coherence of solids due to the network of particles that spans the liquid medium. For this reason, gels generally appear to be solid, jelly-like materials. Gels can be used in a number of applications. For example, gels can be used in foods, paints, and adhesives.

Non-limiting examples of edible gel compositions for use in particular embodiments include gel desserts, puddings, jellies, pastes, trifles, aspics, marshmallows, gummy candies, or the like. Edible gel mixes generally are powdered or granular solids to which a fluid may be added to form an edible gel composition. Non-limiting examples of fluids for use in particular embodiments include water, dairy fluids, dairy analogue fluids, juices, alcohol, alcoholic beverages, and combinations thereof. Non-limiting examples of dairy fluids which may be used in particular embodiments include milk, cultured milk, cream, fluid whey, and mixtures thereof. Non-limiting examples of dairy analogue fluids which may be used in particular embodiments include, for example, soy milk and non-dairy coffee whitener. Because edible gel products found in the marketplace typically are sweetened with sucrose, it is desirable to sweeten edible gels with an alternative sweetener in order provide a low-calorie or non-calorie alternative.

As used herein, the term "gelling ingredient" denotes any material that can form a colloidal system within a liquid medium. Non-limiting examples of gelling ingredients for use in particular embodiments include gelatin, alginate, carageenan, gum, pectin, konjac, agar, food acid, rennet, starch, starch derivatives, and combinations thereof. It is well known to those having ordinary skill in the art that the amount of gelling ingredient used in an edible gel mix or an edible gel composition varies considerably depending on a number of factors, such as the particular gelling ingredient used, the particular fluid base used, and the desired properties of the gel.

It is well known to those having ordinary skill in the art that the edible gel mixes and edible gels may be prepared using other ingredients in addition to a compound of formula (1) or the composition comprising a compound of formula (1) and the gelling agent. Non-limiting examples of other ingredients for use in particular embodiments include a food acid, a salt of a food acid, a buffering system, a bulking agent, a sequestrant, a cross-linking agent, one or more flavors, one or more colors, and combinations thereof. Non-limiting examples of food acids for use in particular embodiments include citric acid, adipic acid, fumaric acid, lactic acid, malic acid, and combinations thereof. Non-limiting examples of salts of food acids for use in particular embodiments include sodium salts of food acids, potassium salts of food acids, and combinations thereof. Non-limiting examples of bulking agents for use in particular embodiments include raftilose, isomalt, sorbitol, polydextrose, maltodextrin, and combinations thereof. Non-limiting examples of sequestrants for use in particular embodiments include calcium disodium ethylene tetra-acetate, glucono delta-lactone, sodium gluconate, potassium gluconate, ethylenediaminetetraacetic acid (EDTA), and combinations thereof. Non-limiting examples of cross-linking agents for use in particular embodiments include calcium ions, magnesium ions, sodium ions, and combinations thereof.

Dental Compositions

In one embodiment, the present invention is a dental composition that comprises a compound of formula (1). In another embodiment, the present invention is a dental composition that comprises a composition comprising a compound of formula (1). Dental compositions generally comprise an active dental substance and a base material. A compound of formula (1) or a composition comprising a compound of formula (1) can be used as the base material to sweeten the dental composition. The dental composition may be in the form of any oral composition used in the oral cavity such as mouth freshening agents, gargling agents, mouth rinsing agents, toothpaste, tooth polish, dentifrices, mouth sprays, teeth-whitening agent, dental floss, and the like, for example.

As referred to herein, "active dental substance" means any composition which can be used to improve the aesthetic appearance and/or health of teeth or gums or prevent dental caries. As referred to herein, "base material" refers to any inactive substance used as a vehicle for an active dental substance, such as any material to facilitate handling, stability, dispersibility, wettability, foaming, and/or release kinetics of an active dental substance.

Suitable active dental substances for embodiments of this invention include, but are not limited to, substances which remove dental plaque, remove food from teeth, aid in the elimination and/or masking of halitosis, prevent tooth decay, and prevent gum disease (i.e., Gingiva). Examples of suitable active dental substances for embodiments of the present invention include, but are not limited to, anticaries drugs, fluoride, sodium fluoride, sodium monofluorophosphate, stannos fluoride, hydrogen peroxide, carbamide peroxide (i.e., urea peroxide), antibacterial agents, plaque removing agents, stain removers, anticalculus agents, abrasives, baking soda, percarbonates, perborates of alkali and alkaline earth metals, or similar type substances, or combinations thereof. Such components generally are recognized as safe (GRAS) and/or are U.S. Food and Drug Administration (FDA)-approved.

According to particular embodiments of the invention, the active dental substance is present in the dental composition in an amount ranging from about 50 ppm to about 3000 ppm of the dental composition. Generally, the active dental substance is present in the dental composition in an amount effective to at least improve the aesthetic appearance and/or health of teeth or gums marginally or prevent dental caries. For example, a dental composition comprising a toothpaste may include an active dental substance comprising fluoride in an amount of about 850 to 1,150 ppm.

The dental composition also may comprise other base materials in addition to the a compound of formula (1) or composition comprising a compound of formula (1). Examples of suitable base materials for embodiments of this invention include, but are not limited to, water, sodium lauryl sulfate or other sulfates, humectants, enzymes, vitamins, herbs, calcium, flavorings (e.g., mint, bubblegum, cinnamon, lemon, or orange), surface-active agents, binders, preservatives, gelling agents, pH modifiers, peroxide activators, stabilizers, coloring agents, or similar type materials, and combinations thereof.

The base material of the dental composition may optionally include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. Generally, the amount of bulk sweetener present in the dental composition ranges widely depending on the particular embodiment of the dental composition and the desired degree of sweetness. Those of ordinary skill in the art will readily ascertain the appropriate amount of bulk sweetener. In particular embodiments, the bulk sweetener is present in the dental composition in an amount in the range of about 0.1 to about 5 weight percent of the dental composition.

According to particular embodiments of the invention, the base material is present in the dental composition in an amount ranging from about 20 to about 99 percent by weight of the dental composition. Generally, the base material is present in an amount effective to provide a vehicle for an active dental substance.

In a particular embodiment, a dental composition comprises a compound of formula (1) and an active dental substance. In another particular embodiment, a dental composition comprises a composition comprising a compound of formula (1) and an active dental substance. Generally, the amount of the sweetener varies widely depending on the nature of the particular dental composition and the desired degree of sweetness.

Foodstuffs include, but are not limited to, confections, condiments, chewing gum, cereal, baked goods, and dairy products.

Confections

In one embodiment, the present invention is a confection that comprises a compound of formula (1). In another embodiment, the present invention is a confection that comprises a composition comprising a compound of formula (1).

As referred to herein, "confection" can mean a sweet, a lollie, a confectionery, or similar term. The confection generally contains a base composition component and a sweetener component. A compound of formula (1) or a composition comprising a compound of formula (1) can serve as the sweetener component. The confection may be in the form of any food that is typically perceived to be rich in sugar or is typically sweet. According to particular embodiments of the present invention, the confections may be bakery products such as pastries; desserts such as yogurt, jellies, drinkable jellies, puddings, Bavarian cream, blancmange, cakes, brownies, mousse and the like, sweetened food products eaten at tea time or following meals; frozen foods; cold confections, e. g. types of ice cream such as ice cream, ice milk, lacto-ice and the like (food products in which sweeteners and various other types of raw materials are added to milk products, and the resulting mixture is agitated and frozen), and ice confections such as sherbets, dessert ices and the like (food products in which various other types of raw materials are added to a sugary liquid, and the resulting mixture is agitated and frozen); general confections, e. g., baked confections or steamed confections such as crackers, biscuits, buns with bean-jam filling, halvah, alfajor, and the like; rice cakes and snacks; table top products; general sugar confections such as chewing gum (e.g. including compositions which comprise a substantially water-insoluble, chewable gum base, such as chicle or substitutes thereof, including jetulong, guttakay rubber or certain comestible natural synthetic resins or waxes), hard candy, soft candy, mints, nougat candy, jelly beans, fudge, toffee, taffy, Swiss milk tablet, licorice candy, chocolates, gelatin candies, marshmallow, marzipan, divinity, cotton candy, and the like; sauces including fruit flavored sauces, chocolate sauces and the like; edible gels; crèmes including butter crèmes, flour pastes, whipped cream and the like; jams including strawberry jam, marmalade and the like; and breads including sweet breads and the like or other starch products, and combinations thereof.

As referred to herein, "base composition" means any composition which can be a food item and provides a matrix for carrying the sweetener component.

Suitable base compositions for embodiments of this invention may include flour, yeast, water, salt, butter, eggs, milk, milk powder, liquor, gelatin, nuts, chocolate, citric acid, tartaric acid, fumaric acid, natural flavors, artificial flavors, colorings, polyols, sorbitol, isomalt, maltitol, lactitol, malic acid, magnesium stearate, lecithin, hydrogenated glucose syrup, glycerine, natural or synthetic gum, starch, and the like, and combinations thereof. Such components generally are recognized as safe (GRAS) and/or are U.S.

Food and Drug Administration (FDA)-approved. According to particular embodiments of the invention, the base composition is present in the confection in an amount ranging from about 0.1 to about 99 weight percent of the confection. Generally, the base composition is present in the confection in an amount, in combination with a compound of formula (1) or a composition comprising a compound of formula (1) to provide a food product.

The base composition of the confection may optionally include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. Generally, the amount of bulk sweetener present in the confection ranges widely depending on the particular embodiment of the confection and the desired degree of sweetness. Those of ordinary skill in the art will readily ascertain the appropriate amount of bulk sweetener.

In a particular embodiment, a confection comprises a compound of formula (1) or a composition comprising a compound of formula (1) and a base composition. Generally, the amount of a compound of formula (1) in the confection ranges widely depending on the particular embodiment of the confection and the desired degree of sweetness. Those of ordinary skill in the art will readily ascertain the appropriate amount. In a particular embodiment, a compound of formula (1) is present in the confection in an amount in the range of about 30 ppm to about 6000 ppm of the confection. In another embodiment, a compound of formula (1) is present in the confection in an amount in the range of about 1 ppm to about 10,000 ppm of the confection. In embodiments where the confection comprises hard candy, a compound of formula (1) is present in an amount in the range of about 150 ppm to about 2250 ppm of the hard candy.

Condiment Compositions

In one embodiment, the present invention is a condiment that comprises a compound of formula (1). In another embodiment the present invention is a condiment that comprises a composition comprising a compound of formula (1). Condiments, as used herein, are compositions used to enhance or improve the flavor of a food or beverage. Non-limiting examples of condiments include ketchup (catsup); mustard; barbecue sauce; butter; chili sauce; chutney; cocktail sauce; curry; dips; fish sauce; horseradish; hot sauce; jellies, jams, marmalades, or preserves; mayonnaise; peanut butter; relish; remoulade; salad dressings (e.g., oil and vinegar, Caesar, French, ranch, bleu cheese, Russian, Thousand Island, Italian, and balsamic vinaigrette); salsa; sauerkraut; soy sauce; steak sauce; syrups; tartar sauce; and Worcestershire sauce.

Condiment bases generally comprise a mixture of different ingredients, non-limiting examples of which include vehicles (e.g., water and vinegar); spices or seasonings (e.g., salt, pepper, garlic, mustard seed, onion, paprika, turmeric, and combinations thereof); fruits, vegetables, or their products (e.g., tomatoes or tomato-based products (paste, puree), fruit juices, fruit juice peels, and combinations thereof); oils or oil emulsions, particularly vegetable oils; thickeners (e.g., xanthan gum, food starch, other hydrocolloids, and combinations thereof); and emulsifying agents (e.g., egg yolk solids, protein, gum arabic, carob bean gum, guar gum, gum karaya, gum tragacanth, carageenan, pectin, propylene glycol esters of alginic acid, sodium carboxymethyl-cellulose, polysorbates, and combinations thereof). Recipes for condiment bases and methods of making condiment bases are well known to those of ordinary skill in the art.

Generally, condiments also comprise caloric sweeteners, such as sucrose, high fructose corn syrup, molasses, honey, or brown sugar. In exemplary embodiments of the condiments provided herein, a compound of formula (1) or a composition comprising a compound of formula (1) is used instead of traditional caloric sweeteners. Accordingly, a condiment composition desirably comprises a compound of formula (1) or a composition comprising a compound of formula (1) and a condiment base.

The condiment composition optionally may include other natural and/or synthetic high-potency sweeteners, bulk sweeteners, pH modifying agents (e.g., lactic acid, citric acid, phosphoric acid, hydrochloric acid, acetic acid, and combinations thereof), fillers, functional agents (e.g., pharmaceutical agents, nutrients, or components of a food or plant), flavorings, colorings, or combinations thereof.

Chewing Gum Compositions

In one embodiment, the present invention is a chewing gum composition that comprises a compound of formula (1). In another embodiment, the present invention is a chewing gum composition that comprises a composition comprising a compound of formula (1). Chewing gum compositions generally comprise a water-soluble portion and a water-insoluble chewable gum base portion. The water soluble portion, which typically includes the composition of the present invention, dissipates with a portion of the flavoring agent over a period of time during chewing while the insoluble gum base portion is retained in the mouth. The insoluble gum base generally determines whether a gum is considered chewing gum, bubble gum, or a functional gum.

The insoluble gum base, which is generally present in the chewing gum composition in an amount in the range of about 15 to about 35 weight percent of the chewing gum composition, generally comprises combinations of elastomers, softeners (plasticizers), emulsifiers, resins, and fillers. Such components generally are considered food grade, recognized as safe (GRA), and/or are U.S. Food and Drug Administration (FDA)-approved.

Elastomers, the primary component of the gum base, provide the rubbery, cohesive nature to gums and can include one or more natural rubbers (e.g., smoked latex, liquid latex, or guayule); natural gums (e.g., jelutong, perillo, sorva, massaranduba balata, massaranduba chocolate, nispero, rosindinha, chicle, and gutta hang kang); or synthetic elastomers (e.g., butadiene-styrene copolymers, isobutylene-isoprene copolymers, polybutadiene, polyisobutylene, and vinyl polymeric elastomers). In a particular embodiment, the elastomer is present in the gum base in an amount in the range of about 3 to about 50 weight percent of the gum base.

Resins are used to vary the firmness of the gum base and aid in softening the elastomer component of the gum base. Non-limiting examples of suitable resins include a rosin ester, a terpene resin (e.g., a terpene resin from α-pinene, β-pinene and/or d-limonene), polyvinyl acetate, polyvinyl alcohol, ethylene vinyl acetate, and vinyl acetate-vinyl laurate copolymers. Non-limiting examples of rosin esters include a glycerol ester of a partially hydrogenated rosin, a glycerol ester of a polymerized rosin, a glycerol ester of a partially dimerized rosin, a glycerol ester of rosin, a pentaerythritol ester of a partially hydrogenated rosin, a methyl ester of rosin, or a methyl ester of a partially hydrogenated rosin. In a particular embodiment, the resin is present in the gum base in an amount in the range of about 5 to about 75 weight percent of the gum base.

Softeners, which also are known as plasticizers, are used to modify the ease of chewing and/or mouthfeel of the chewing gum composition. Generally, softeners comprise oils, fats, waxes, and emulsifiers. Non-limiting examples of oils and fats include tallow, hydrogenated tallow, large, hydrogenated or partially hydrogenated vegetable oils (e.g., soybean, canola, cottonseed, sunflower, palm, coconut, corn, safflower, or palm kernel oils), cocoa butter, glycerol monostearate, glycerol triacetate, glycerol abietate, leithin, monoglycerides, diglycerides, triglycerides acetylated monoglycerides, and free fatty acids. Non-limiting examples of waxes include polypropylene/polyethylene/Fisher-Tropsch waxes, paraffin, and microcrystalline and natural waxes (e.g., candelilla, beeswas and carnauba). Microcrystalline waxes, especially those with a high degree of crystallinity and a high melting point, also may be considered as bodying agents or textural modifiers. In a particular embodiment, the softeners are present in the gum base in an amount in the range of about 0.5 to about 25 weight percent of the gum base.

Emulsifiers are used to form a uniform dispersion of the insoluble and soluble phases of the chewing gum composition and also have plasticizing properties. Suitable emulsifiers include glycerol monostearate (GMS), lecithin (Phosphatidyl choline), polyglycerol polyricinoleic acid (PPGR), mono and diglycerides of fatty acids, glycerol distearate, tracetin, acetylated monoglyceride, glycerol triactetate, and magnesium stearate. In a particular embodiment, the emulsifiers are present in the gum base in an amount in the range of about 2 to about 30 weight percent of the gum base.

The chewing gum composition also may comprise adjuvants or fillers in either the gum base and/or the soluble portion of the chewing gum composition. Suitable adjuvants and fillers include lecithin, inulin, polydextrin, calcium carbonate, magnesium carbonate, magnesium silicate, ground limestome, aluminum hydroxide, aluminum silicate, talc, clay, alumina, titanium dioxide, and calcium phosphate. In particular embodiments, lecithin can be used as an inert filler to decrease the stickiness of the chewing gum composition. In other particular embodiments, lactic acid copolymers, proteins (e.g., gluten and/or zein) and/or guar can be used to create a gum that is more readily biodegradable. The adjuvants or fillers are generally present in the gum base in an amount up to about 20 weight percent of the gum base. Other optional ingredients include coloring agents, whiteners, preservatives, and flavors.

In particular embodiments of the chewing gum composition, the gum base comprises about 5 to about 95 weight percent of the chewing gum composition, more desirably about 15 to about 50 weight percent of the chewing gum composition, and even more desirably from about 20 to about 30 weight percent of the chewing gum composition.

The soluble portion of the chewing gum composition may optionally include other artificial or natural sweeteners, bulk sweeteners, softeners, emulsifiers, flavoring agents, coloring agents, adjuvants, fillers, functional agents (e.g., pharmaceutical agents or nutrients), or combinations thereof. Suitable examples of softeners and emulsifiers are described above.

Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. In particular embodiments, the bulk sweetener is present in the chewing gum composition in an amount in the range of about 1 to about 75 weight percent of the chewing gum composition.

Flavoring agents may be used in either the insoluble gum base or soluble portion of the chewing gum composition. Such flavoring agents may be natural or artificial flavors. In a particular embodiment, the flavoring agent comprises an essential oil, such as an oil derived from a plant or a fruit, peppermint oil, spearmint oil, other mint oils, clove oil, cinnamon oil, oil of wintergreen, bay, thyme, cedar leaf, nutmeg, allspice, sage, mace, and almonds. In another particular embodiment, the flavoring agent comprises a plant extract or a fruit essence such as apple, banana, watermelon, pear, peach, grape, strawberry, raspberry, cherry, plum, pineapple, apricot, and mixtures thereof. In still another particular embodiment, the flavoring agent comprises a citrus flavor, such as an extract, essence, or oil of lemon, lime, orange, tangerine, grapefruit, citron, or kumquat.

In a particular embodiment, a chewing gum composition comprises a compound of formula (1) or a composition comprising a compound of formula (1) and a gum base. In a particular embodiment, a compound of formula (1) is present in the chewing gum composition in an amount in the range of about 1 ppm to about 10,000 ppm of the chewing gum composition.

Cereal Compositions

In one embodiment, the present invention is a cereal composition that comprises a compound of formula (1). In another embodiment, the present invention is a cereal composition that comprises a composition comprising a compound of formula (1). Cereal compositions typically are eaten either as staple foods or as snacks. Non-limiting examples of cereal compositions for use in particular embodiments include ready-to-eat cereals as well as hot cereals. Ready-to-eat cereals are cereals which may be eaten without further processing (i.e. cooking) by the consumer. Examples of ready-to-eat cereals include breakfast cereals and snack bars. Breakfast cereals typically are processed to produce a shredded, flaky, puffy, or extruded form. Breakfast cereals generally are eaten cold and are often mixed with milk and/or fruit. Snack bars include, for example, energy bars, rice cakes, granola bars, and nutritional bars. Hot cereals generally are cooked, usually in either milk or water, before being eaten. Non-limiting examples of hot cereals include grits, porridge, polenta, rice, and rolled oats.

Cereal compositions generally comprise at least one cereal ingredient. As used herein, the term "cereal ingredient" denotes materials such as whole or part grains, whole or part seeds, and whole or part grass. Non-limiting examples of cereal ingredients for use in particular embodiments include maize, wheat, rice, barley, bran, bran endosperm, bulgur, soghums, millets, oats, rye, triticale, buchwheat, fonio, quinoa, bean, soybean, amaranth, teff, spelt, and kaniwa.

In a particular embodiment, the cereal composition comprises a compound of formula (1) or a composition comprising a compound of formula (1) and at least one cereal ingredient. A compound of formula (1) or the composition comprising a compound of formula (1) may be added to the cereal composition in a variety of ways, such as, for example, as a coating, as a frosting, as a glaze, or as a matrix blend (i.e. added as an ingredient to the cereal formulation prior to the preparation of the final cereal product).

Accordingly, in a particular embodiment, a compound of formula (1) or a composition comprising a compound of formula (1) is added to the cereal composition as a matrix blend. In one embodiment, a compound of formula (1) or a composition comprising a compound of formula (1) is blended with a hot cereal prior to cooking to provide a sweetened hot cereal product. In another embodiment, a compound of formula (1) or a composition comprising a compound of formula (1) is blended with the cereal matrix before the cereal is extruded.

In another particular embodiment, a compound of formula (1) or a composition comprising a compound of formula (1) is added to the cereal composition as a coating, such as, for example, by combining a compound of formula (1) or a comprising a compound of formula (1) with a food grade oil and applying the mixture onto the cereal. In a different embodiment, a compound of formula (1) or a composition comprising a compound of formula (1) and the food grade oil may be applied to the cereal separately, by applying either the oil or the sweetener first. Non-limiting examples of food grade oils for use in particular embodiments include vegetable oils such as corn oil, soybean oil, cottonseed oil, peanut oil, coconut oil, canola oil, olive oil, sesame seed oil, palm oil, palm kernel oil, and mixtures thereof. In yet another embodiment, food grade fats may be used in place of the oils, provided that the fat is melted prior to applying the fat onto the cereal.

In another embodiment, the a compound of formula (1) or a composition comprising a compound of formula (1) is added to the cereal composition as a glaze. Non-limiting examples of glazing agents for use in particular embodiments include corn syrup, honey syrups and honey syrup solids, maple syrups and maple syrup solids, sucrose, isomalt, polydextrose, polyols, hydrogenated starch hydrosylate, aqueous solutions thereof, and mixtures thereof. In another such embodiment, a compound of formula (1) or a composition comprising a compound of formula (1) is added as a glaze by combining with a glazing agent and a food grade oil or fat and applying the mixture to the cereal. In yet another embodiment, a gum system, such as, for example, gum acacia, carboxymethyl cellulose, or algin, may be added to the glaze to provide structural support. In addition, the glaze also may include a coloring agent, and also may include a flavor.

In another embodiment, a compound of formula (1) or a composition comprising a compound of formula (1) is added to the cereal composition as a frosting. In one such embodiment, a compound of formula (1) or a composition comprising a compound of formula (1) is combined with water and a frosting agent and then applied to the cereal. Non-limiting examples of frosting agents for use in particular embodiments include maltodextrin, sucrose, starch, polyols, and mixtures thereof. The frosting also may include a food grade oil, a food grade fat, a coloring agent, and/or a flavor.

Generally, the amount of a compound of formula (1) in a cereal composition varies widely depending on the particular type of cereal composition and its desired sweetness. Those of ordinary skill in the art can readily discern the appropriate amount of sweetener to put in the cereal composition. In a particular embodiment, a compound of formula (1) is present in the cereal composition in an amount in the range of about 0.02 to about 1.5 weight percent of the cereal composition and the at least one additive is present in the cereal composition in an amount in the range of about 1 to about 5 weight percent of the cereal composition.

Baked Goods

In one embodiment, the present invention is a baked good that comprises a compound of formula (1). In another embodiment, the present invention is a baked good that comprises a composition comprising a compound of formula (1). Baked goods, as used herein, include ready to eat and all ready to bake products, flours, and mixes requiring preparation before serving. Non-limiting examples of baked goods include cakes, crackers, cookies, brownies, muffins, rolls, bagels, donuts, strudels, pastries, croissants, biscuits, bread, bread products, and buns.

Preferred baked goods in accordance with embodiments of this invention can be classified into three groups: bread-type doughs (e.g., white breads, variety breads, soft buns, hard rolls, bagels, pizza dough, and flour tortillas), sweet doughs (e.g., danishes, croissants, crackers, puff pastry, pie crust, biscuits, and cookies), and batters (e.g., cakes such as sponge, pound, devil's food, cheesecake, and layer cake, donuts or other yeast raised cakes, brownies, and muffins). Doughs generally are characterized as being flour-based, whereas batters are more water-based.

Baked goods in accordance with particular embodiments of this invention generally comprise a combination of sweetener, water, and fat. Baked goods made in accordance with many embodiments of this invention also contain flour in order to make a dough or a batter. The term "dough" as used herein is a mixture of flour and other ingredients stiff enough to knead or roll. The term "batter" as used herein consists of flour, liquids such as milk or water, and other ingredients, and is thin enough to pour or drop from a spoon. Desirably, in accordance with particular embodiments of the invention, the flour is present in the baked goods in an amount in the range of about 15 to about 60% on a dry weight basis, more desirably from about 23 to about 48% on a dry weight basis.

The type of flour may be selected based on the desired product. Generally, the flour comprises an edible non-toxic flour that is conventionally utilized in baked goods. According to particular embodiments, the flour may be a bleached bake flour, general purpose flour, or unbleached flour. In other particular embodiments, flours also may be used that have been treated in other manners. For example, in particular embodiments flour may be enriched with additional vitamins, minerals, or proteins. Non-limiting examples of flours suitable for use in particular embodiments of the invention include wheat, corn meal, whole grain, fractions of whole grains (wheat, bran, and oatmeal), and combinations thereof. Starches or farinaceous material also may be used as the flour in particular embodiments. Common food starches generally are derived from potato, corn, wheat, barley, oat, tapioca, arrow root, and sago. Modified starches and pregelatinized starches also may be used in particular embodiments of the invention.

The type of fat or oil used in particular embodiments of the invention may comprise any edible fat, oil, or combination thereof that is suitable for baking Non-limiting examples of fats suitable for use in particular embodiments of the invention include vegetable oils, tallow, lard, marine oils, and combinations thereof. According to particular embodiments, the fats may be fractionated, partially hydrogenated, and/or intensified. In another particular embodiment, the fat desirably comprises reduced, low calorie, or non-digestible fats, fat substitutes, or synthetic fats. In yet another particular embodiment, shortenings, fats, or mixtures of hard and soft fats also may be used. In particular embodiments, shortenings may be derived principally from triglycerides derived from vegetable sources (e.g., cotton seed oil, soybean oil, peanut oil, linseed oil, sesame oil, palm oil, palm kernel oil, rapeseed oil, safflower oil, coconut oil, corn oil, sunflower seed oil, and mixtures thereof). Synthetic or natural triglycerides of fatty acids having chain lengths from 8 to 24 carbon atoms also may be used in particular embodiments. Desirably, in accordance with particular embodiments of this invention, the fat is present in the baked good in an amount in the range of about 2 to about 35% by weight on a dry basis, more desirably from about 3 to about 29% by weight on a dry basis.

Baked goods in accordance with particular embodiments of this invention also comprise water in amounts sufficient to provide the desired consistency, enabling proper forming, machining and cutting of the baked good prior or subsequent to cooking. The total moisture content of the baked good includes any water added directly to the baked good as well as water present in separately added ingredients (e.g., flour, which generally includes about 12 to about 14% by weight moisture). Desirably, in accordance with particular embodiments of this invention, the water is present in the baked good in an amount up to about 25% by weight of the baked good.

Baked goods in accordance with particular embodiments of this invention also may comprise a number of additional conventional ingredients such as leavening agents, flavors, colors, milk, milk by-products, egg, egg by-products, cocoa, vanilla or other flavoring, as well as inclusions such as nuts, raisins, cherries, apples, apricots, peaches, other fruits, citrus peel, preservative, coconuts, flavored chips such a chocolate chips, butterscotch chips, and caramel chips, and combinations thereof. In particular embodiments, the baked goods may also comprise emulsifiers, such as lecithin and monoglycerides.

According to particular embodiments of this invention, leavening agents may comprise chemical leavening agents or yeast leavening agents. Non-limiting examples of chemical leavening agents suitable for use in particular embodiments of this invention include baking soda (e.g., sodium, potassium, or aluminum bicarbonate), baking acid (e.g., sodium aluminum phosphate, monocalcium phosphate, or dicalcium phosphate), and combinations thereof.

In accordance with another particular embodiment of this invention, cocoa may comprise natural or "Dutched" chocolate from which a substantial portion of the fat or cocoa butter has been expressed or removed by solvent extraction, pressing, or other means. In a particular embodiment, it may be necessary to reduce the amount of fat in a baked good comprising chocolate because of the additional fat present in cocoa butter. In particular embodiments, it may be necessary to add larger amounts of chocolate as compared to cocoa in order to provide an equivalent amount of flavoring and coloring.

Baked goods generally also comprise caloric sweeteners, such as sucrose, high fructose corn syrup, erythritol, molasses, honey, or brown sugar. In exemplary embodiments of the baked goods provided herein, the caloric sweetener is replaced partially or totally with a compound of formula (1) or a composition comprising a compound of formula (1). Accordingly, in one embodiment a baked good comprises a compound of formula (1) or a composition comprising a compound of formula (1) in combination with a fat, water, and optionally flour. In a particular embodiment, the baked good optionally may include other natural and/or synthetic high-potency sweeteners and/or bulk sweeteners.

Dairy Products

In one embodiment, the consumable of the present invention is a dairy product that comprises a compound of formula (1). In another embodiment, the consumable of the present invention is a dairy product that comprises a composition comprising a compound of formula (1). Dairy products and processes for making dairy products suitable for use in this invention are well known to those of ordinary skill in the art. Dairy products, as used herein, comprise milk or foodstuffs produced from milk. Non-limiting examples of dairy products suitable for use in embodiments of this invention include milk, milk cream, sour cream, crème fraiche, buttermilk, cultured buttermilk, milk powder, condensed milk, evaporated milk, butter, cheese, cottage cheese, cream cheese, yogurt, ice cream, frozen custard, frozen yogurt, gelato, vla, piima, filmjolk, kajmak, kephir, viili, kumiss, airag, ice milk, casein, ayran, lassi, khoa, or combinations thereof.

Milk is a fluid secreted by the mammary glands of female mammals for the nourishment of their young. The female ability to produce milk is one of the defining characteristics of mammals and provides the primary source of nutrition for newborns before they are able to digest more diverse foods. In particular embodiments of this invention, the dairy products are derived from the raw milk of cows, goats, sheep, horses, donkeys, camels, water buffalo, yaks, reindeer, moose, or humans.

In particular embodiments of this invention, the processing of the dairy product from raw milk generally comprises the steps of pasteurizing, creaming, and homogenizing. Although raw milk may be consumed without pasteurization, it usually is pasteurized to destroy harmful microorganisms such as bacteria, viruses, protozoa, molds, and yeasts. Pasteurizing generally comprises heating the milk to a high temperature for a short period of time to substantially reduce the number of microorganisms, thereby reducing the risk of disease.

Creaming traditionally follows pasteurization step, and involves the separation of milk into a higher-fat cream layer and a lower-fat milk layer. Milk will separate into milk and cream layers upon standing for twelve to twenty-four hours. The cream rises to the top of the milk layer and may be skimmed and used as a separate dairy product. Alternatively, centrifuges may be used to separate the cream from the milk. The remaining milk is classified according to the fat content of the milk, non-limiting examples of which include whole, 2%, 1%, and skim milk.

After removing the desired amount of fat from the milk by creaming, milk is often homogenized. Homogenization prevents cream from separating from the milk and generally involves pumping the milk at high pressures through narrow tubes in order to break up fat globules in the milk. Pasteurization, creaming, and homogenization of milk are common but are not required to produce consumable dairy products. Accordingly, suitable dairy products for use in embodiments of this invention may undergo no processing steps, a single processing step, or combinations of the processing steps described herein. Suitable dairy products for use in embodiments of this invention may also undergo processing steps in addition to or apart from the processing steps described herein.

Particular embodiments of this invention comprise dairy products produced from milk by additional processing steps. As described above, cream may be skimmed from the top of milk or separated from the milk using machine-centrifuges. In a particular embodiment, the dairy product comprises sour cream, a dairy product rich in fats that is obtained by fermenting cream using a bacterial culture. The bacteria produce lactic acid during fermentation, which sours and thickens the cream. In another particular embodiment, the dairy product comprises crème fraiche, a heavy cream slightly soured with bacterial culture in a similar manner to sour cream. Crème fraiche ordinarily is not as thick or as sour as sour cream. In yet another particular embodiment, the dairy product comprises cultured buttermilk. Cultured buttermilk is obtained by adding bacteria to milk. The resulting fermentation, in which the bacterial culture turns lactose into lactic acid, gives cultured buttermilk a sour taste. Although it is produced in a different manner, cultured buttermilk generally is similar to traditional buttermilk, which is a by-product of butter manufacture.

According to other particular embodiments of this invention, the dairy products comprise milk powder, condensed milk, evaporated milk, or combinations thereof. Milk powder, condensed milk, and evaporated milk generally are produced by removing water from milk. In a particular embodiment, the dairy product comprises a milk powder comprising dried milk solids with a low moisture content. In another particular embodiment, the dairy product comprises condensed milk. Condensed milk generally comprises milk with a reduced water content and added sweetener, yielding a thick, sweet product with a long shelf-life. In yet another particular embodiment, the dairy product comprises evaporated milk. Evaporated milk generally comprises fresh, homogenized milk from which about 60% of the water has been removed, that has been chilled, fortified with additives such as vitamins and stabilizers, packaged, and finally sterilized. According to another particular embodiment of this invention, the dairy product comprises a dry creamer and a compound of formula (1) or a composition comprising a compound of formula (1).

In another particular embodiment, the dairy product provided herein comprises butter. Butter generally is made by churning fresh or fermented cream or milk. Butter generally comprises butterfat surrounding small droplets comprising mostly water and milk proteins. The churning process damages the membranes surrounding the microscopic globules of butterfat, allowing the milk fats to conjoin and to separate from the other parts of the cream. In yet another particular embodiment, the dairy product comprises buttermilk, which is the sour-tasting liquid remaining after producing butter from full-cream milk by the churning process.

In still another particular embodiment, the dairy product comprises cheese, a solid foodstuff produced by curdling milk using a combination of rennet or rennet substitutes and acidification. Rennet, a natural complex of enzymes produced in mammalian stomachs to digest milk, is used in cheese-making to curdle the milk, causing it to separate into solids known as curds and liquids known as whey. Generally, rennet is obtained from the stomachs of young ruminants, such as calves; however, alternative sources of rennet include some plants, microbial organisms, and genetically modified bacteria, fungus, or yeast. In addition, milk may be coagulated by adding acid, such as citric acid. Generally, a combination of rennet and/or acidification is used to curdle the milk. After separating the milk into curds and whey, some cheeses are made by simply draining, salting, and packaging the curds. For most cheeses, however, more processing is needed. Many different methods may be used to produce the hundreds of available varieties of cheese. Processing methods include heating the cheese, cutting it into small cubes to drain, salting, stretching, cheddaring, washing, molding, aging, and ripening. Some cheeses, such as the blue cheeses, have additional bacteria or molds introduced to them before or during aging, imparting flavor and aroma to the finished product. Cottage cheese is a cheese curd product with a mild flavor that is drained but not pressed so that some whey remains. The curd is usually washed to remove acidity. Cream cheese is a soft, mild-tasting, white cheese with a high fat content that is produced by adding cream to milk and then curdling to form a rich curd. Alternatively, cream cheese can be made from skim milk with cream added to the curd. It should be understood that cheese, as used herein, comprises all solid foodstuff produced by the curdling milk.

In another particular embodiment of this invention, the dairy product comprises yogurt. Yogurt generally is produced by the bacterial fermentation of milk. The fermentation of lactose produces lactic acid, which acts on proteins in milk to give the yogurt a gel-like texture and tartness. In particularly desirable embodiments, the yogurt may be sweetened with a sweetener and/or flavored. Non-limiting examples of flavorings include, but are not limited to, fruits (e.g., peach, strawberry, banana), vanilla, and chocolate. Yogurt, as used herein, also includes yogurt varieties with different consistencies and viscosities, such as dahi, dadih or dadiah, labneh or labaneh, bulgarian, kefir, and matsoni. In another particular embodiment, the dairy product comprises a yogurt-based beverage, also known as drinkable yogurt or a yogurt smoothie. In particularly desirable embodiments, the yogurt-based beverage may comprise sweeteners, flavorings, other ingredients, or combinations thereof.

Other dairy products beyond those described herein may be used in particular embodiments of this invention. Such dairy products are well known to those of ordinary skill in the art, non-limiting examples of which include milk, milk and juice, coffee, tea, vla, piima, filmjolk, kajmak, kephir, viili, kumiss, airag, ice milk, casein, ayran, lassi, and khoa.

According to particular embodiments of this invention, the dairy compositions also may comprise other additives. Non-limiting examples of suitable additives include sweeteners and flavorants such as chocolate, strawberry, and banana. Particular embodiments of the dairy compositions provided herein also may comprise additional nutritional supplements such as vitamins (e.g., vitamin D) and minerals (e.g., calcium) to improve the nutritional composition of the milk.

In a particularly desirable embodiment, the dairy composition comprises a compound of formula (1) or a composition comprising a compound of formula (1) in combination with a dairy product. In a particular embodiment, a compound of formula (1) is present in the dairy composition in an amount in the range of about 200 to about 20,000 weight percent of the dairy composition.

A compound of formula (1) or compositions comprising a compound of formula (1) is also suitable for use in processed agricultural products, livestock products or seafood; processed meat products such as sausage and the like; retort food products, pickles, preserves boiled in soy sauce, delicacies, side dishes; soups; snacks such as potato chips, cookies, or the like; as shredded filler, leaf, stem, stalk, homogenized leaf cured and animal feed.

Tabletop Sweetener Compositions

In one embodiment, the present invention is a tabletop sweetener comprising a compound of formula (1). The tabletop composition can further include at least one bulking agent, additive, anti-caking agent, functional ingredient or combination thereof.

Suitable "bulking agents" include, but are not limited to, maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, in accordance with still other embodiments of the invention, granulated sugar (sucrose) or other caloric sweeteners such as crystalline fructose, other carbohydrates, or sugar alcohol can be used as a bulking agent due to their provision of good content uniformity without the addition of significant calories.

As used herein, the phrase "anti-caking agent" and "flow agent" refer to any composition which assists in content uniformity and uniform dissolution. In accordance with particular embodiments, non-limiting examples of anti-caking agents include cream of tartar, calcium silicate, silicon dioxide, microcrystalline cellulose (Avicel, FMC BioPolymer, Philadelphia, Pa.), and tricalcium phosphate. In one embodiment, the anti-caking agents are present in the tabletop sweetener composition in an amount from about 0.001 to about 3% by weight of the tabletop sweetener composition.

The tabletop sweetener compositions can be packaged in any form known in the art. Non-limiting forms include, but are not limited to, powder form, granular form, packets, tablets, sachets, pellets, cubes, solids, and liquids.

In one embodiment, the tabletop sweetener composition is a single-serving (portion control) packet comprising a dry-blend. Dry-blend formulations generally may comprise powder or granules. Although the tabletop sweetener composition may be in a packet of any size, an illustrative non-limiting example of conventional portion control tabletop sweetener packets are approximately 2.5 by 1.5 inches and hold approximately 1 gram of a sweetener composition having a sweetness equivalent to 2 teaspoons of granulated sugar (~8 g). The amount of a compound of formula (1) in a dry-blend tabletop sweetener formulation can vary. In a particular embodiment, a dry-blend tabletop sweetener formulation may contain a compound of formula (1) in an amount from about 1% (w/w) to about 10% (w/w) of the tabletop sweetener composition.

Solid tabletop sweetener embodiments include cubes and tablets. A non-limiting example of conventional cubes are equivalent in size to a standard cube of granulated sugar, which is approximately 2.2×2.2×2.2 cm$^3$ and weigh approximately 8 g. In one embodiment, a solid tabletop sweetener is in the form of a tablet or any other form known to those skilled in the art.

A tabletop sweetener composition also may be embodied in the form of a liquid, wherein a compound of formula (1) is combined with a liquid carrier. Suitable non-limiting examples of carrier agents for liquid tabletop sweeteners include water, alcohol, polyol, glycerin base or citric acid base dissolved in water, and mixtures thereof. The sweetness equivalent of a tabletop sweetener composition for any of the forms described herein or known in the art may be varied to obtain a desired sweetness profile. For example, a tabletop sweetener composition may comprise a sweetness comparable to that of an equivalent amount of standard sugar. In another embodiment, the tabletop sweetener composition may comprise a sweetness of up to 100 times that of an equivalent amount of sugar. In another embodiment, the tabletop sweetener composition may comprise a sweetness of up to 90 times, 80 times, 70 times, 60 times, 50 times, 40 times, 30 times, 20 times, 10 times, 9 times, 8 times, 7 times, 6 times, 5 times, 4 times, 3 times, and 2 times that of an equivalent amount of sugar.

Beverage and Beverage Products

In one embodiment, the present invention is a beverage or beverage product comprising a compound of formula (1). In another embodiment, the present invention is a beverage or beverage comprising a composition that comprises a compound of formula (1).

As used herein a "beverage product" is a ready-to-drink beverage, a beverage concentrate, a beverage syrup, or a powdered beverage. Suitable ready-to-drink beverages include carbonated and non-carbonated beverages. Carbonated beverages include, but are not limited to, enhanced sparkling beverages, cola, lemon-lime flavored sparkling beverage, orange flavored sparkling beverage, grape flavored sparkling beverage, strawberry flavored sparkling beverage, pineapple flavored sparkling beverage, ginger-ale, soft drinks and root beer. Non-carbonated beverages include, but are not limited to fruit juice, fruit-flavored juice, juice drinks, nectars, vegetable juice, vegetable-flavored juice, sports drinks, energy drinks, enhanced water drinks, enhanced water with vitamins, near water drinks (e.g., water with natural or synthetic flavorants), coconut water, tea type drinks (e.g. black tea, green tea, red tea, oolong tea), coffee, cocoa drink, beverage containing milk components (e.g. milk beverages, coffee containing milk components, café au lait, milk tea, fruit milk beverages), beverages containing cereal extracts, smoothies and combinations thereof.

Beverage concentrates and beverage syrups are prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

Beverages comprise a liquid matrix, i.e. the basic ingredient in which the ingredients—including the compositions of the present invention—are dissolved. In one embodiment, a beverage comprises water of beverage quality as the liquid matrix, such as, for example deionized water, distilled water, reverse osmosis water, carbon-treated water, purified water, demineralized water and combinations thereof, can be used. Additional suitable liquid matrices include, but are not limited to phosphoric acid, phosphate buffer, citric acid, citrate buffer and carbon-treated water.

In one embodiment, the consumable of the present invention is a beverage that comprises a compound of formula (1).

In another embodiment, a beverage contains a composition comprising a compound of formula (1).

In a further embodiment, the present invention is a beverage product comprising a compound of formula (1).

In another embodiment, the present invention is a beverage product that contains a composition comprising a compound of formula (1).

The concentration of the compound of formula (1) in the beverage may be above, at or below the threshold sweetness or recognition concentration of the compound of formula (1).

In a particular embodiment, the concentration of the compound of formula (1) in the beverage is above the threshold sweetness or flavor recognition concentration of the compound of formula (1). In one embodiment, the concentration of the compound of formula (1) is at least about 1%, at least about 5%, at least about 10%, at least about 15%, at least about 20%, at least about 25%, at least about 30%, about least about 35%, at least about 40%, about least about 45%, at least about 50% or more above the threshold sweetness or flavor recognition concentration of the compound of formula (1).

In another particular embodiment, the concentration of the compound of formula (1) in the beverage is at or approximately the threshold sweetness or flavor recognition concentration of the compound of formula (1).

In yet another particular embodiment, the concentration of the compound of formula (1) in the beverage is below the threshold sweetness or flavor recognition concentration of the compound of formula (1). In one embodiment, the concentration of the compound of formula (1) is at least about 1%, at least about 5%, at least about 10%, at least about 15%, at least about 20%, at least about 25%, at least about 30%, about least about 35%, at least about 40%, about least about 45%, at least about 50% or more below the threshold sweetness or flavor recognition concentration of the compound of formula (1).

In one embodiment, the present invention is a beverage or beverage product that contains a compound of formula (1) in an amount ranging from about 1 ppm to about 10,000 ppm, such as, for example, from about 25 ppm to about 800 ppm. In another embodiment, a compound of formula (1) is present in a beverage in an amount ranging from about 100 ppm to about 600 ppm. In yet other embodiments, a compound of formula (1) is present in a beverage in an amount ranging from about 100 to about 200 ppm, from about 100 ppm to about 300 ppm, from about 100 ppm to about 400 ppm, or from about 100 ppm to about 500 ppm. In still another embodiment, a compound of formula (1) is present in the beverage or beverage product in an amount ranging from about 300 to about 700 ppm, such as, for example, from about 400 ppm to about 600 ppm. In a particular embodiment, a compound of formula (1) is present in a beverage an amount of about 500 ppm.

The beverage can further include at least one additional sweetener. Any of the sweeteners detailed herein can be used, including natural, non-natural, or synthetic sweeteners. These may be added to the beverage either before, contemporaneously with or after the compound of formula (1).

In one embodiment, the beverage contains a carbohydrate sweetener in a concentration from about 100 ppm to about 140,000 ppm. Synthetic sweeteners may be present in the beverage in a concentration from about 0.3 ppm to about 3,500 ppm. Natural high potency sweeteners may be present in the beverage in a concentration from about 0.1 ppm to about 3,000 ppm.

The beverage can further comprise additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, weighing agents, juice, dairy, cereal and other plant extracts, flavonoids, alcohols, polymers and combinations thereof. Any suitable additive described herein can be used.

In one embodiment, the polyol can be present in the beverage in a concentration from about 100 ppm to about 250,000 ppm, such as, for example, from about 5,000 ppm to about 40,000 ppm.

In another embodiment, the amino acid can be present in the beverage in a concentration from about 10 ppm to about 50,000 ppm, such as, for example, from about 1,000 ppm to about 10,000 ppm, from about 2,500 ppm to about 5,000 ppm or from about 250 ppm to about 7,500 ppm.

In still another embodiment, the nucleotide can be present in the beverage in a concentration from about 5 ppm to about 1,000 ppm.

In yet another embodiment, the organic acid additive can be present in the beverage in a concentration from about 10 ppm to about 5,000 ppm.

In yet another embodiment, the inorganic acid additive can be present in the beverage in a concentration from about 25 ppm to about 25,000 ppm.

In still another embodiment, the bitter compound can be present in the beverage in a concentration from about 25 ppm to about 25,000 ppm.

In yet another embodiment, the flavorant can be present in the beverage a concentration from about 0.1 ppm to about 4,000 ppm.

In a still further embodiment, the polymer can be present in the beverage in a concentration from about 30 ppm to about 2,000 ppm.

In another embodiment, the protein hydrosylate can be present in the beverage in a concentration from about 200 ppm to about 50,000.

In yet another embodiment, the surfactant additive can be present in the beverage in a concentration from about 30 ppm to about 2,000 ppm.

In still another embodiment, the flavonoid additive can be present in the beverage a concentration from about 0.1 ppm to about 1,000 ppm.

In yet another embodiment, the alcohol additive can be present in the beverage in a concentration from about 625 ppm to about 10,000 ppm.

In a still further embodiment, the astringent additive can be present in the beverage in a concentration from about 10 ppm to about 5,000 ppm.

The beverage can further contain one or more functional ingredients, detailed above. Functional ingredients include, but are not limited to, vitamins, minerals, antioxidants, preservatives, glucosamine, polyphenols and combinations thereof. Any suitable functional ingredient described herein can be used.

It is contemplated that the pH of the consumable, such as, for example, a beverage, does not materially or adversely affect the taste of the sweetener. A non-limiting example of the pH range of the beverage may be from about 1.8 to about 10. A further example includes a pH range from about 2 to about 5. In a particular embodiment, the pH of beverage can be from about 2.5 to about 4.2. On of skill in the art will understand that the pH of the beverage can vary based on the type of beverage. Dairy beverages, for example, can have pHs greater than 4.2.

The titratable acidity of a beverage comprising a compound of formula (1) may, for example, range from about 0.01 to about 1.0% by weight of beverage.

In one embodiment, the sparkling beverage product has an acidity from about 0.01 to about 1.0% by weight of the beverage, such as, for example, from about 0.05% to about 0.25% by weight of beverage.

The carbonation of a sparkling beverage product has 0 to about 2% (w/w) of carbon dioxide or its equivalent, for example, from about 0.1 to about 1.0% (w/w).

The temperature of a beverage comprising a compound of formula (1) may, for example, range from about 4° C. to about 100° C., such as, for example, from about 4° C. to about 25° C.

The beverage can be a full-calorie beverage that has up to about 120 calories per 8 oz serving.

The beverage can be a mid-calorie beverage that has up to about 60 calories per 8 oz serving.

The beverage can be a low-calorie beverage that has up to about 40 calories per 8 oz serving.

The beverage can be a zero-calorie that has less than about 5 calories per 8 oz. serving.

III. Methods of Use

The compounds and compositions of the present invention can be used to impart sweetness or to enhance the flavor or sweetness of consumables or other compositions.

In another aspect, the present invention is a method of preparing a consumable comprising (i) providing a consumable matrix and (ii) adding a compound of formula (1) to the consumable matrix to provide a consumable.

In a particular embodiment, the present invention is a method of preparing a beverage comprising (i) providing a liquid or beverage matrix and (ii) adding a compound of formula (1) to the consumable matrix to provide a beverage.

In another aspect, the present invention is a method of preparing a sweetened consumable comprising (i) providing a sweetenable consumable and (ii) adding a compound of formula (1) to the sweetenable consumable to provide a sweetened consumable.

In a particular embodiment, the present invention is a method of preparing a sweetened beverage comprising (i) providing a sweetenable beverage and (ii) adding a compound of formula (1) to the sweetenable beverage to provide a sweetened beverage.

In the above methods, the compound of formula (1) may be provided as such, or in form of a composition. When the compound of formula (1) is provided as a composition, the concentration of the compound of formula (1) in the composition is effective to provide a concentration of the compound of formula (1) that is above, at or below the threshold flavor or sweetness recognition concentration of the compound of formula (1) when the compositions is added to the consumable (e.g., the beverage). When the compound of formula (1) is not provided as a composition, it may be added to the consumable at a concentration that is above, at or below the threshold flavor or sweetness recognition concentration of the compound of formula (1).

In one embodiment, the present invention is a method for enhancing the sweetness of a consumable comprising (i) providing a consumable comprising one or more sweet ingredients and (ii) adding a compound of formula (1) to the consumable to provide a consumable with enhanced sweetness, wherein the compound of formula (1) is added to the consumable at a concentration at or below the threshold sweetness recognition concentration of the compound of formula (1). In a particular embodiment, the compound of formula (1) is added to the consumable at a concentration below the threshold sweetness recognition concentration of the compound of formula (1).

In another embodiment, the present invention is a method for enhancing the sweetness of a consumable comprising (i) providing a consumable comprising one or more sweet ingredients and (ii) adding a composition comprising compound of formula (1) to the consumable to provide a consumable with enhanced sweetness, wherein the compound of formula (1) is present in the composition in a concentration effective to provide a concentration of the compound of formula (1) at or below its threshold sweetness recognition concentration when the composition is added to the consumable. In a particular embodiment, the compound of formula (1) is present in the composition in a concentration effective to provide a concentration of the compound of formula (1) below its threshold sweetness recognition concentration when the composition is added to the consumable.

In a particular embodiment, the present invention is a method for enhancing the sweetness of a beverage comprising (i) providing a beverage comprising at least one sweet ingredient and (ii) adding a compound of formula (1) to the beverage to provide a beverage with enhanced sweetness, wherein the compound of formula (1) is added to the beverage at a concentration at or below the threshold sweetness recognition concentration of the compound of formula (1). In a particular embodiment, the compound of formula (1) is added to the consumable at a concentration below the threshold sweetness recognition concentration of the compound of formula (1).

In another particular embodiment, the present invention is a method for enhancing the sweetness of a beverage comprising (i) providing a beverage comprising one or more sweet ingredients and (ii) adding a composition comprising compound of formula (1) to the consumable to provide a beverage with enhanced sweetness, wherein the compound of formula (1) is present in the composition in a concentration effective to provide a concentration of the compound of formula (1) at or below its threshold sweetness recognition concentration when the composition is added to the beverage. In a particular embodiment, the compound of formula (1) is present in the composition in a concentration effective to provide a concentration of the compound of formula (1) below its threshold sweetness recognition concentration when the composition is added to the beverage.

In another embodiment, the present invention is method for enhancing the flavor of a consumable, comprising (i) providing a consumable comprising at least one flavor ingredient and (ii) adding a compound of formula (1) to the consumable to provide a consumable with enhanced flavor, wherein the compound of formula (1) is added to the consumable at a concentration at or below the threshold flavor recognition concentration of the compound of formula (1). In a particular embodiment, the compound of formula (1) is added to the consumable at a concentration below the threshold flavor recognition concentration of the compound of formula (1) sweetness.

In another embodiment, the present invention is a method for enhancing the flavor of a consumable comprising (i) providing a consumable comprising at least one flavor ingredient and (ii) adding a composition comprising compound of formula (1) to the consumable to provide a consumable with enhanced flavor, wherein the compound of formula (1) is present in the composition in a concentration effective to provide a concentration of the compound of formula (1) at or below its threshold flavor recognition concentration when the composition is added to the consumable. In a particular embodiment, the compound of formula (1) is present in the composition in a concentration effective to provide a concentration of the compound of formula (1) below its threshold flavor recognition concentration when the composition is added to the consumable.

In a particular embodiment, the present invention is a method for enhancing the flavor of a beverage comprising (i) providing a beverage comprising at least one flavor ingredient and (ii) adding a compound of formula (1) to the beverage to provide a beverage with enhanced flavor, wherein the compound of formula (1) is added to the beverage at a concentration at or below the threshold flavor recognition concentration of the compound of formula (1). In a particular embodiment, the compound of formula (1) is added to the consumable at a concentration below the threshold flavor recognition concentration of the compound of formula (1).

In a particular embodiment, the present invention is a method for enhancing the flavor of a beverage comprising (i) providing a beverage comprising at least one flavor ingredient and (ii) adding a composition comprising a compound of formula (1) to the beverage to provide a beverage with enhanced flavor wherein the compound of formula (1) is present in the composition in a concentration effective to provide a concentration of the compound of formula (1) at or below its threshold flavor recognition concentration when the composition is added to the beverage. In a particular embodiment, the compound of formula (1) is present in the composition in a concentration effective to provide a concentration of the compound of formula (1) below its threshold flavor recognition concentration when the composition is added to the consumable.

The present invention also includes methods of preparing sweetened compositions (e.g., sweetened consumables) and flavor enhanced compositions (e.g., flavored enhanced consumables) by adding the compounds of formula (1) or compositions comprising the compounds of formula (1) to such compositions/consumables.

IV. Method of Purification

The present invention also extends to methods of purifying the compounds of formula (1).

In one embodiment, the present invention is a method for purifying a compound of formula (1) comprising (i) passing a solution comprising mogrosides through an HPLC column and (ii) eluting fractions comprising a compound of formula (1). The HPLC column can be any suitable HPLC preparative scale column. The fractions may be eluted by adding an appropriate eluent. The eluent can be any suitable solvent or combination of solvents. In one embodiment, the eluent is water and/or acetonitrile. The method may optionally comprise additional steps, such as removal of solvents from the eluted solution to provide a concentrate comprising a compound of formula (1).

As used herein, the term "preparative HPLC" and like terms is meant an HPLC system which is capable of producing high (500 or more) microgram, milligram, or gram sized product fractions. The term "preparative" includes both preparative and semi-preparative columns, but is not intended to include analytical columns, which provide fractions in the nanogram to low microgram range.

As used herein, an "HPLC compatible detector" is a detector suitable for use in an HPLC system which is capable of providing a detectable signal upon elution of a compound peak. For example, a detector capable of generating a signal when a compound elutes from the compound is an HPLC compatible detector. Where component absorbance varies widely, it may be necessary to utilize more than one detector. A detector capable of detecting a desired component is not an "incompatible" detector due to its inability to detect a non-desired peak.

Displacement chromatography (an example of which is HPLC) is based on the principle that in a sample the balance between stationary phase (SP) and mobile phase (MP) is shifted the direction of SP. Single components of a sample displace each other like a train and the displacing agent with the greater affinity to SP pushes this train by fractions out of the column. Gas chromatography, liquid chromatography and HPLC chromatography are some of the most well known examples of displacement chromatography.

An HPLC device typically includes at least the following components: a column, packed with a suitable stationary phase, a mobile phase, a pump for forcing the mobile phase through the column under pressure, and a detector for detecting the presence of compounds eluting off of the column. The devices can optionally include a means for providing for gradient elution, although such is not necessary using the methods described herein. Routine methods and apparatus for carrying out HPLC separations are well known in the art.

Suitable stationary phases are those in which the compound of interest elutes. Preferred columns can be, and are not limited to, normal phase columns (neutral, acidic or basic), reverse phase columns (of any length alkyl chain), a synthetic crosslinked polymer columns (e.g., styrene and divinylbenzene), size exclusion columns, ion exchange columns, bioaffinity columns, and any combination thereof. The particle size of the stationary phase is within the range from a few μm to several 100 μm.

Suitable detection devices include, but are not limited to, mass spectrometers, UV detectors, IR detectors and light scattering detectors. The methods described herein use any combination of these detectors. The most preferable embodiment uses mass spectrometers and UV detectors.

HPLC Purification

In one embodiment, a preparative or semi-preparative HPLC protocol is used to purify or partially purify a mixture of mogrosides. In another embodiment, a preparative or semi-preparative HPLC protocol is used to purify or partially purify a compound of formula (1).

In one embodiment, a representative analytical HPLC protocol is correlated to a preparative or semi-preparative HPLC protocol used to purify a compound.

In another embodiment, appropriate conditions for purifying a compound of formula (1) can be worked out by route scouting a representative sample for a given analytical HPLC column, solvent system and flow rate. In yet another embodiment, a correlated preparative or semipreparative HPLC method can be applied to purify a compound of formula (1) with modifications to the purification parameters or without having to change the purification parameters.

In one embodiment, a method for purifying the compound of formula (1) of claim 1 comprises:
(a) passing a solution comprising mogrosides through a preparative HPLC; and
(b) eluting fractions comprising the compound of formula (1).

In some embodiments, the eluent (mobile phase) is selected from the group consisting of water, acetonitrile, methanol, 2-propanol, ethylacetate, dimethylformamide, dimethylsulfide, pyridine, triethylamine, formic acid, trifluoroacetic acid, acetic acid, an aqueous solution containing ammonium acetate, heptafluorobutyric acid, and any combination thereof. In another embodiment, the purification is carried out over a gradient.

In one embodiment, impurities are eluted off of the HPLC column before eluting a fraction containing mogrosides. In another embodiment, impurities are eluted off of the HPLC column before eluting a fraction containing a compound of formula (1).

The method can further include removal of solvent from the eluted solution. Removal of solvent can be performed by any known means to one of skill in the art including evaporation, distillation, vacuum drying and spray drying.

In one embodiment, the mixture being purified is a mogroside source selected from the group consisting of Luo han guo extract, by-products of other mogrosides' isolation and purification processes, a commercially available Luo han guo extract and combinations thereof In one embodiment, the mixture being purified is a fraction collected from a previous HPLC purification.

In one embodiment, mogrosides isolated from a preparative or semipreparitive HPLC protocol, are subjected to further HPLC protocols 2, 3, 4 or more times. In one embodiment, a compound of formula (1) isolated from a preparative or semipreparitive HPLC protocol, is subjected to further HPLC protocols 2, 3, 4 or more times.

In one embodiment, the method provides compounds of formula (1) in a purity greater than about 80% by weight on a dry basis, such as, for example, greater than about 85%, 90%, 95% and 97%. In a particular embodiment, the method provides compounds of formula (1) in a purity greater than about 99% by weight on a dry basis.

EXAMPLES

Instrumentation

Sciex API150 EX Single Quadrupole and Sciex API2000 Triple Quadrupole Mass Spectrometers Mass spectrometry carried out either on a Sciex API150 EX single quadrupole or a Sciex API2000 triple quadrupole mass spectrometer with a TurboIonSpray ionization source operating in negative ion mode. Sedere Sedex 75 ELS detector was used operating at 50° C. and 3.5 bar. Analysis of the samples was performed using the following method: Column: Phenomenex Synergi Hydro RP, 4.6×250 mm, 4 μm (p/n 00G-4375-E0); Column Temp: 55° C.; Mobile Phase A: $H_2O$ (0.0284% $NH_4OAc$, 0.0116% HOAc); Mobile Phase B: Acetonitrile; Flow Rate: 1.0 mL/min; Injection volume: 100 μL. Detection was by UV (210 nm), ELSD, and MSD (−ESI m/z 120-2000 or 200-1800).

Gradient:

| Time (min) | % A | % B |
|---|---|---|
| 0.0 | 90 | 10 |
| 15.0 | 75 | 25 |
| 30.0 | 10 | 90 |
| 36.0 | 10 | 90 |
| 37.0 | 90 | 10 |
| 45.0 | 90 | 10 |

Waters Premier QTof Mass Spectrometer

MS and MS/MS data were generated with a Waters Premier QTof mass spectrometer equipped with an electrospray ionization source. A sample was diluted with H20:acetonitrile (1:1) containing 0.1% formic acid and introduced via infusion using the onboard syringe pump. The dilution was adjusted to yield good s/n which occurred at an approximate concentration of 0.01 mg/mL.

Bruker Avance 500 MHz NMR

A sample was dissolved in a mixture of pyridine-$d_5$ and deuterium oxide (10:1). The NMR data were acquired on a Bruker Avance 500 MHz instrument with a 5 mm inverse detection probe. The spectrum was referenced to the residual solvent signal ($\delta_H$ 8.71, $\delta_C$ 149.9 for pyridine-$d_5$).

Agilent 1100 and Waters 600E HPLC

Semi-preparative HPLC was carried out using a Waters 600E pump connected to a Waters 996 diode-array detector and controlled by Waters Empower software. Preparative scale HPLC was carried out using an Agilent 1100 Preparative HPLC System controlled by ChemStation software.

Method 1:

Column: Phenomenex Gemini NX $C_{18}$, 250×21.2 mm, 5 μm (p/n 00G-4097-P0) with a Phenomenex guard column; UV Detection: 210 nm; Mobile Phase A: H20; Mobile Phase B: Acetonitrile; Flow Rate: 20 mL/min. The Mobile Phase gradient is provided in Table 1.

TABLE 1

Mobile Phase gradient of method 1.

| Time (min) | % A | % B |
|---|---|---|
| 0.0 | 90 | 10 |
| 15.0 | 75 | 25 |
| 20.0 | 54 | 46 |
| 21.0 | 10 | 90 |
| 26.0 | 10 | 90 |
| 26.5 | 90 | 10 |
| 31.0 | 90 | 10 |

Method 2:

Column: Phenomenex Synergi Hydro RP, 250×10 mm, 4 μm (p/n 00G-4375-N0) with a Phenomenex guard column; UV Detection: 210 nm; Mobile Phase A: $H_2O$; Mobile Phase B: Acetonitrile; Flow Rate: 5 mL/min. The Mobile Phase gradients are provided in Tables 2 and 3.

TABLE 2

Mobile Phase gradient of method (2a).

| Time (min) | % A | % B |
|---|---|---|
| 0.0 | 75 | 25 |
| 15.0 | 75 | 25 |
| 16.0 | 70 | 30 |
| 30.0 | 70 | 30 |
| 31.0 | 10 | 90 |
| 36.0 | 10 | 90 |
| 37.0 | 75 | 25 |
| 45.0 | 75 | 25 |

TABLE 3

Mobile Phase gradient of method (2b).

| Time (min) | % A | % B |
|---|---|---|
| 0.0 | 75 | 25 |
| 85.0 | 75 | 25 |
| 10.0 | 71 | 29 |
| 16.5 | 70 | 30 |
| 18.5 | 66 | 34 |
| 24.5 | 66 | 34 |
| 26.5 | 48 | 52 |
| 29.0 | 48 | 52 |
| 31.0 | 30 | 70 |
| 37.0 | 30 | 70 |
| 37.1 | 75 | 25 |
| 45.0 | 75 | 25 |

Method 3:

Column: ZIC-HIL1C, 250×10 mm, 5 μm (p/n HX 129616) with a Phenomenex guard column; UV Detection: 210 nm; Mobile Phase A: $H_2O$; Mobile Phase B: Acetonitrile; Flow Rate: 5 mL/min. The Mobile Phase gradients are provided in Tables 4 and 5.

TABLE 4

Mobile Phase gradient of method 3A.

| Time (min) | % A | % B |
|---|---|---|
| 0.0 | 15 | 85 |
| 20.0 | 15 | 85 |
| 30.0 | 95 | 5 |
| 3.0 | 95 | 5 |
| 36.0 | 15 | 85 |
| 37.0 | 15 | 85 |

TABLE 5

Mobile Phase gradient of method 3B.

| Time (min) | % A | % B |
|---|---|---|
| 0.0 | 18 | 82 |
| 15.0 | 18 | 82 |
| 20.0 | 50 | 50 |
| 21.0 | 95 | 5 |
| 25.0 | 95 | 5 |
| 26.0 | 18 | 82 |
| 31.0 | 18 | 82 |

Method 4:

Column: Waters Atlantis Prep T3, 250×10 mm, 5 μm (p/n 186003694) with a Phenomenex guard column; UV Detection: 210 nm; Mobile Phase A: $H_2O$; Mobile Phase B: Acetonitrile; Flow Rate: 5 mL/min. The Mobile Phase gradient is provided in Table 6.

TABLE 6

Mobile Phase gradient of method 4.

| Time (min) | % A | % B |
|---|---|---|
| 0.0 | 75 | 25 |
| 15.0 | 75 | 25 |
| 30.0 | 65 | 35 |
| 31.0 | 30 | 70 |
| 35.0 | 30 | 70 |
| 36.0 | 75 | 25 |
| 40.0 | 75 | 25 |

Example 1

Luo Han Guo Extracts VSPC-2973-43D and VSPC-2973-45-ML-1

Commercially available Luo han guo extracts were used, either directly or after minor processing. VSPC-2973-43D extract is a commercially available, crude Luo han guo extract containing about 80% mogrosides. VSPC-2973-43D could taken up in methanol and water or other appropriate solvents, and loaded onto the HPLC.

VSPC-2973-45-ML-1 Specifically, 15 grams of a commercially available Luo han Guo extract, containing 90% mogrosides, was added to a RB flask and with MeOH (60 ml). The solution was stirred for 15 minutes then heated to reflux. The solution was refluxed for 1 hr and cooled to RT and acetone (300 ml) added. The solution was then stirred for 24 hrs. The solution was filtered and separated the solid obtained. The filtrate was concentrated and dried, and given the name VSPC-2973-45-ML-1.

Example 1

Isolation and Purification of (2a)

Figure 1B:
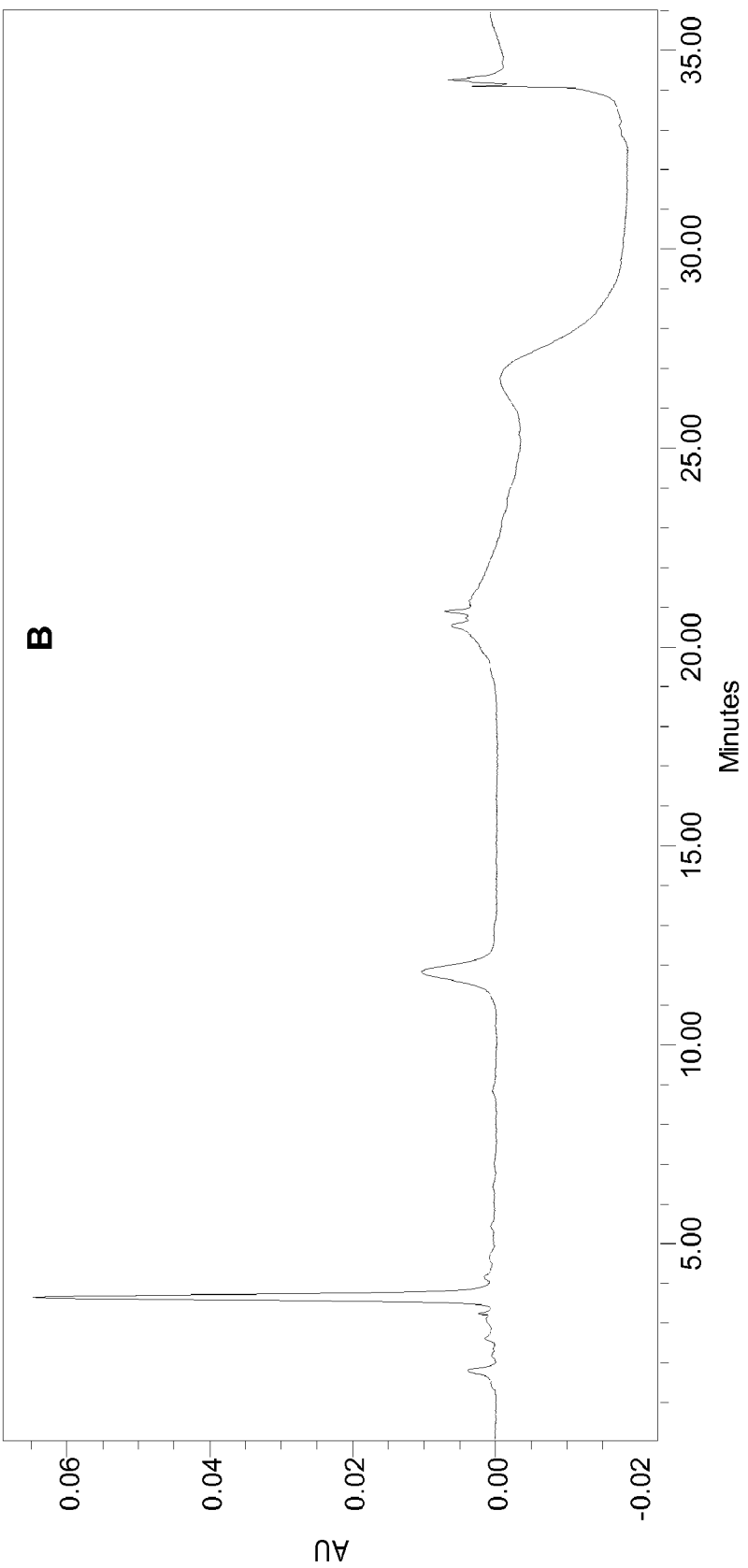

A mogrol glycoside (2a) was isolated from the extracts VSPC-2973-43D and VSPC-2973-45-ML-1. Under the LC-MS method described above method, (2a) eluted at 20.9 and 21.4 min. The ESI– mass spectrum showed the expected [M–H]– ions at mlz 1269 and 1270. First round of HPLC purifications of extracts VSPC-2973-43D and VSPC-2973-45-ML-1 were carried out using the HPLC method 1. Under this method, (2a) eluted between 19 and 21 min. Second round of purification of extracts VSPC-2973-43D and VSPC-2973-45-ML-1, were carried using the HPLC methods (2a) and (2b), respectively. Under method (2a), (2a) eluted between 19 and 23 min, and between 15 and 17 min using method (2b). FIG. 1 illustrates the HPLC chromatograms of the final purification of (2a) using HPLC method 3A. Panel A displays (2a) eluting at 11.9, and panel B shows (2a) eluting at 12.4 min. Both peaks were collected over several injections, combined, and dried by rotary evaporation under reduced pressure.

Example 2

Structural Elucidation of (2a)

Mass Spectrometry

Figure 2:
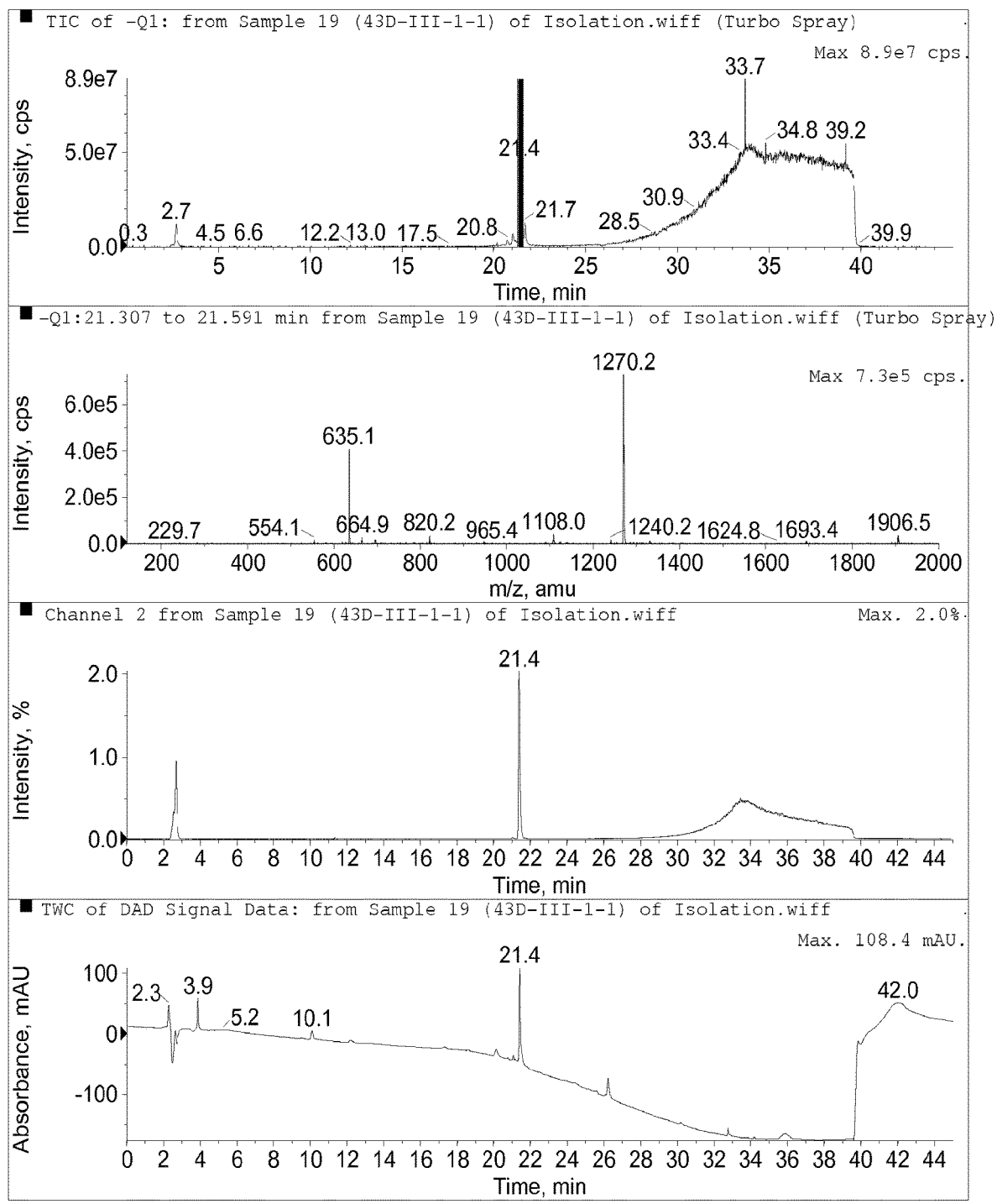
FIG. 2: LC-MS analysis of isolated sample of (2a) showing, from top to bottom, TIC, mass spectrum of the (2a) peak at 21.4 min, ELS chromatogram and UV (PDA) chromatogram.

The results of an LC-MS analysis of the isolated peak are shown in FIG. 2 and confirmed that it corresponded to (2a), eluting at 21.4 min. A single peak was observed in the TIC, UV and ELS chromatograms. The ESI+ TOF mass spectrum of (2a) showed [M+Na]$^+$ ions at m/z 1293.6447. The mass of the [M+Na]$^+$ ion was in good agreement with the molecular formula $C_{60}H_{102}O_{28}$ (calcd for $C_{60}H_{102}O_{28}Na$: 1293.6455 error: 0.8 ppm) expected for (2a). The ESI– TOF mass spectrum of the isolate of (2a) showed [M–H]$^-$ and [M+HCOOH—H]$^-$ ions at m/z 1269.6495 and 1315.6541, respectively. The mass of the [M–H]$^-$ ion was in good agreement with the molecular formula $C_{60}H_{102}O_{28}$ (calcd for $C_{60}H_{102}O_{28}$: 1269.6479, error: 1.6 mDa) expected for (2a). The MS data confirmed that (2a) has a nominal mass of 1270 Daltons with the molecular formula, $C_{60}H_{102}O_{28}$.

The MS/MS spectrum of (2a), selecting the [M–H]$^-$ ion at m/z 1269 for fragmentation, indicated the loss of 5 sugar moieties at m/z 1107.5968, 945.5433, 783.4903, 621.4369, and 459.3816. The difference of 162 mass units suggests the presence of five glucose moieties, characteristic of mogrol glycosides.

NMR Spectrometry

Figure 3:
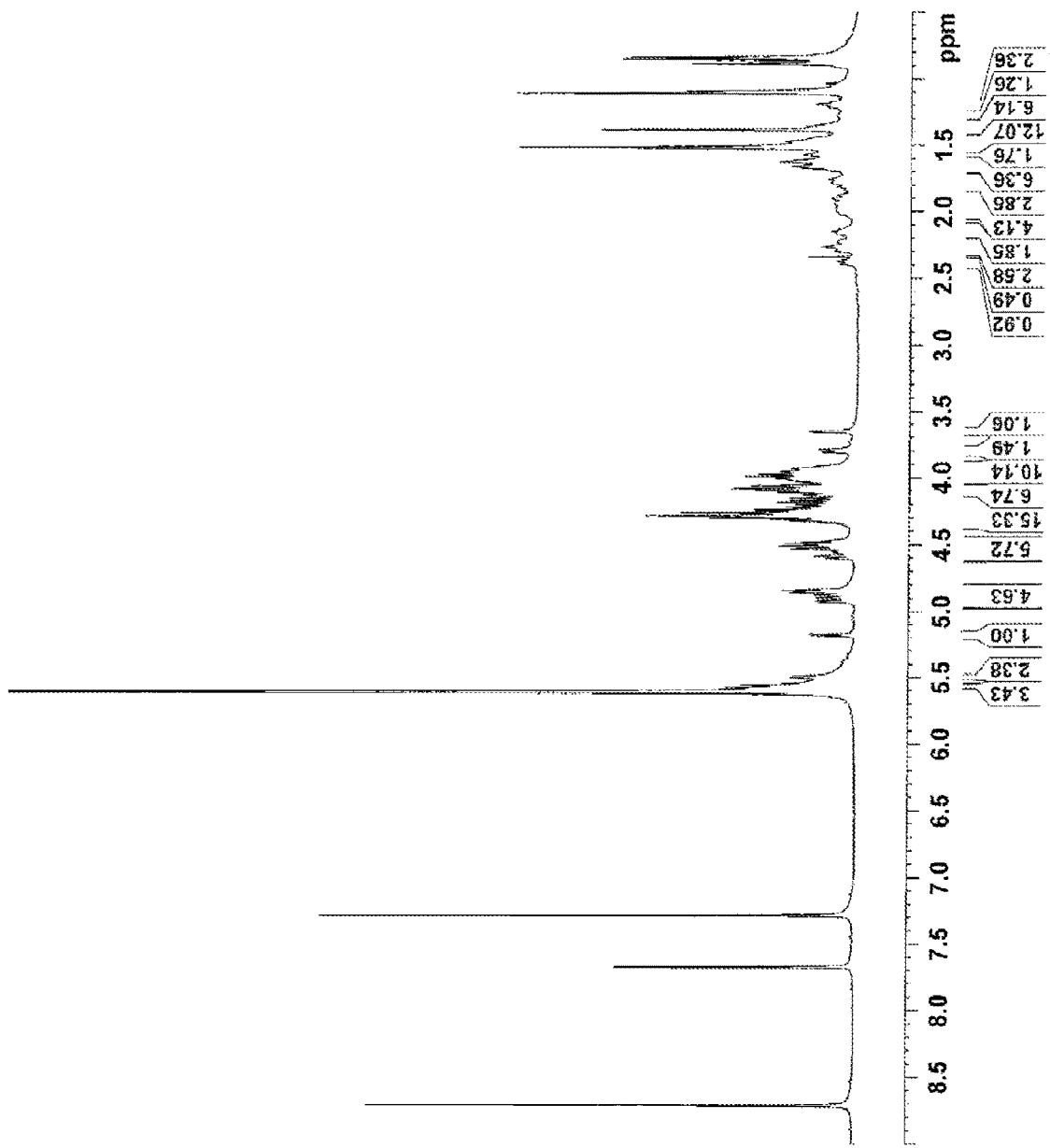
FIG. 3: 500 MHz $^1$H NMR spectrum of (2a) in pyridine-$d_5$/$D_2O$ (10:1).

A series of NMR experiments including $^1$H NMR (FIG. 3), $^1$H-$^1$H COSY, HSQC, HMBC, and HSQC-TOCSY were performed to allow assignment of (2a):

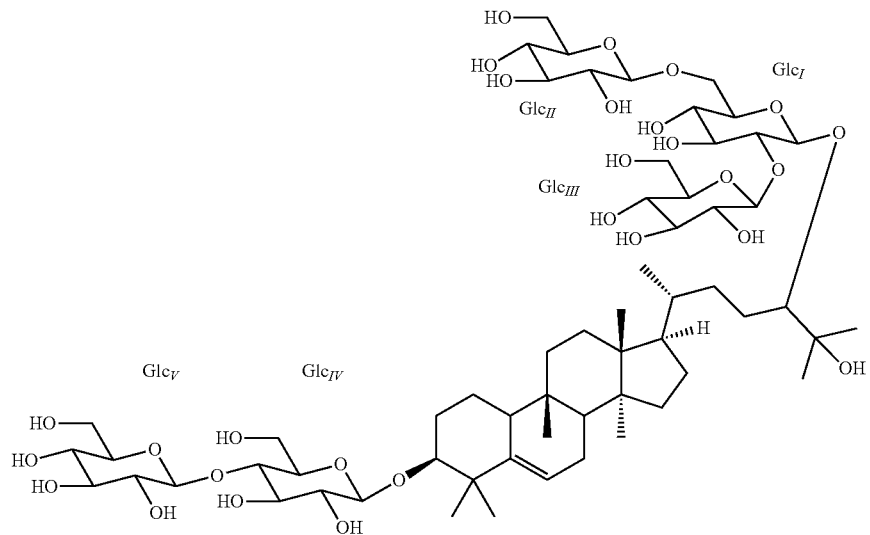

HMBC correlations were observed from the methyl protons at $\delta_H$ 1.11 and 1.52 to the olefinic carbon at $\delta_C$ 143.3, and to carbons at $\delta_C$ 87.7 and 42.4. Additional correlations of the protons at $\delta_H$ 1.11 to the carbon at $\delta_C$ 28.3 and from the protons at $\delta_H$ 1.52 to the carbon at $\delta_C$ 25.8 allowed the assignment of the geminal methyl singlets C-28 ($\delta_H$ 1.11/0c 28.3) and C-29 ($\delta_H$ 1.52/$\delta_C$ 25.8) and the methine C-3 ($\delta_H$ 3.65/$\delta_C$ 87.7) by HSQC data. The carbons at $\delta_C$ 42.4 and 143.3 did not show any HSQC correlations and they were assigned to C-4 and C-5, respectively.

COSY correlations between the H-3 proton at $\delta_H$ 3.65 and the protons at $\delta_H$ 1.91 and $\delta_H$ 2.38 allowed assignment of C-2 ($\delta_C$ 28.9) by HSQC. The proton at $\delta_H$ 2.38 showed a subsequent COSY correlation with a proton at $\delta_H$ 1.51 which is one of the methylene protons that can be assigned to C-1 ($\delta_H$ 1.51, 1.80/$\delta_C$ 22.6) by HSQC (Table 7). The H-1 protons showed additional COSY correlations to $\delta_H$ 2.28. The HSQC correlation of this proton to a carbon at $\delta_C$ 38.4 allowed its assignment as C-10.

TABLE 7

$^1$H and $^{13}$C NMR (500 and 125 MHz, (pyridine-d$_5$/D$_2$O (10:1)) assignments of the (2a) aglycone.[a, b, c]

| Position | $^{13}$C NMR | $^1$H NMR |
|---|---|---|
| 1 | 22.6 | 1.51 m |
|   |   | 1.80 m |
| 2 | 28.9 | 1.91 m |
|   |   | 2.38 d (12) |
| 3 | 87.8 | 3.65 |
| 4 | 42.4 | — |
| 5 | 143.3 | — |
| 6 | 118.9 | 5.50 m |
| 7 | 24.5 | 1.65 m |
|   |   | 2.24 m |
| 8 | 438. | 1.62 m |
| 9 | 36.6 | — |
| 10 | 38.4 | 2.28 m |
| 11 | 32.6 | 1.37 m |
|   |   | 1.58 m |
| 12 | 30.8 | 1.46 m |
|   |   | 1.65 m |
| 13 | 46.5 | — |
| 14 | 49.7 | — |
| 15 | 35.0 | 1.09 m |
|   |   | 1.19 m |

TABLE 7-continued $^1$H and $^{13}$C NMR (500 and 125 MHz, (pyridine-d$_5$/D$_2$O (10:1)) assignments of the (2a) aglycone.[a, b, c]

| Position | $^{13}$C NMR | $^1$H NMR |
|---|---|---|
| 16 | 28.4 | 1.48 m |
|   |   | 2.15 m |
| 17 | 50.9 | 1.68 m |
| 18 | 15.7 | 0.85 s |
| 19 | 28.2 | 0.88 s |
| 20 | 36.3 | 1.56 m |
| 21 | 19.2 | 1.10 d (6.3) |
| 22 | 33.4 | 1.76 m |
|   |   | 1.99 m |
| 23 | 29.1 | 1.65 m |
|   |   | 1.93 m |
| 24 | 92.6 | 3.80 d (8.9) |
| 25 | 73.2 | — |
| 26 | 26.9 | 1.39 s |
| 27 | 24.5 | 1.51 s |
| 28 | 28.3 | 1.11 s |
| 29 | 25.8 | 1.52 s |
| 30 | 18.2 | 0.83 s |

[a] assignments made on the basis of COSY, HSQC, HMBC, TOCSY and HSQC-TOCSY correlations;
[b] Chemical shift values are in $\delta$ (ppm);
[c] Coupling constants are in Hz.

A third methyl singlet, observed at $\delta_H$ 0.88, showed HMBC correlations to C-10 and to carbons at $\delta_C$ 32.6, 36.6, and 43.8. Therefore, C-19 ($\delta_H$ 0.88/$\delta_C$ 28.2) could be assigned by HSQC. HSQC correlations also allowed the assignment of C-8 ($\delta_H$ 1.62/$\delta_C$ 43.8) and C-11 ($\delta_H$ 1.37, 1.58/$\delta_C$ 32.6), while the carbon at $\delta_C$ 36.6 is quaternary and should correspond to C-9. COSY correlations were observed between H-8 and a proton at $\delta_H$ 2.24 which subsequently correlates with a proton at $\delta_H$ 5.50 establishing a spin system H-6/H-7/H-8 that allows the assignment of C-7 ($\delta_H$ 1.65, 2.24/$\delta_C$ 24.5) and C-6 ($\delta_H$ 5.50/$\delta_C$ 118.9) through HSQC correlations. One of the H-11 protons at $\delta_H$ 1.37 shows also a COSY correlations with a proton at $\delta_H$ 1.65 which belongs to a methylene ($\delta_H$ 1.46, 1.65/$\delta_C$ 30.8) as corroborated by HSQC correlations, and consequently assigned to C-12.

A fourth methyl singlet that resonates at $\delta_H$ 0.85 showed HMBC correlations to C-12 and to carbons at $\delta_C$ 46.5, 49.7, and 50.9. These correlations allowed the assignment of C-18 ($\delta_H$ 0.85/$\delta_C$ 15.7) and C-17 ($\delta_H$ 1.68/$\delta_C$ 50.9) by HSQC. The quaternary carbons at $\delta_C$ 46.5 and 49.7 correspond to C-13 and C-14 but they could be interchanged since there are no other HMBC correlations that could unambiguously assign them.

Likewise, a fifth methyl singlet at $\delta_H$ 0.83 also showed correlations to C-13 and C-14, in addition to correlations to C-8 and a carbon at $\delta_C$ 35.0. The HSQC correlations of this carbon indicate that it is a methylene unit that is linked to protons at $\delta_H$ 1.09 and 1.19. These protons show COSY correlations to a proton at $\delta_H$ 2.15 which subsequently correlates to H-17 and to a proton at $\delta_H$ 1.48. All this information, together with analysis of HSQC data allowed the assignment of C-30 ($\delta_H$ 0.83/$\delta_C$ 18.2), C-15 ($\delta_H$ 1.09, 1.19/$\delta_C$ 35.0) and C-16 ($\delta_H$ 1.48, 2.15/$\delta_C$ 28.4).

A sixth methyl was observed as a doublet at $\delta_H$ 1.10 and it showed HMBC correlations to carbons at $\delta_C$ 33.4, 36.3, and C-17. These methyl protons also showed COSY correlations to a proton at $\delta_H$ 1.56 which allowed the assignment of C-21 ($\delta_H$ 1.10/$\delta_C$ 19.2) and C-20 ($\delta_H$ 1.56/$\delta_C$ 36.3) by HSQC.

A COSY correlation of H-20 to a proton at $\delta_H$ 1.99 allowed assigning of C-22 ($\delta_H$ 1.76, 1.99/$\delta_C$ 33.4) by HSQC. Subsequent COSY correlations of the proton at $\delta_H$ 1.99 to the proton at $\delta_H$ 1.65, which in turn correlates to the proton at $\delta_H$ 3.80, also confirmed the assignment of C-23 ($\delta_H$ 1.65, 1.93/$\delta_C$ 29.1) and C-24 ($\delta_H$ 3.80/$\delta_C$ 92.6) by HSQC.

The remaining two methyl singlets that resonate at $\delta_H$ 1.39 and 1.51 showed HMBC correlations to each other at $\delta_C$ 24.5, and 26.9. Additional HMBC correlations of these methyl protons to C-24 and to a carbon at $\delta_C$ 73.2 allowed the assignment of C-26 ($\delta_H$ 1.39/$\delta_C$ 26.9) and C-27 ($\delta_H$ 1.51/$\delta_C$ 24.5) by HSQC. These data indicate that these methyl groups are geminal and their assignments are interchangeable since they should be linked to the achiral carbon at $\delta_C$ 73.2, which in turn could be assigned to C-25.

An analysis of the HSQC data for (2b) confirmed the presence of five anomeric protons that were observed in the $^1$H NMR spectrum at $\delta_H$ 5.57 ($\delta_C$ 104.8), 5.18 ($\delta_C$ 104.8), 4.92 ($\delta_C$ 103.8), 4.85 ($\delta_C$ 104.6), and 4.84 ($\delta_C$ 106.7).

The anomeric proton observed at $\delta_H$ 4.84 showed an HMBC correlation to C-3 which indicated that it belongs to Glc$_{IV}$. This proton also showed a COSY correlation to a proton at $\delta_H$ 3.98 which was assigned as Glc$_{IV}$ H-2 ($\delta_H$ 3.98/$\delta_C$ 74.8) by HSQC data. Due to overlap in the data the COSY spectrum did not allow further assignments in this sugar. Selective irradiation of the Glc$_{IV}$ anomeric proton with several different mixing times in a series of 1-D TOCSY experiments also affected the anomeric proton at $\delta_H$ 4.85 which belong to another sugar unit. Therefore, tentative assignment of Glc$_{IV}$ was performed by analysis of the TOCSY, HSQC, and HSQC-TOCSY data, Glc$_{IV}$ H-2 is clearly observed in the TOCSY data at 20 msec, together with $\delta_H$ 4.06, the H-2 of the alternative sugar. Additional TOCSY analysis suggests that the protons at $\delta_H$ 4.27-4.28 correspond to H-3 in both Glc$_{IV}$ and in another sugar unit. However, the prominence in those signals even at 40 and 60 msec implies that C-4 may also be linked to these protons as well. Further analysis of the TOCSY data revealed additional protons at $\delta_H$ 4.18, 3.94, and 3.92 and 4.50 at increasing mixing times. The proton at $\delta_H$ 4.50 is part of an oxygenated methylene and can be assigned to Glc$_{IV}$ C-6 ($\delta_H$ 4.30, 4.50/$\delta_C$ 62.2) by HSQC. The proton at $\delta_H$ 4.50 showed COSY correlations to protons at $\delta_H$ 3.94 and 3.92. HSQC-TOCSY data allowed assignment of C-5 ($\delta_H$ 3.92/$\delta_C$ 76.2), while the proton at $\delta_H$ 3.94 belongs to the another sugar. It is not possible to assign unambiguously Glc$_{IV}$ C-3 or C-4 to ($\delta_H$ 4.27/$\delta_C$ 81.4) or ($\delta_H$ 4.27/$\delta_C$ 76.5) due to overlap. However, the observation of an HMBC correlation to the carbon at $\delta_C$ 81.4 from an anomeric proton at $\delta_H$ 5.57 indicates the connectivity of Glc$_{IV}$ to another sugar. Literature searches for mogrosides show only one reference about the connectivity of Glc$_{IV}$ to another sugar, and it is through C-4 (J. Carb, Chem, 2011, 30, 16-26). Based on this information, we propose the assignment of Glc$_{IV}$ C-4 ($\delta_H$ 4.27/$\delta_C$ 81.4) and Glc$_{IV}$ C-3 ($\delta_H$ 4.27/$\delta_C$ 76.5).

The anomeric proton at $\delta_H$ 5.57 that connects to Glc$_{IV}$ C-4 could be assigned to Glc$_V$ H-1 ($\delta_H$ 5.57/$\delta_C$ 104.8) by HSQC, COSY correlations of this proton to $\delta_H$ 4.10 allowed the assignment of C-2 ($\delta_H$ 4.10/$\delta_C$ 75.8). A series of 1-D TOCSY experiments selecting the anomeric proton, together with the HSQC and HSQC-TOCSY data allowed assignment of Glc$_V$ C-3 ($\delta_H$ 4.23/$\delta_C$ 77.8), C-4 ($\delta_H$ 4.07/$\delta_C$ 72.2), C-5 ($\delta_H$ 4.00/$\delta_C$ 78.3), and C-6 ($\delta_H$ 4.31, 4.59/$\delta_C$ 63.2) by HSQC.

There is no evidence of additional connectivities to Glc$_{IV}$ or Glc$_V$, and among the three remaining glucose units, only the anomeric protons at $\delta_H$ 5.18 ($\delta_C$ 104.8) and 4.85 ($\delta_C$ 104.6) show HMBC correlations to carbons at $\delta_C$ 81.2 and 70.0, respectively. These carbons do not belong to the aglycone, therefore, the anomeric proton at $\delta_H$ 4.92 ($\delta_C$ 103.8) can be assigned as Glc$_I$ H-1, and has to be connected to C-24. This connectivity is supported by a similar connectivity reported for Mogroside IVa, V, and VI (J. Carb. Chem. 2011, 30, 16-26). In all those cases, Glc$_I$ H-1 is connected to C-24.

Glc$_I$ H-1 showed a COSY correlation with a proton at $\delta_H$ 4.27. A series of 1-D TOCSY experiments selecting this anomeric proton, together with the HSQC and HSQC-TOCSY data allowed assignment of Glc$_{IV}$ C-2 ($\delta_H$ 4.27/$\delta_C$ 81.2), C-3 ($\delta_H$ 4.29/$\delta_C$ 78.4), C-4 ($\delta_H$ 3.97/$\delta_C$ 71.1), and C-5 ($\delta_H$ 4.09/$\delta_C$ 76.2). An additional COSY correlation of H-5 to a proton at $\delta_H$ 4.88 allowed the assignment of C-6 ($\delta_H$ 3.97, 4.88/$\delta_C$ 70.0) by HSQC.

An HMBC correlation of the anomeric proton at $\delta_H$ 4.85 to Glc$_I$ C-6 allowed its assignment as Glc$_{II}$ H-1. Selective irradiation of this proton with several different mixing times in a series of 1-D TOCSY experiments also affected the anomeric proton Glc$_{II}$ H-1 as described before for Glc$_{IV}$. Since the assignment of Glc$_{II}$ C-2 ($\delta_H$ 4.06/$\delta_C$ 75.0) was already established and the full study of the HSQC-TOCSY of Glc$_{IV}$ H-1 was completed, analysis of the TOCSY, HSQC, and HSQC-TOCSY data allowed the assignment of Glc$_{II}$ C-3 ($\delta_H$ 4.28/$\delta_C$ 77.6), C-4 ($\delta_H$ 4.18/$\delta_C$ 71.4), and C-5 ($\delta_H$ 3.94/$\delta_C$ 78.2). An additional COSY correlation of H-5 to a proton at $\delta_H$ 4.50 allowed the assignment of C-6 ($\delta_H$ 4.30, 4.50/$\delta_C$ 62.2) by HSQC.

An HMBC correlation of the anomeric proton at $\delta_H$ 5.18 allowed its assignment as Glc$_{III}$ H-1. This anomeric proton showed a COSY correlation with a proton at $\delta_H$ 4.08. Analysis of 1-D TOCSY experiments performed by selecting this anomeric proton, together with the analysis of HSQC and HSQC-TOCSY data allowed the assignment of Glc$_{III}$ C-2 ($\delta_H$ 4.08/$\delta_C$ 74.7), C-3 ($\delta_H$ 4.27/$\delta_C$ 77.8), C-4 ($\delta_H$ 4.16/$\delta_C$ 71.4), C-5 ($\delta_H$ 4.02/$\delta_C$ 78.3), and C-6 ($\delta_H$ 4.23, 4.53/$\delta_C$ 62.2).

A summary of the $^1$H and $^{13}$C chemical shifts for the glycoside at C-3 are found in Table 8.

TABLE 8

$^1$H and $^{13}$C NMR (500 and 125 MHz, pyridine-d$_5$ D$_2$O (10:1)) assignments of the (2a) C-3 glycoside.[a, b, c]

| Position | $^{13}$C NMR | $^1$H NMR |
|---|---|---|
| Glc$_{II}$-1 | 106.7 | 4.84 d (7.7) |
| Glc$_{II}$-2 | 74.8 | 3.98 m |
| Glc$_{II}$-3 | 76.5 | 4.27 m |
| Glc$_{II}$-4 | 81.4 | 4.27 m |
| Glc$_{II}$-5 | 76.2 | 3.92 m |
| Glc$_{II}$-6 | 62.1 | 4.30 m |
|  |  | 4.50 m |
| Glc$_{I'}$-1 | 104.8 | 5.57 d (8.1) |
| Glc$_{I'}$-2 | 75.8 | 4.10 m |
| Glc$_{I'}$-3 | 77.8 | 4.23 m |
| Glc$_{I'}$-4 | 72.2 | 4.07 m |
| Glc$_{I'}$-5 | 78.3 | 4.00 m |
| Glc$_{I'}$-6 | 63.2 | 4.31 m |
|  |  | 4.59 m |

[a] assignments made on the basis of COSY, HSQC, HMBC, TOCSY and HSQC-TOCSY correlations;
[b] Chemical shift values are in δ (ppm);
[c] Coupling constants are in Hz.

A summary of the $^1$H and $^{13}$C chemical shifts for the glycoside at C-24 are found in Table 9.

TABLE 9

$^1$H and $^{13}$C NMR (500 and 125 MHz, (pyridine-d$_5$/D$_2$O (10:1)) assignments of the (2a) C-24 glycoside.[a, b, c]

| Position | $^{13}$C NMR | $^1$H NMR |
|---|---|---|
| Glc$_I$-1 | 103.8 | 4.92 d (6.8) |
| Glc$_I$-2 | 81.2 | 4.27 m |
| Glc$_I$-3 | 78.4 | 4.29 m |
| Glc$_I$-4 | 71.1 | 3.97 m |
| Glc$_I$-5 | 76.2 | 4.09 m |
| Glc$_I$-6 | 70.0 | 3.97 m |
|  |  | 4.88 d (9.4) |
| Glc$_{II}$-1 | 104.6 | 4.85 d (7.7) |
| Glc$_{II}$-2 | 75.0 | 4.06 m |
| Glc$_{II}$-3 | 77.6 | 4.28 m |
| Glc$_{II}$-4 | 71.4 | 4.18 m |
| Glc$_{II}$-5 | 78.2 | 3.94 m |
| Glc$_{II}$-6 | 62.2 | 4.30 m |
|  |  | 4.50 m |
| Glc$_{III}$-1 | 104.8 | 5.18 d (7.7) |
| Glc$_{III}$-2 | 74.7 | 4.08 m |
| Glc$_{III}$-3 | 77.8 | 4.27 m |
| Glc$_{III}$-4 | 71.4 | 4.16 m |
| Glc$_{III}$-5 | 78.3 | 4.02 m |
| Glc$_{III}$-6 | 62.2 | 4.23 m |
|  |  | 4.53 m |

[a] assignments made on the basis of COSY, HSQC, HMBC, TOCSY and HSQC-TOCSY correlations;
[b] Chemical shift values are in δ (ppm);
[c] Coupling constants are in Hz.

Example 3

Isolation and Purification of (2b)

Figure 4:
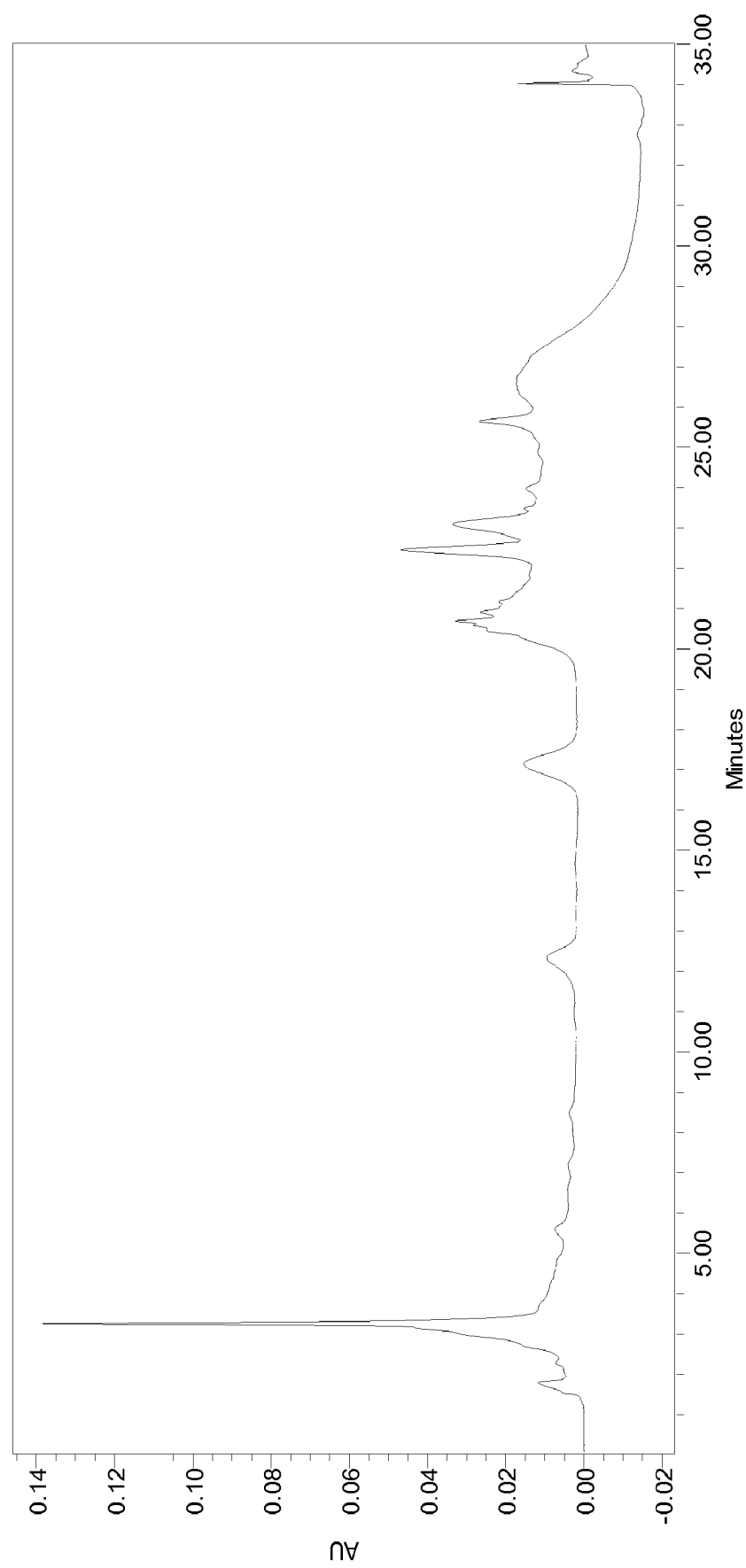
FIG. 4: HPLC chromatogram for the final purification of extract VSPC-2973-43D.

A mogrol glycoside (2b) was isolated from the extract VSPC-2973-43D. Under LC-MS method described above method, (2b) eluted at 20.5 min. The ESI− mass spectrum showed the expected [M−H]− ions at m/z 1269. First round of purification of extract VSPC-2973-43D was carried out using the HPLC method 1. Under this method, (2b) eluted between 19 and 21 min. Second round of purification of extract VSPC-2973-43D was carried out using the HPLC method 2 A. Under this method (2b) eluted between 19 and 23 min. FIG. 4 illustrates the HPLC chromatograms of the final purification of (2b) using HPLC method 3A. Compound (2b) elutes at 17.1 min under this method. This peak was collected over several injections and dried by rotary evaporation under reduced pressure.

Example 4

Structural Elucidation of (2b)

Mass Spectrometry

Figure 5:
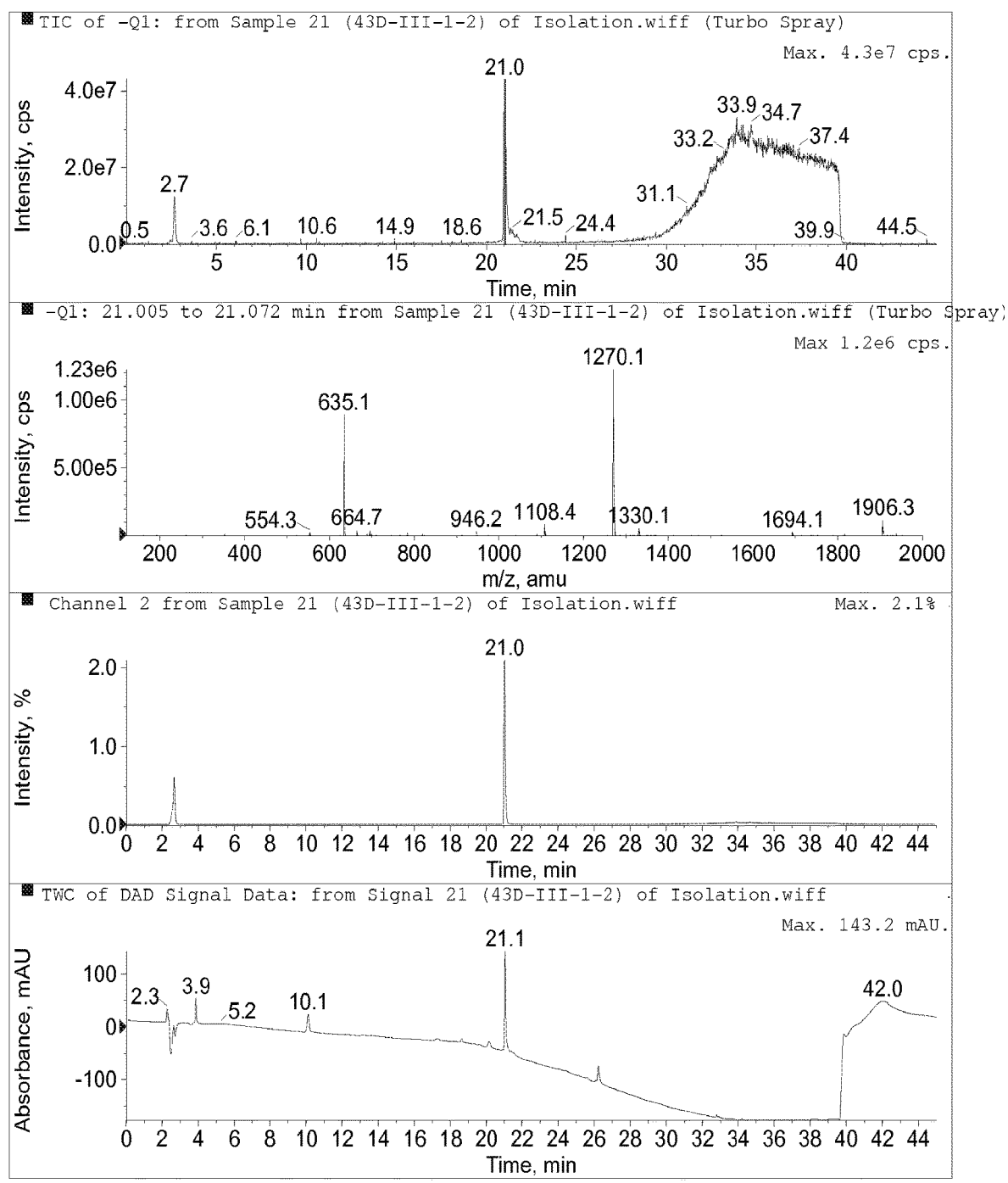
FIG. 5: LC-MS analysis of isolated sample of (2b) showing, from top to bottom, TIC, mass spectrum of the (2b) peak at 21.0 min, ELS chromatogram and UV (PDA) chromatogram.

The results of an LC-MS analysis of the isolated peak are shown in FIG. 5 and confirmed that it corresponded to (2b). A single peak was observed in the TIC, UV and ELS chromatograms. The ESI+ TOF mass spectrum of (2b) showed [M+H]$^+$ and [M+Na]$^-$ ions at m/z 1271.6649 and 1293.6465, respectively. The mass of the [M+H]$^+$ ion was in good agreement with the molecular formula $C_{60}H_{102}O_{28}$ (calcd for $C_{60}H_{103}O_{28}$: 1271.6636 error: 1.3 ppm) expected for (2b). The ESI− TOF mass spectrum of the isolate of (2b) showed [M−H]$^-$ and [M+HCOOH−H]$^-$ ions at m/z 1269.6455 and 1315.6494, respectively. The mass of the [M−H]$^-$ ion was in good agreement with the molecular formula $C_{60}H_{102}O_{28}$ (calcd for $C_{60}H_{101}O_{28}$: 1269.6479, error: 2.4 mDa) expected for (2b). The MS data confirmed that (2b) has a nominal mass of 1270 Daltons with the molecular formula, $C_{60}H_{102}O_{28}$.

The MS/MS spectrum of (2b), selecting the [M−H]$^-$ ion at m/z 1269 for fragmentation, indicated the loss of 5 sugar moieties at m/z 1107.5968, 945.5433, 783.4903, 621.4369, and 459.3816. The difference of 162 mass units suggests the presence of five glucose moieties, characteristic of mogrol glycosides.

NMR Spectrometry

Figure 6:
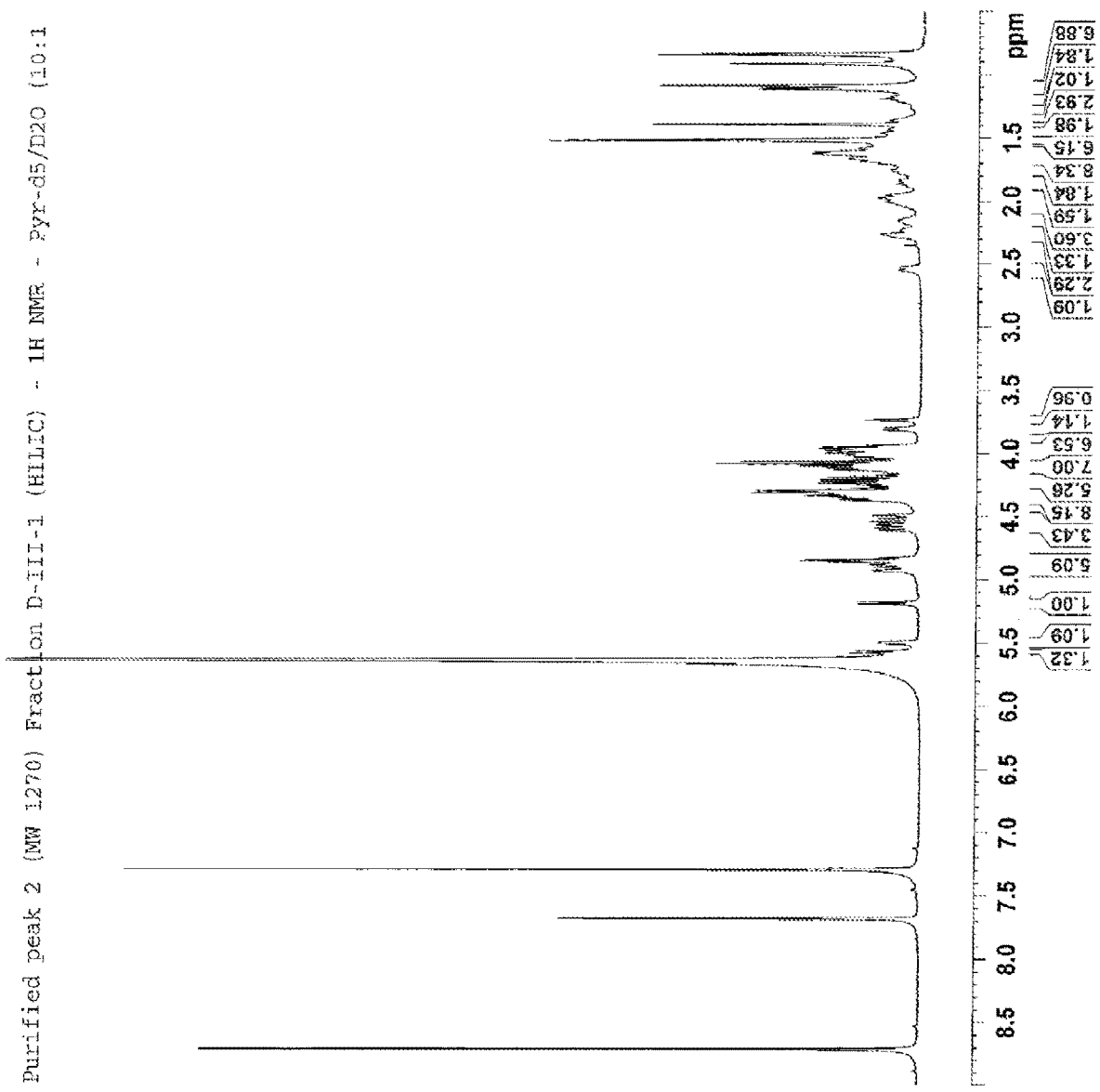
FIG. 6: 500 MHz $^1$H NMR spectrum of (2b) in pyridine-$d_5$/$D_2O$ (10:1).

A series of NMR experiments including $^1$H NMR (FIG. 6), $^1$H-$^1$H COSY, HSQC, HMBC, and HSQC-TOCSY were performed to allow assignment of (2b).

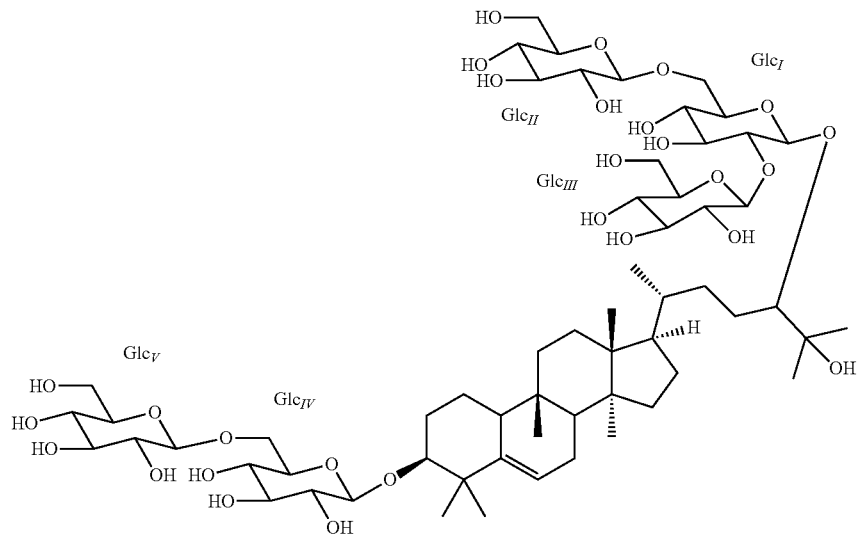

HMBC correlations were observed from the methyl protons at $\delta_H$ 1.09 and 1.51 to the olefinic carbon at $\delta_C$ 143.4, and to carbons at $\delta_C$ 87.5 and 41.9. Additional correlations of the protons at $\delta_H$ 1.09 to the carbon at $\delta_C$ 28.3 and from the protons at $\delta_H$ 1.51 to the carbon at $\delta_C$ 25.6 allowed the assignment of the germinal methyl singlets C-28 ($\delta_H$ 1.09/$\delta_C$ 28.2) and C-29 ($\delta_H$ 1.51/$\delta_C$ 25.6) and the methine C-3 ($\delta_H$ 3.73/$\delta_C$ 87.5) by HSQC data. The carbons at $\delta_C$ 41.9 and 143.4 did not show any HSQC correlations and they were assigned to C-4 and C-5, respectively.

COSY correlations between the H-3 proton at $\delta_H$ 3.73 and the protons at $\delta_H$ 1.97 and $\delta_H$ 2.54 allowed assignment of C-2 ($\delta_C$ 28.9) by HSQC. The proton at $\delta_H$ 2.54 showed subsequent COSY correlations with protons at $\delta_H$ 1.62 and 1.85 which can be assigned to C-1 ($\delta_H$ 1.62, 1.85/$\delta_C$ 22.6) by HSQC (Table 10). The H-1 protons showed additional COSY correlations to $\delta_H$ 2.27. The HSQC correlation of this proton to a carbon at $\delta_C$ 38.3 allowed its assignment as C-10.

A third methyl singlet, observed at $\delta_H$ 0.91, showed HMBC correlations to C-10 and to carbons at $\delta_C$ 32.4, 35.1, and 43.6. Therefore, C-19 ($\delta_H$ 0.91/$\delta_C$ 28.1) could be assigned by HSQC. HSQC correlations also allowed the assignment of C-8 ($\delta_H$ 1.62/$\delta_C$ 43.6) and C-11 ($\delta_H$ 1.36, 1.59/$\delta_C$ 32.4), while the carbon at $\delta_C$ 35.1 is quaternary and should correspond to C-9. COSY correlations were observed between H-8 and a proton at $\delta_H$ 2.24 which subsequently correlates with a proton at $\delta_H$ 5.49 establishing a spin system H-6/H-7/H-8 that allows the assignment of C-7 ($\delta_H$ 1.64, 2.24/$\delta_C$ 24.4) and C-6 ($\delta_H$ 5.49/$\delta_C$ 118.8) through HSQC correlations. One of the H-11 protons at $\delta_H$ 1.36 shows also a COSY correlations with a proton at $\delta_H$ 1.62 which belongs to a methylene ($\delta_H$ 1.45, 1.62/$\delta_C$ 30.6) as corroborated by HSQC correlations, and consequently assigned to C-12.

A fourth methyl singlet that resonates at $\delta_H$ 0.85 showed HMBC correlations to C-12 and to carbons at $\delta_c$ 46.7, 49.4, and 50.8. These correlations allowed the assignment of C-18 ($\delta_H$ 0.85/$\delta c$ 15.5) and C-17 ($\delta_H$ 1.69/$\delta c$ 50.8) by HSQC. The quaternary carbons at $\delta_c$ 46.7 and 49.4 correspond to C-13 and C-14 but they could be interchanged since there are no other HMBC correlations that could unambiguously assign them.

Likewise, a fifth methyl singlet at $\delta_H$ 0.84 also showed HMBC correlations to C-13 and C-14, in addition to correlations to C-8 and a carbon at $\delta_c$ 34.9. The HSQC correlations of this carbon indicate that it is a methylene unit that is linked to protons at $\delta_H$ 1.09 and 1.19. These protons show COSY correlations to a proton at $\delta_H$ 2.16 which subsequently correlates to H-17 and to a proton at $\delta_H$ 1.49. All this information, together with analysis of HSQC data allowed the assignment of C-30 ($\delta_H$ 0.84/$\delta c$ 18.0), C-15 ($\delta_H$ 1.09, 1.19/$\delta c$ 34.9) and C-16 ($\delta_H$ 1.49, 2.16/$\delta_c$ 28.2).

A sixth methyl was observed as a doublet at $\delta_H$ 1.11 and it showed HMBC correlations to carbons at $\delta_C$ 33.3, 36.3, and C-17. These methyl protons also showed COSY correlations to a proton at $\delta_H$ 1.57 which allowed the assignment of C-21 ($\delta_H$ 1.11/$\delta c$ 19.1) and C-20 ($\delta_H$ 1.57/$\delta c$ 36.2) by HSQC. A COSY correlation of H-20 to a proton at $\delta_H$ 2.00 allowed assigning of C-22 ($\delta_H$ 1.76, 2.00/$\delta_C$ 33.3) by HSQC. Subsequent COSY correlations of the proton at $\delta_H$ 2.00 to the proton at $\delta_H$ 1.66, which in turn correlates to the proton at $\delta_H$ 3.80, also confirmed the assignment of C-23 ($\delta_H$ 1.66, 1.97/$\delta_C$ 29.0) and C-24 ($\delta_H$ 3.80/$\delta_C$ 92.4) by HSQC.

The remaining two methyl singlets that resonate at $\delta_H$ 1.39 and 1.52 showed HMBC correlations to each other at $\delta_C$ 24.4, and 26.7. Additional HMBC correlations of these methyl protons to C-24 and to a carbon at $\delta_C$ 72.9 allowed the assignment of C-26 ($\delta_H$ 1.39/$\delta_C$ 26.7) and C-27 ($\delta_H$ 1.52/$\delta_C$ 24.4) by HSQC. These data indicate that these methyl groups are geminal and their assignments are interchangeable since they should be linked to the achiral carbon at $\delta_C$ 72.9, which in turn could be assigned to C-25.

A summary of the $^1$H and $^{13}$C chemical shifts for the aglycone are found in Table 10.

TABLE 10

$^1$H and $^{13}$C NMR (500 and 125 MHz, (pyridine-$d_5$/D$_2$O (10:1)) assignments of the (2b) aglycone.[a, b, c]

| Position | $^{13}$C NMR | $^1$H NMR |
|---|---|---|
| 1 | 22.6 | 1.62 m |
|   |      | 1.85 m |
| 2 | 28.9 | 1.97 m |
|   |      | 2.54 d (12) |
| 3 | 87.5 | 3.73 m |
| 4 | 41.9 | — |
| 5 | 143.4 | — |

TABLE 10-continued $^1$H and $^{13}$C NMR (500 and 125 MHz, (pyridine-$d_5$/$D_2$O (10:1)) assignments of the (2b) aglycone.[a, b, c]

| Position | $^{13}$C NMR | $^1$H NMR |
|---|---|---|
| 6 | 118.8 | 5.49 d (4.2) |
| 7 | 24.4 | 1.64 m |
|   |      | 2.24 m |
| 8 | 43.6 | 1.62 m |
| 9 | 35.1 | — |
| 10 | 38.3 | 2.27 m |
| 11 | 32.4 | 1.36 m |
|    |      | 1.59 m |
| 12 | 30.6 | 1.45 m |
|    |      | 1.62 m |
| 13 | 46.7 | — |
| 14 | 49.4 | — |
| 15 | 34.9 | 1.09 m |
|    |      | 1.19 m |
| 16 | 28.2 | 1.49 m |
|    |      | 2.16 m |
| 17 | 50.8 | 1.69 |
| 18 | 15.5 | 0.85 s |
| 19 | 28.1 | 0.91 s |
| 20 | 36.2 | 1.57 m |
| 21 | 19.1 | 1.11 d (6.0) |
| 22 | 33.3 | 1.76 m |
|    |      | 2.00 m |
| 23 | 29.0 | 1.66 m |
|    |      | 1.97 m |
| 24 | 92.4 | 3.80 d (9.0) |
| 25 | 72.9 | — |
| 26 | 26.7 | 1.39 s |
| 27 | 24.4 | 1.52 s |
| 28 | 28.2 | 1.09 s |
| 29 | 25.6 | 1.51 s |
| 30 | 18.0 | 0.84 s |

[a] assignments made on the basis of COSY, HSQC, HMBC, TOCSY and HSQC-TOCSY correlations;
[b] Chemical shift values are in δ (ppm);
[c] Coupling constants are in Hz.

An analysis of the HSQC data for (2a) confirmed the presence of five anomeric protons that were observed in the $^1$H NMR spectrum at $\delta_H$ 5.57 ($\delta_C$ 104.6), 5.18 ($\delta_C$ 104.9), 4.93 ($\delta_C$ 103.7), 4.85 ($\delta_C$ 104.5), and 4.85 ($\delta_C$ 106.6).

There are two anomeric protons observed at $\delta_H$ 4.85. They showed COSY correlations to protons at $\delta_H$ 3.95 and 4.06 but they could not be assigned to a particular sugar. However, these anomeric protons could be distinguished in the HSQC, HMBC, and HSQC-TOCSY spectra ($\delta_H$ 4.845 and 4.850). The proton at $\delta_H$ 4.845, showed an HMBC correlation to C-3 which allowed its assignment as $Glc_{IV}$ H-1 ($\delta_H$ 4.845/$\delta_C$ 106.6). Then the proton at $\delta_H$ 3.95, observed in the COSY spectrum, could be tentatively assigned to $Glc_{IV}$ C-2 ($\delta_H$ 3.95/$\delta_C$ 75.1) by HSQC data and by comparison with the chemical shifts of $Glc_{IV}$ H-2 in (2a). Selective irradiation of the anomeric protons at $\delta_H$ 4.85 with several different mixing times in a series of 1-D TOCSY experiments affected both protons at $\delta_H$ 4.845 and 4.850. Therefore, tentative assignment of $Glc_{IV}$ had to be performed by analysis of the TOCSY, HSQC, and HSQC-TOCSY data. $Glc_{IV}$ H-2 is clearly observed in the TOCSY data at 20 msec, together with $\delta_H$ 4.06, the H-2 of the other sugar. Additional TOCSY analysis suggests that the protons at $\delta_H$ 4.23 and 4.27 correspond to H-3 in both $Glc_{IV}$ and the other sugar unit, allowing the assignment of $Glc_{IV}$ C-3 ($\delta_H$ 4.23/$\delta_C$ 77.9) by HSQC. Further analysis of TOCSY data revealed additional protons at $\delta_H$ 4.18, 4.13, 4.06, 3.95, 4.35, and 4.50 at increasing mixing times. HSQC-TOCSY data indicated that $Glc_{IV}$ H-1 is correlated to a carbon at $\delta_C$ 69.9 which is an oxygenated methylene and can be assigned to $Glc_{IV}$ C-6 ($\delta_H$ 4.35, 4.83/$\delta_C$ 69.9) after TOCSY, HSQC and COSY analysis. The proton at $\delta_H$ 4.83 showed COSY correlations to protons at $\delta_H$ 4.06 which could be assigned to C-5 ($\delta_H$ 4.06/$\delta_C$ 74.9). Additional TOCSY, HSQC, and HSQC-TOCSY analysis allowed to tentatively assign $Glc_{IV}$ C-4 ($\delta_H$ 4.13/$\delta_C$ 77.0).

The observation of an HMBC correlation of the anomeric protons at $\delta_H$ 4.850 and 5.18 to carbons at $\delta_C$ 69.9 indicates that one of this anomeric protons links to $Glc_{IV}$ C-6. This information does not allow to unambiguously assign those anomeric protons. Therefore, the assignment of $Glc_V$ H-1 ($\delta_H$ 5.18/$\delta_C$ 104.9) by HSQC is just tentative and based on the pattern observed in (2a). COSY correlations of this anomeric proton allowed the assignment of $Glc_V$ C-2 ($\delta_H$ 4.06/$\delta_C$ 74.9). A series of 1-D TOCSY experiments selecting $Glc_V$ H-1, together with the HSQC and HSQC-TOCSY data allowed assignment of $Glc_V$ C-3 ($\delta_H$ 4.31/$\delta_C$ 78.0), C-4 ($\delta_H$ 4.19/$\delta_C$ 71.3), C-5 ($\delta_H$ 4.00/$\delta_C$ 78.1), and C-6 ($\delta_H$ 4.35, 4.54/$\delta_C$ 62.5) by HSQC.

There is no evidence of additional connectivities to $Glc_{IV}$ or $Glc_V$, and among the three remaining glucose units, only the anomeric protons at $\delta_H$ 4.850 ($\delta_C$ 104.5) and 5.56 ($\delta_C$ 104.6) show HMBC correlations to carbons at $\delta_C$ 69.9 and 81.1, respectively. These carbons do not belong to the aglycone, therefore, the anomeric proton at $\delta_H$ 4.93 ($\delta_C$ 103.7) can be assigned as $Glc_I$ H-1, and has to be connected to C-24. This connectivity was also proposed for (2a) and it is supported by a similar connectivity reported for Mogroside IVa, V, and VI (J. Carb. Chem. 2011, 30, 16-26). In all those cases, $Glc_I$ H-1 is connected to C-24.

$Glc_I$ H-1 showed a COSY correlation with a proton at $\delta_H$ 4.29. A series of 1-D TOCSY experiments selecting this anomeric proton, together with the COSY, HSQC and HSQC-TOCSY data allowed assignment of $Glc_I$ C-2 ($\delta_H$ 4.29/$\delta_C$ 81.1), C-3 ($\delta_H$ 4.30/$\delta_C$ 78.3), C-4 ($\delta_H$ 3.98/$\delta_C$ 71.0), C-5 ($\delta_H$ 4.10/$\delta_C$ 76.1), and C-6 ($\delta_H$ 3.98, 4.89/$\delta_C$ 69.9).

An HMBC correlation of the anomeric proton at $\delta_H$ 4.850 to $Glc_I$ C-6 allowed its assignment as $Glc_{II}$ H-1. Selective irradiation of this proton was performed before to obtain a series of 1-D TOCSY data. This experiment confirmed the assignment of $Glc_{II}$ C-2 ($\delta_H$ 4.06/$\delta_C$ 74.9). Additional analysis of the TOCSY, HSQC, and HSQC-TOCSY data allowed the assignment of $Glc_{II}$ C-3 ($\delta_H$ 4.27/$\delta_C$ 77.6), C-4 ($\delta_H$ 4.18/$\delta_C$ 71.3), and C-5 ($\delta_H$ 3.95/$\delta_C$ 78.0). An additional COSY correlation of H-5 to a proton at $\delta_H$ 4.50 allowed the assignment of C-6 ($\delta_H$ 4.30, 4.50/$\delta_C$ 62.2) by HSQC.

An HMBC correlation of the anomeric proton at $\delta_H$ 5.56 allowed its assignment as $Glc_{III}$ H-1. This anomeric proton showed a COSY correlation with a proton at $\delta_H$ 4.11. Analysis of 1-D TOCSY experiments performed by selecting this anomeric proton, together with the analysis of HSQC and HSQC-TOCSY data allowed the assignment of Glc$_{III}$ C-2 ($\delta_H$ 4.11/$\delta_C$ 75.6), C-3 ($\delta_H$ 4.23/$\delta_C$ 77.9), C-4 ($\delta_H$ 4.07/$\delta_C$ 71.9), C-5 ($\delta_H$ 4.00/$\delta_C$ 78.1), and C-6 ($\delta_H$ 4.32, 4.60/$\delta_C$ 63.1).

A summary of the $^1$H and $^{13}$C chemical shifts for the glycoside at C-3 are found in Table 11.

TABLE 11

$^1$H and $^{13}$C NMR (500 and 125 MHz, pyridine-d$_5$ D$_2$O (10:1)) assignments of the (2b) C-3 glycoside.[a, b, c]

| Position | $^{13}$C NMR | $^1$H NMR |
|---|---|---|
| Glc$_{II}$-1 | 106.6 | 4.845 d (7.3) |
| Glc$_{II}$-2 | 75.1 | 3.95 m |
| Glc$_{II}$-3 | 77.9 | 4.23 m |
| Glc$_{II}$-4 | 77.0 | 4.13 m |
| Glc$_{II}$-5 | 74.9 | 4.06 m |
| Glc$_{II}$-6 | 69.9 | 4.35 m |
|  |  | 4.83 m |
| Glc$_{I'}$-1 | 104.9 | 5.18 d (7.9) |
| Glc$_{I'}$-2 | 74.9 | 4.06 m |
| Glc$_{I'}$-3 | 78.0 | 4.31 m |
| Glc$_{I'}$-4 | 71.3 | 4.19 m |
| Glc$_{I'}$-5 | 78.1 | 4.00 m |
| Glc$_{I'}$-6 | 62.5 | 4.35 m |
|  |  | 4.54 d (12) |

[a] assignments made on the basis of COSY, HSQC, HMBC, TOCSY and HSQC-TOCSY correlations;
[b] Chemical shift values are in δ (ppm);
[c] Coupling constants are in Hz.

A summary of the $^1$H and $^{13}$C chemical shifts for the glycoside at C-24 are found in Table 12.

TABLE 12

$^1$H and $^{13}$C NMR (500 and 125 MHz, (pyridine-d$_5$/D$_2$O (10:1)) assignments of the (2b) C-24 glycoside.[a, b, c]

| Position | $^{13}$C NMR | $^1$H NMR |
|---|---|---|
| Glc$_{I}$-1 | 103.7 | 4.93 d (6.8) |
| Glc$_{I}$-2 | 81.1 | 4.29 m |
| Glc$_{I}$-3 | 78.3 | 4.30 m |
| Glc$_{I}$-4 | 71.0 | 3.98 m |
| Glc$_{I}$-5 | 76.1 | 4.10 m |
| Glc$_{I}$-6 | 69.9 | 3.98 m |
|  |  | 4.89 d (9.7) |
| Glc$_{II}$-1 | 104.5 | 4.85 d (7.3) |
| Glc$_{II}$-2 | 74.9 | 4.06 m |
| Glc$_{II}$-3 | 77.6 | 4.27 m |
| Glc$_{II}$-4 | 71.3 | 4.18 m |
| Glc$_{II}$-5 | 78.0 | 3.95 m |
| Glc$_{II}$-6 | 62.2 | 4.30 m |
|  |  | 4.50 d (11) |
| Glc$_{III}$-1 | 104.6 | 5.56 d (7.9) |
| Glc$_{III}$-2 | 75.6 | 4.11 m |
| Glc$_{III}$-3 | 77.9 | 4.23 m |
| Glc$_{III}$-4 | 71.9 | 4.07 m |
| Glc$_{III}$-5 | 78.1 | 4.00 m |
| Glc$_{III}$-6 | 63.1 | 4.32 m |
|  |  | 4.60 d (12) |

[a] assignments made on the basis of COSY, HSQC, HMBC, TOCSY and HSQC-TOCSY correlations;
[b] Chemical shift values are in δ (ppm);
[c] Coupling constants are in Hz.

Example 5

Isolation and Purification of (2c)

Figure 7:
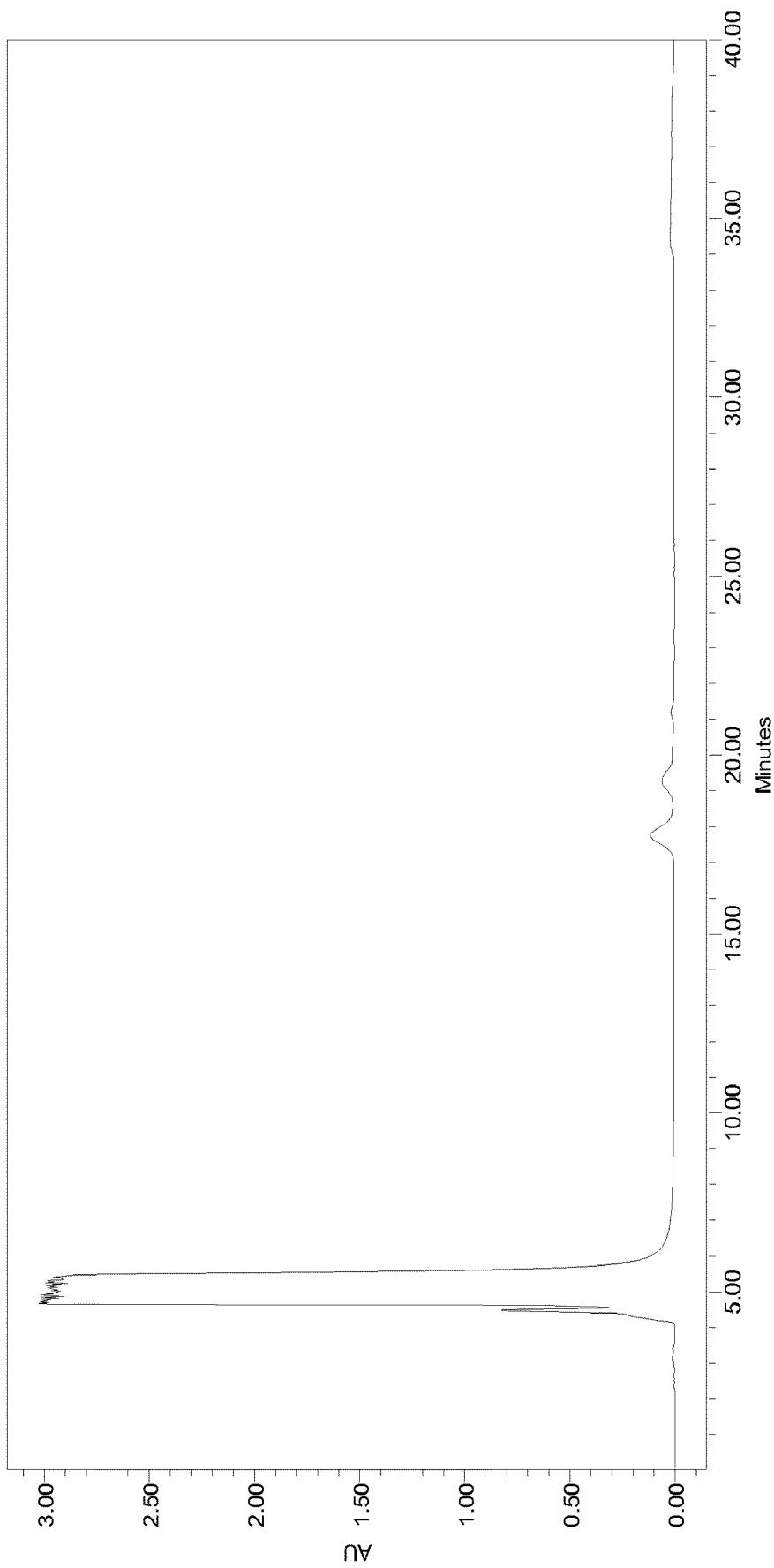
FIG. 7: HPLC chromatogram for the final round of purification of extract VSPC-2973-45-ML-1.

A mogrol glycoside (2c) was isolated from the extract VSPC-2973-45-ML-1. Under LC-MS method described above method, (2c) eluted at 20.5 min. The ESI− mass spectrum showed the expected [M−H]− ions at m/z 1431. First round of purification of extract VSPC-2973-45-ML-1 was carried out using the HPLC method 1. Under this method, (2c) eluted between 19 and 21 min. Second round of purification of extract VSPC-2973-45-ML-1, was carried out using the HPLC method (2b). Under this method (2c) eluted between 6.5 and 8.5 min. Third round of purification of (2c) was carried out using HPLC method 3B. (2c) elutes at 16.4 min under this method. FIG. 7 illustrates the HPLC chromatograms of the final round of purification of (2c) using HPLC method 4. (2c) elutes at 17.7 min under this method. This peak was collected over several injections and dried by rotary evaporation under reduced pressure.

Example 6

Structural Elucidation of (2c)

Mass Spectrometry

Figure 8:
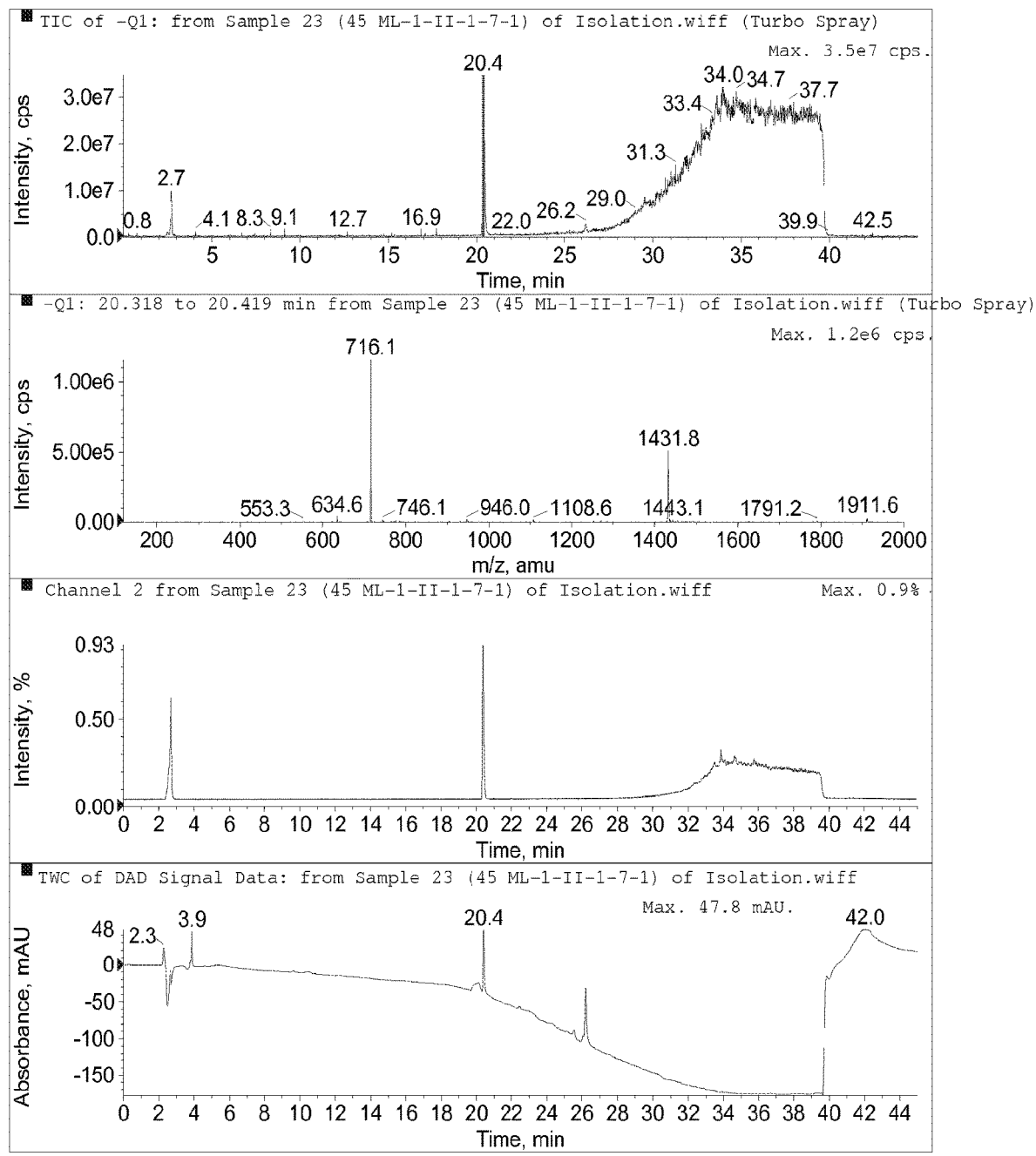
FIG. 8: LC-MS analysis of isolated sample of (2c) showing, from top to bottom, TIC, mass spectrum of the (2c) peak at 20.4 min, ELS chromatogram and UV (PDA) chromatogram.

The results of an LC-MS analysis of the isolated peak are shown in FIG. 8 and confirmed that it corresponded to (2c). A single peak was observed in the TIC, UV and ELS chromatograms. The ESI+ TOF mass spectrum of (2c) showed [M+H]$^+$ and [M+Na]$^+$ ions at m/z 1433.7169 and 1455.6981, respectively. The mass of the [M+H]$^-$ ion was in good agreement with the molecular formula $C_{66}H_{112}O_{33}$ (calcd for $C_{66}H_{113}O_{33}$: 1433.7164 error: 0.5 mDa) expected for (2c). The ESI− TOF mass spectrum of the isolate of (2c) showed [M−H]$^-$ ions at m/z 1431.7008. The mass of the [M−H]$^-$ ion was in good agreement with the molecular formula $C_{66}H_{112}O_{33}$ (calcd for $C_{66}H_{111}O_{33}$: 1431.7008, error: 0.0 mDa) expected for (2b). The MS data confirmed that (2c) has a nominal mass of 1432 Daltons with the molecular formula, $C_{66}H_{112}O_{33}$.

The MS/MS spectrum of (2c), selecting the [M−H]$^-$ ion at m/z 1431 for fragmentation, indicated the loss of 6 sugar moieties at m/z 1269.6481, 1107.5962, 945.5418, 783.4893, 621.4377, and 459.3869. The difference of 162 mass units suggests the presence of six glucose moieties, characteristic of mogrol glycosides. There is no distinctive pattern to determine show these glucose moieties are linked to the aglycone.

NMR Spectrometry

Figure 9:
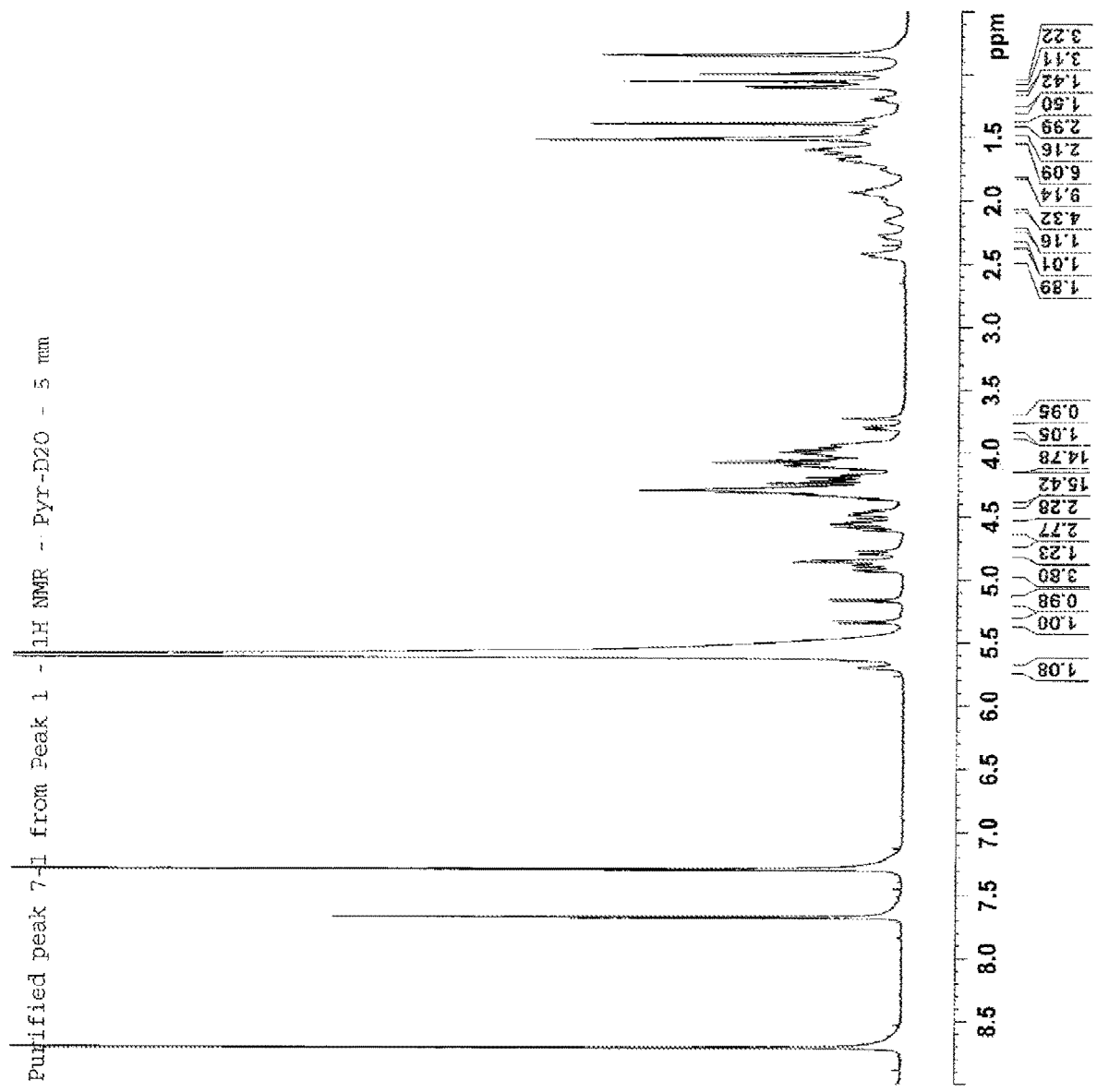
FIG. 9: 500 MHz $^1$H NMR spectrum of (2c) in pyridine-$d_5$/$D_2O$ (10:1).

A series of NMR experiments including $^1$H NMR (FIG. 9), $^1$H-$^1$H COSY, HSQC, HMBC, and HSQC-TOCSY were performed to allow assignment of (2c).

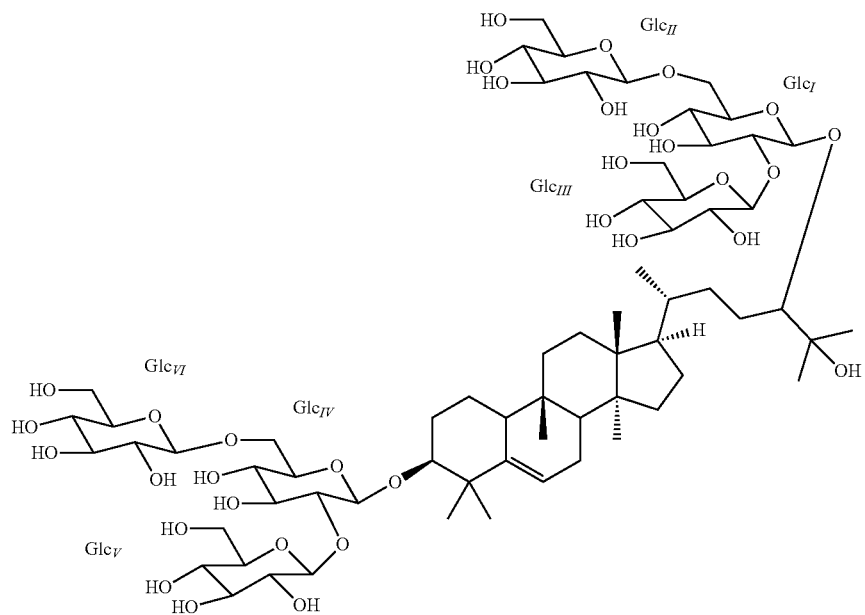

HMBC correlations were observed from the methyl protons at $\delta_H$ 1.06 and 1.50 to the olefinic carbon at $\delta_C$ 142.9, and to carbons at $\delta_C$ 86.6 and 41.5. Additional HMBC correlations of the protons at $\delta_H$ 1.06 to the carbon at $\delta_C$ 25.9 and from the protons at $\delta_H$ 1.50 to the carbon at $\delta_C$ 28.2 allowed the assignment of the germinal methyl singlets C-28 ($\delta_H$ 1.06/$\delta_C$ 28.2) and C-29 ($\delta_H$ 1.50/$\delta_C$ 25.9) and the methine C-3 ($\delta_H$ 3.72/$\delta_C$ 86.6) by HSQC data. The carbons at $\delta_C$ 41.5 and 142.9 did not show any HSQC correlations and they were assigned to C-4 and C-5, respectively.

COSY correlations between H-3 and the protons at $\delta_H$ 1.97 and $\delta_H$ 2.43 allowed assignment of C-2 ($\delta_C$ 28.8) by HSQC. One of the protons at $\delta_H$ 2.43 showed a subsequent COSY correlation with a proton at $\delta_H$ 1.92 which can be assigned to C-1 ($\delta_H$ 1.61, 1.92/$\delta_C$ 22.5) by HSQC (Table 13) and by comparison with C-1 in both (2a) and (2b). The H-1 protons showed additional COSY correlations to $\delta_H$ 2.28. The HSQC correlation of this proton to a carbon at $\delta_C$ 38.2 allowed its assignment as C-10.

TABLE 13

$^1$H and $^{13}$C NMR (500 and 125 MHz, (pyridine-d$_5$/D$_2$O (10:1)) assignments of the (2c) aglycone.[a, b, c]

| Position | $^{13}$C NMR | $^1$H NMR |
|---|---|---|
| 1 | 22.5 | 1.61 m |
|   |      | 1.92 m |
| 2 | 28.8 | 1.97 m |
|   |      | 2.43 d (11) |
| 3 | 86.6 | 3.72 bs |
| 4 | 41.5 | — |
| 5 | 142.9 | — |
| 6 | 119.2 | 5.70 bs |
| 7 | 24.7 | 1.67 m |
|   |      | 2.43 m |
| 8 | 43.8 | 1.59 m |
| 9 | 34.4 | — |
| 10 | 38.2 | 2.28 m |
| 11 | 32.5 | 1.35 m |
|    |      | 1.62 m |
| 12 | 30.9 | 1.44 m |
|    |      | 1.63 m |

TABLE 13-continued $^1$H and $^{13}$C NMR (500 and 125 MHz, (pyridine-d$_5$/D$_2$O (10:1)) assignments of the (2c) aglycone.[a, b, c]

| Position | $^{13}$C NMR | $^1$H NMR |
|---|---|---|
| 13 | 46.1 | — |
| 14 | 49.3 | — |
| 15 | 35.1 | 1.08 m |
|    |      | 1.20 m |
| 16 | 28.5 | 1.50 m |
|    |      | 2.16 m |
| 17 | 50.8 | 1.69 m |
| 18 | 15.8 | 0.84 s |
| 19 | 28.3 | 0.99 s |
| 20 | 36.2 | 1.57 m |
| 21 | 19.3 | 1.10 d (6.1) |
| 22 | 33.3 | 1.75 m |
|    |      | 2.00 m |
| 23 | 29.0 | 1.67 m |
|    |      | 1.94 m |
| 24 | 92.6 | 3.80 d (9.4) |
| 25 | 72.8 | — |
| 26 | 26.9 | 1.39 s |
| 27 | 24.6 | 1.52 s |
| 28 | 28.2 | 1.06 s |
| 29 | 25.9 | 1.50 s |
| 30 | 18.2 | 0.85 s |

[a] assignments made on the basis of COSY, HSQC, HMBC, TOCSY and HSQC-TOCSY correlations;
[b] Chemical shift values are in $\delta$ (ppm);
[c] Coupling constants are in Hz.

A third methyl singlet, observed at $\delta_H$ 0.99, showed HMBC correlations to C-10 and to carbons at $\delta_C$ 32.5, 34.4, and 43.8. Therefore, C-19 ($\delta_H$ 0.99/$\delta_C$ 28.3) could be assigned by HSQC. HSQC correlations also allowed the assignment of C-8 ($\delta_H$ 1.59/$\delta_C$ 43.8) and C-11 ($\delta_H$ 1.35, 1.62/$\delta_C$ 32.5), while the carbon at $\delta_C$ 34.4 is quaternary and should correspond to C-9. A second proton at $\delta_H$ 2.43 showed COSY correlations with H-8. This proton resembles the methylene C-7 in (2a) and (2b). The COSY correlation of this proton at $\delta_H$ 2.43 with a proton at $\delta_H$ 5.70 confirmed the spin system H-6/H-7/H-8 described in (2a) and (2b) that allows the assignment of C-7 ($\delta_H$ 1.67, 2.43/$\delta_C$ 24.7) and C-6 ($\delta_H$ 5.70/$\delta_C$ 119.2) through HSQC correlations. Overlap in the COSY correlations of the H-11 protons did not allow further assignments. However, the methylene protons at $^1$H 1.44 and 1.63 are reminiscent of C-12 in (2a) and (2b). These protons correlate with the carbon at $\delta_C$ 30.9 and can tentatively be assigned as C-12 ($\delta_H$ 1.44, 1.63/$\delta_C$ 30.9) by HSQC correlations.

The observation of an HMBC correlation of a fourth methyl singlet at $\delta_H$ 0.84 with the carbon at $\delta_C$ 30.9 added further support to the assignment of C-12 and allowed to propose the assignment of C-18 ($\delta_H$ 0.84/$\delta_C$ 15.8). Additional HMBC correlations of the proposed H-18 to C-12 and to carbons at $\delta_C$ 46.1, 49.3, and 50.8 allowed confirming the assignments of C-12 and C-18. These correlations allowed also the assignment of C-17 ($\delta_H$ 1.69/$\delta_C$ 50.8) by HSQC. The quaternary carbons at $\delta_C$ 46.1 and 49.3 correspond to C-13 and C-14 but they could be interchanged since there are no other HMBC correlations that could unambiguously assign them.

A fifth methyl singlet at $\delta_H$ 0.85 also showed HMBC correlations to C-13 and C-14, in addition to correlations to C-8 and a carbon at $\delta_C$ 35.1. The HSQC correlations of this carbon indicate that it is a methylene unit that is linked to protons at $\delta_H$ 1.08 and 1.20. These protons show COSY correlations to a proton at $\delta_H$ 2.16 which subsequently correlates to H-17 and to a proton at $\delta_H$ 1.50. All this information, together with analysis of HSQC data allowed the assignment of C-30 ($\delta_H$ 0.85/$\delta_C$ 18.2), C-15 ($\delta_H$ 1.08, 1.20/$\delta_C$ 35.1) and C-16 ($\delta_H$ 1.50, 2.16/$\delta_C$ 28.5).

A sixth methyl group was observed as a doublet at $\delta_H$ 1.10 and it showed HMBC correlations to carbons at $\delta_C$ 33.0, 36.1, and C-17. These methyl protons also showed COSY correlations to a proton at $\delta_H$ 1.57 which allowed the assignment of C-21 ($\delta_H$ 1.10/$\delta_C$ 19.3) and C-20 ($\delta_H$ 1.57/$\delta_C$ 36.2) by HSQC. A COSY correlation of H-20 to a proton at $\delta_H$ 2.00 allowed assigning of C-22 ($\delta_H$ 1.75, 2.00/$\delta_C$ 33.3) by HSQC. Subsequent COSY correlations of the proton at $\delta_H$ 2.00 to the proton at $\delta_H$ 1.67, which in turn correlates to the proton at $\delta_H$ 3.80, also confirmed the assignment of C-23 ($\delta_H$ 1.67, 1.94/$\delta_C$ 29.0) and C-24 ($\delta_H$ 3.80/$\delta_C$ 92.6) by HSQC.

The remaining two methyl singlets that resonate at $\delta_H$ 1.39 and 1.52 showed HMBC correlations to each other at $\delta_C$ 24.6, and 26.9. Additional HMBC correlations of these methyl protons to C-24 and to a carbon at $\delta_C$ 72.8 allowed the assignment of C-26 ($\delta_H$ 1.39/$\delta_C$ 26.9) and C-27 ($\delta_H$ 1.52/$\delta_C$ 24.6) by HSQC. These data indicate that these methyl groups are geminal and their assignments are interchangeable since they should be linked to the achiral carbon at $\delta_C$ 72.8, which in turn could be assigned to C-25.

An analysis of the HSQC data for (2c) confirmed the presence of six anomeric protons that were observed in the $^1$H NMR spectrum at $\delta_H$ 5.56 ($\delta_C$ 104.7), 5.34 ($\delta_C$ 104.7), 5.16 ($\delta_C$ 105.0), 4.93 ($\delta_C$ 103.8), 4.85 ($\delta_C$ 104.5), and 4.85 ($\delta_C$ 104.5). These chemical shifts are very similar to those encountered in (2a) and (2b) with the exception of the anomeric proton at $\delta_H$ 5.34 ($\delta_C$ 104.7) which correspond to an additional sugar.

None of the anomeric protons showed HMBC correlations to the aglycone, therefore, the assignment of the sugars had to be performed by comparison with those in (2a) and (2b). As in (2a) and (2b), one of the two anomeric protons observed at $\delta_H$ 4.85 can be tentatively assigned to Glc$_{IV}$ H-1. Likewise, the anomeric proton that resonates at $\delta_H$ 4.93 ($\delta_C$ 103.8) is the best candidate to be considered Glc$_I$ H-1.

Only one of the two anomeric protons at $\delta_H$ 4.85 showed a HMBC correlation to a carbon at $\delta_C$ 70.0. These protons could be distinguished in the COSY spectrum as the protons at $\delta_H$ 4.855 and 4.850. They correlate to protons at $\delta_H$ 4.28 and 4.06, respectively, which should correspond to H-2 of two sugars. Comparison of these chemical shifts with the respective Glc$_{II}$ H-2 and Glc$_{IV}$ H-2 in (2a) ($\delta_H$ 4.06 and 3.98) and in (2b) ($\delta_H$ 4.06 and 3.95), strongly suggests that the proton at $\delta_H$ 4.850 is Glc$_{II}$ H-1, while the proton at $\delta_H$ 4.855 could be assigned to Glc$_{IV}$ H-1. The downfield shift observed in H-2 of (2c) ($\delta_H$ 4.28) could be explained by the linkage of an additional sugar to Glc$_{IV}$ C-2. This linkage is supported by the observation of an HMBC correlation of the anomeric proton at $\delta_H$ 5.34 ($\delta_C$ 104.7) to a carbon a $\delta_C$ 81.3 which belongs to the same sugar as the proposed Glc$_{IV}$ H-1 after analysis of the HSQC-TOCSY data. These considerations allowed the assignment of Glc$_{IV}$ C-1 ($\delta_H$ 4.855/$\delta_C$ 104.5), Glc$_{IV}$ C-2 ($\delta_H$ 4.28/$\delta_C$ 81.3), Glc$_{II}$ C-1 ($\delta_H$ 4.850/$\delta_C$ 104.5), and Glc$_{II}$ C-2 ($\delta_H$ 4.06/$\delta_C$ 75.0). Selective irradiation of the anomeric protons at $\delta_H$ 4.85 with several different mixing times in a series of 1-D TOCSY experiments affected both protons at $\delta_H$ 4.850 and 4.855, but the protons at $\delta_H$ 4.06 and 4.28 are clearly observed in the TOCSY data at 20 msec adding further support to the assignments of Glc$_{II}$ C-2 and Glc$_{IV}$ C-2. Additional analysis of 1-D TOCSY, HSQC, and HSQC-TOCSY data, and comparison with the data obtained for (2a) and (2b) allowed the assignment of Glc$_{II}$ C-3 ($\delta_H$ 4.29/$\delta_C$ 78.2), Glc$_{II}$ C-4 ($\delta_H$ 4.18/$\delta_C$ 71.5), Glc$_{II}$ C-5 ($\delta_H$ 3.93/$\delta_C$ 78.2), and Glc$_{II}$ C-6 ($\delta_H$ 4.30, 4.50/$\delta_C$ 62.4). Likewise, Glc$_{IV}$ C-3 ($\delta_H$ 4.29/$\delta_C$ 78.2), Glc$_{IV}$ C-4 ($\delta_H$ 3.98/$\delta_C$ 71.2), and Glc$_{IV}$ C-5 ($\delta_H$ 4.07/$\delta_C$ 76.8) could also be assigned. COSY correlations observed between H-5 and the proton at $\delta_H$ 4-18 allowed the assignment of Glc$_{IV}$ C-6 ($\delta_H$ 4.32, 4.18/$\delta_C$ 69.8) by HSQC.

The anomeric proton at $\delta_H$ 5.34 ($\delta_C$ 104.7) could be assigned to Glc$_V$ H-1 due to its connection to Glc$_{IV}$ C-2 as described previously. COSY correlations of this anomeric proton with a proton at $\delta_H$ 4.09 allowed the assignment of Glc$_V$ C-2 ($\delta_H$ 4.09/$\delta_C$ 76.8). A series of 1-D TOCSY experiments selecting Glc$_V$ H-1, together with the analysis of HSQC and HSQC-TOCSY data allowed assignment of Glc$_V$ C-3 ($\delta_H$ 4.24/$\delta_C$ 77.7), C-4 ($\delta_H$ 4.30/$\delta_C$ 71.3), and C-5 ($\delta_H$ 3.92/$\delta_C$ 78.2). A COSY correlation between H-5 and the proton at $\delta_H$ 4.46 allowed the assignment of Glc$_V$ C-6 ($\delta_H$ 4.46, 4.55/$\delta_C$ 62.5) by HSQC.

An HMBC correlation of the anomeric proton at $\delta_H$ 5.16 to Glc$_{IV}$ C-6 allowed its assignment as Glc$_{VI}$ H-1. A COSY correlation of this anomeric proton was observed with a proton at $\delta_H$ 4.07. Analysis of 1-D TOCSY experiments performed by selecting this anomeric proton, together with the analysis of HSQC and HSQC-TOCSY data allowed the assignment of Glc$_{VI}$ C-2 ($\delta_H$ 4.07/$\delta_C$ 74.9), C-3 ($\delta_H$ 4.29/$\delta_C$ 78.2), C-4 ($\delta_H$ 4.19/$\delta_C$ 71.5), C-5 ($\delta_H$ 4.01/$\delta_C$ 78.3), and C-6 ($\delta_H$ 4.35, 4.57/$\delta_C$ 62.6).

There is no evidence of additional connectivities to Glc$_{IV}$, Glc$_V$, or Glc$_{VI}$ but only one of the two remaining anomeric protons at $\delta_H$ 5.56 ($\delta_C$ 104.7) show an HMBC correlation to a carbon at $\delta_C$ 81.1. These carbons do not belong to the aglycone, therefore, the anomeric proton that resonates at $\delta_H$ 4.93 ($\delta_C$ 103.8) can be confirmed as Glc$_I$ H-1, and has to be connected to C-24. This connectivity was also proposed for (2a) and (2b) and it is supported by a similar connectivity reported for Mogroside IVa, V, and VI (J. Carb. Chem. 2011, 30, 16-26). In all those cases, Glc$_I$ H-1 is connected to C-24.

Glc$_I$ H-1 showed a COSY correlation with a proton at $\delta_H$ 4.29. A series of 1-D TOCSY experiments selecting this anomeric proton, together with comparison of similar experiments for (2a) and (2b), and the analysis of COSY, HSQC, and HSQC-TOCSY data allowed assignment of Glc$_I$ C-2 ($\delta_H$ 4.29/$\delta_C$ 81.1), C-3 ($\delta_H$ 4.29/$\delta_C$ 78.2), C-4 ($\delta_H$ 3.98/$\delta_C$ 71.2), C-5 ($\delta_H$ 4.09/$\delta_C$ 76.3), and C-6 ($\delta_H$ 3.98, 4.89/$\delta_C$ 70.0). The observed HMBC correlation of Glc$_{II}$ H-1 to C-6 determined the connectivity between Glc$_I$ and Glc$_{II}$.

An HMBC correlation of the anomeric proton at $\delta_H$ 5.56 to Glc$_I$ C-2 allowed its assignment as Glc$_{III}$ H-1. This anomeric proton is overlapped by the water signal but a COSY correlation with a proton at $\delta_H$ 4.11 could be observed. Analysis of 1-D TOCSY experiments performed by selecting this anomeric proton, together with the analysis of HSQC and HSQC-TOCSY data allowed the assignment of Glc$_{III}$ C-2 ($\delta_H$ 4.11/$\delta_C$ 75.8), C-3 ($\delta_H$ 4.23/$\delta_C$ 78.0), C-4 ($\delta_H$ 4.07/$\delta_C$ 72.2), C-5 ($\delta_H$ 4.01/$\delta_C$ 78.2), and C-6 ($\delta_H$ 4.32, 4.60/$\delta_C$ 63.3).

A summary of the $^1$H and $^{13}$C chemical shifts for the glycoside at C-3 are found in Table 14.

TABLE 14

$^1$H and $^{13}$C NMR (500 and 125 MHz, pyridine-d$_5$ D$_2$O (10:1)) assignments of the (2c) C-3 glycoside.[a, b, c]

| Position | $^{13}$C NMR | $^1$H NMR |
|---|---|---|
| Glc$_{IV}$-1 | 104.5 | 4.855 d (7.7) |
| Glc$_{IV}$-2 | 81.3 | 4.28 m |
| Glc$_{IV}$-3 | 78.2 | 4.29 m |
| Glc$_{IV}$-4 | 71.2 | 3.98 m |
| Glc$_{IV}$-5 | 76.8 | 4.07 m |
| Glc$_{IV}$-6 | 69.8 | 4.32 m |
| | | 4.78 m |
| Glc$_V$-1 | 104.7 | 5.34 d (7.7) |
| Glc$_V$-2 | 76.8 | 4.09 m |
| Glc$_V$-3 | 77.7 | 4.24 m |
| Glc$_V$-4 | 71.3 | 4.30 m |
| Glc$_V$-5 | 78.2 | 3.92 m |
| Glc$_V$-6 | 62.5 | 4.46 m |
| | | 4.55 m |
| Glc$_{VI}$-1 | 105.0 | 5.16 d (7.8) |
| Glc$_{VI}$-2 | 74.9 | 4.07 m |
| Glc$_{VI}$-3 | 78.2 | 4.29 m |
| Glc$_{VI}$-4 | 71.5 | 4.19 m |
| Glc$_{VI}$-5 | 78.3 | 4.01 m |
| Glc$_V$-6 | 62.6 | 4.35 m |
| | | 4.57 m |

[a] assignments made on the basis of COSY, HSQC, HMBC, TOCSY and HSQC-TOCSY correlations;
[b] Chemical shift values are in $\delta$ (ppm);
[c] Coupling constants are in Hz.

A summary of the $^1$H and $^{13}$C chemical shifts for the glycoside at C-24 are found in Table 15.

TABLE 15

$^1$H and $^{13}$C NMR (500 and 125 MHz, (pyridine-d$_5$/D$_2$O (10:1)) assignments of the (2c) C-24 glycoside.[a, b, c]

| Position | $^{13}$C NMR | $^1$H NMR |
|---|---|---|
| Glc$_I$-1 | 103.8 | 4.93 d (7.1) |
| Glc$_I$-2 | 81.1 | 4.29 m |
| Glc$_I$-3 | 78.2 | 4.29 m |
| Glc$_I$-4 | 71.2 | 3.98 m |
| Glc$_I$-5 | 76.3 | 4.09 m |
| Glc$_I$-6 | 70.0 | 3.98 m |
| | | 4.89 d (9.5) |
| Glc$_{II}$-1 | 104.5 | 4.850 d (7.7) |
| Glc$_{II}$-2 | 75.0 | 4.06 m |
| Glc$_{II}$-3 | 78.2 | 4.29 m |
| Glc$_{II}$-4 | 71.5 | 4.18 m |
| Glc$_{II}$-5 | 78.2 | 3.93 m |
| Glc$_{II}$-6 | 62.4 | 4.30 m |
| | | 4.50 dd (1.9, 12) |
| Glc$_{III}$-1 | 104.7 | 5.56 m |
| Glc$_{III}$-2 | 75.8 | 4.11 m |
| Glc$_{III}$-3 | 78.0 | 4.23 m |
| Glc$_{III}$-4 | 72.2 | 4.07 m |
| Glc$_{III}$-5 | 78.2 | 4.01 m |

TABLE 15-continued $^1$H and $^{13}$C NMR (500 and 125 MHz, (pyridine-d$_5$/D$_2$O (10:1)) assignments of the (2c) C-24 glycoside.[a, b, c]

| Position | $^{13}$C NMR | $^1$H NMR |
|---|---|---|
| Glc$_{III}$-6 | 63.3 | 4.32 m |
| | | 4.60 dd (2.3, 12) |

[a] assignments made on the basis of COSY, HSQC, HMBC, TOCSY and HSQC-TOCSY correlations;
[b] Chemical shift values are in $\delta$ (ppm);
[c] Coupling constants are in Hz.

We claim:

1. A beverage or beverage product comprising at least one compound selected from the group consisting of:

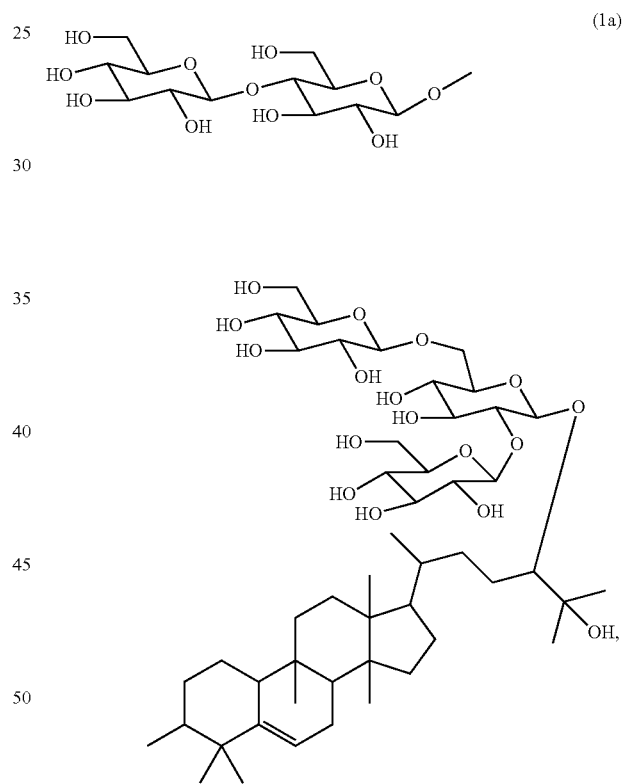

(1a)

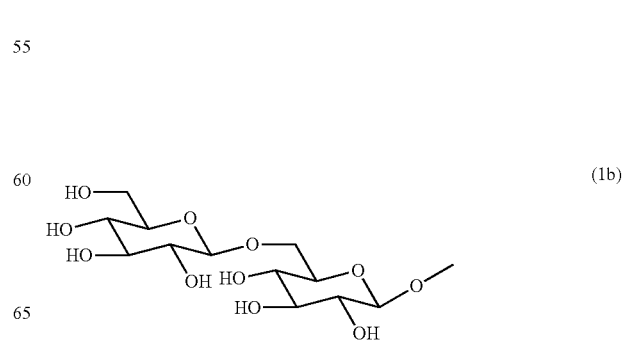

(1b)

-continued
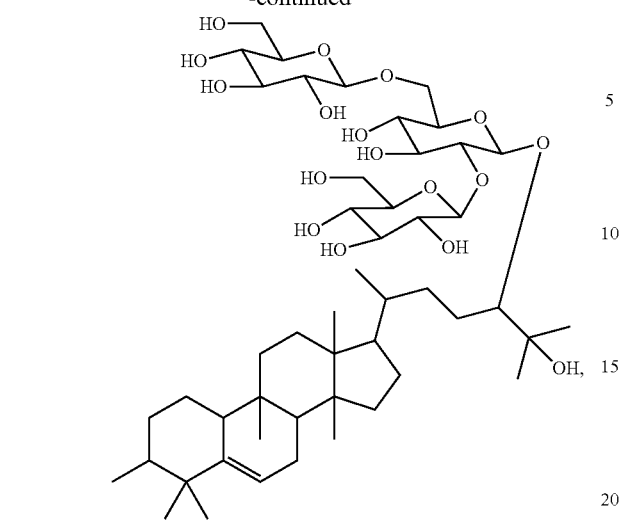
(1c)
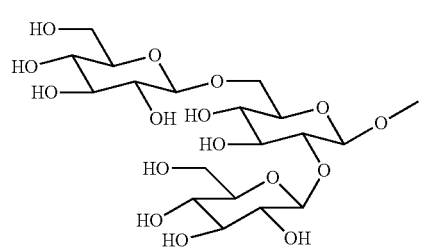
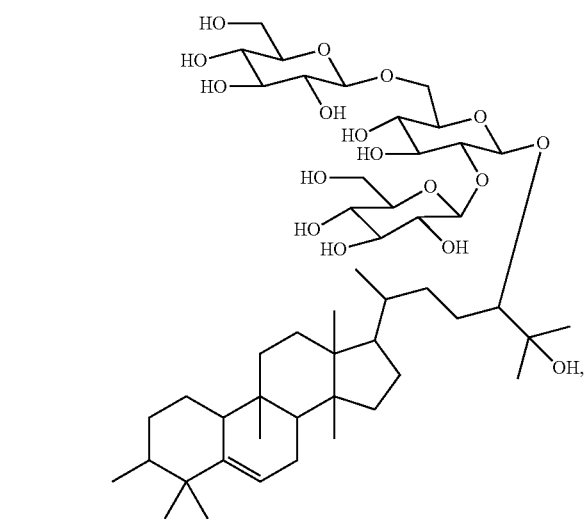
-continued
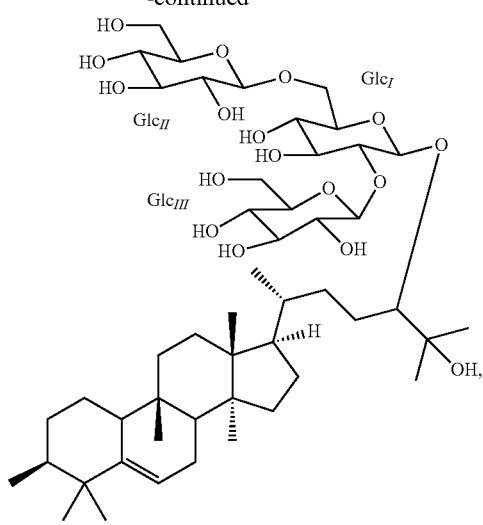
(2b)
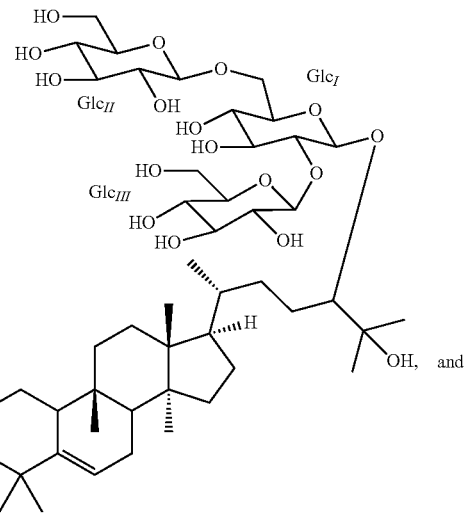
(2a)
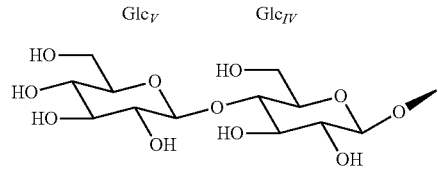
(2c)
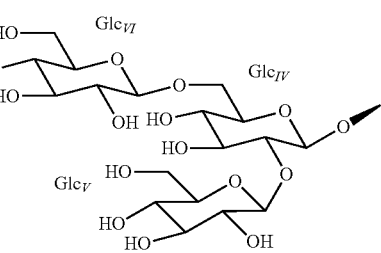

-continued

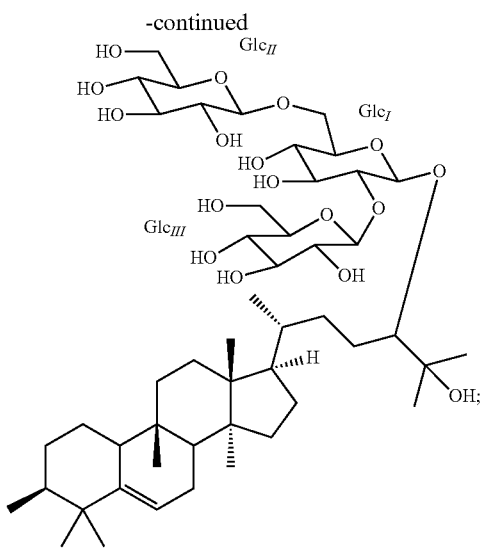

wherein the compound is present in a mixture in an amount from about 50% to about 90% by weight on a dry basis.

2. The beverage or beverage product of claim 1, wherein the mixture is selected from the group consisting of a mixture of mogrosides, Luo han guo extract, by-products of other mogrosides' isolation and purification processes, a commercially available Luo han guo extract and combinations thereof.

3. The beverage or beverage product of claim 1, further comprising at least one additional sweetener.

4. The beverage or beverage product of claim 3, wherein the at least one additional sweetener is selected from the group consisting of sucrose, fructose, glucose, high fructose corn syrup, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, stevia, rebaudioside A, stevioside, mogroside IV, siamenoside I, mogroside V, trilobatin and combinations thereof.

5. The beverage or beverage product of claim 1, further comprising at least one additive selected from the group consisting of carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

6. The beverage or beverage product of claim 1, further comprising at least one functional ingredient selected from the group consisting of saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

* * * * *